US012221616B2

(12) United States Patent
Kirn et al.

(10) Patent No.: US 12,221,616 B2
(45) Date of Patent: *Feb. 11, 2025

(54) ADENO-ASSOCIATED VIRUS VARIANT CAPSIDS AND METHODS OF USE THEREOF

(71) Applicant: 4D MOLECULAR THERAPEUTICS INC., Emeryville, CA (US)

(72) Inventors: David H. Kirn, Emeryville, CA (US); Melissa Kotterman, Emeryville, CA (US); David Schaffer, Emeryville, CA (US)

(73) Assignee: AD Molecular Therapeutics Inc., Emeryville, CA (US)

( * ) Notice: Subject to any disclaimer, the term of this patent is extended or adjusted under 35 U.S.C. 154(b) by 773 days.

This patent is subject to a terminal disclaimer.

(21) Appl. No.: 17/400,041

(22) Filed: Aug. 11, 2021

(65) Prior Publication Data

US 2021/0380643 A1    Dec. 9, 2021

Related U.S. Application Data

(63) Continuation of application No. 16/648,195, filed as application No. PCT/US2018/051812 on Sep. 19, 2018, now Pat. No. 11,118,192.

(60) Provisional application No. 62/560,901, filed on Sep. 20, 2017.

(51) Int. Cl.
| | |
|---|---|
| C12N 15/86 | (2006.01) |
| A61K 9/00 | (2006.01) |
| A61K 38/17 | (2006.01) |
| A61K 38/44 | (2006.01) |
| A61K 38/47 | (2006.01) |
| A61K 48/00 | (2006.01) |
| A61P 21/00 | (2006.01) |
| C07K 14/005 | (2006.01) |
| C12N 7/00 | (2006.01) |
| C12N 9/10 | (2006.01) |
| C12N 15/864 | (2006.01) |

(52) U.S. Cl.
CPC .......... *C12N 15/86* (2013.01); *A61K 38/1719* (2013.01); *A61K 38/44* (2013.01); *A61K 38/47* (2013.01); *A61P 21/00* (2018.01); *C07K 14/005* (2013.01); *C12N 7/00* (2013.01); *C12N 9/1051* (2013.01); *C12N 15/8645* (2013.01); *C12Y 116/03001* (2013.01); *C12Y 204/01001* (2013.01); *C12Y 302/0102* (2013.01); *C12Y 302/01022* (2013.01); *A61K 9/0019* (2013.01); *A61K 48/00* (2013.01); *C12N 2750/14121* (2013.01); *C12N 2750/14122* (2013.01); *C12N 2750/14133* (2013.01); *C12N 2750/14143* (2013.01); *C12N 2750/14145* (2013.01); *C12N 2750/14171* (2013.01)

(58) Field of Classification Search
CPC ........ C12N 15/86; C12N 7/00; C12N 9/1051; C12N 15/8645; C12N 2750/14121; C12N 2750/14122; C12N 2750/14133; C12N 2750/14143; C12N 2750/14145; C12N 2750/14171; A61P 21/00; A61K 38/1719; A61K 38/44; A61K 38/47; A61K 9/0019; A61K 48/00; C07K 14/005; C12Y 116/03001; C12Y 204/01001; C12Y 302/0102; C12Y 302/01022

See application file for complete search history.

(56) References Cited

U.S. PATENT DOCUMENTS

| | | | |
|---|---|---|---|
| 9,193,956 B2 | 11/2015 | Schaffer et al. | |
| 10,046,016 B2 | 8/2018 | Schaffer et al. | |
| 10,202,657 B2 | 2/2019 | Schaffer et al. | |
| 11,118,192 B2 * | 9/2021 | Kirn ............... | C12Y 302/01022 |

(Continued)

FOREIGN PATENT DOCUMENTS

| | | | | |
|---|---|---|---|---|
| AU | 2012228376 A1 * | 9/2013 | ............. | A61P 21/00 |
| AU | 2018337833 B2 | 10/2020 | | |

(Continued)

OTHER PUBLICATIONS

Xie, Q., Bu, W., Bhatia, S., Hare, J., Somasundaram, T., Azzi, A., & Chapman, M. S. (2002). The Atomic Structure of Adeno-Associated Virus (AAV-2), A Vector for Human Gene Therapy. Proceedings of the National Academy of Sciences —PNAS, 99(16), 10405-10410. (Year: 2002).*

(Continued)

*Primary Examiner* — Rachel B Gill
*Assistant Examiner* — Carey Alexander Stuart
(74) *Attorney, Agent, or Firm* — Much Shelist P.C.; Christopher M. Cabral

(57) ABSTRACT

Provided herein are variant adeno-associated virus (AAV) capsid proteins having one or more modifications in amino acid sequence relative to a parental AAV capsid protein, which, when present in an AAV virion, confer increased infectivity of one or more types of muscle cells as compared to the infectivity of the muscle cells by an AAV virion comprising the unmodified parental AAV capsid protein. Also provided are recombinant AAV virions and pharmaceutical compositions thereof comprising a variant AAV capsid protein as described herein, methods of making these rAAV capsid proteins and virions, and methods for using these rAAV capsid proteins and virions in research and in clinical practice, for example in, e.g., the delivery of nucleic acid sequences to one or more muscle cells for the treatment of muscle disorders and diseases.

20 Claims, 28 Drawing Sheets
Specification includes a Sequence Listing.

(56) References Cited

U.S. PATENT DOCUMENTS

| | | | |
|---|---|---|---|
| 11,167,041 B2* | 11/2021 | Kirn | C12N 15/86 |
| 11,613,766 B2* | 3/2023 | Kirn | C12Y 302/01022 424/93.2 |
| 11,802,278 B2* | 10/2023 | Kirn | A61K 9/0019 |
| 2016/0376323 A1 | 12/2016 | Schaffer et al. | |
| 2017/0159026 A1 | 6/2017 | Kay et al. | |
| 2024/0018498 A1* | 1/2024 | Kirn | A61P 3/00 |

FOREIGN PATENT DOCUMENTS

| | | |
|---|---|---|
| JP | 2014-518614 A | 8/2014 |
| JP | 2016-526045 A | 9/2016 |
| JP | 2016-535034 A | 11/2016 |
| JP | 2017-510296 A | 4/2017 |
| JP | 2020-537508 A | 12/2020 |
| WO | 2012/145601 A2 | 10/2012 |
| WO | 2014/194132 A1 | 12/2014 |
| WO | 2015/066190 A1 | 5/2015 |
| WO | 2015/142941 A1 | 9/2015 |
| WO | 2016/141078 A1 | 9/2016 |
| WO | 2016/154344 A1 | 9/2016 |
| WO | 2017/096164 A1 | 6/2017 |
| WO | 2017/197355 A2 | 11/2017 |

OTHER PUBLICATIONS

Choudhury, S., et al., "In Vivo Selection Yields AAV-B1 Capsid for Central Nervous System and Muscle Gene Therapy," Molecular Therapy, vol. 24, No. 7, pp. 1247-1257 (Jun. 7, 2016—online publication).

Falk, D. J., et al., "Comparative Impact of AAV and Enzyme Replacement Therapy on Respiratory and Cardiac Function in Adult Pompe Mice," Molecular Therapy—Methods & Clinical Development, vol. 2, No. 15007 (Jan. 1, 2015).

Gerard, C., et al., "An AAV9 Coding for Frataxin Clearly Improved the symptoms and Prolonged the Life of Friedreich Ataxis Mouse Models." Molecular therapy—Methods & Clinical Development, vol. 1, No. 14044 (Jan. 1, 2014).

Li, C., et al., Development of Patient-Specific AAV Vectors After Neutralizing Anitbody Selection for Enhanced Muscle Gene Transfer, Molecular Therapy, vol. 24 No. 1, pp. 53-65 (Jan. 2016).

Michelfelder, S., et al., "Successful Expansion but Not Complete Restriction of Tropism of Adeno-Associated Virus by In Vivo Biopanning of Random Virus Display Peptide Libraries," PLoS One, vol. 4, Issue 4, e5122 (Apr. 9, 2009).

Muller, O., et al., "Random Peptide Libraries Displayed on Adeno-Associated Virus to Select for Targeted Gene Therapy Vectors," Nature Biotechnology, Gale Group Inc., vol. 21, No. 9, pp. 1040-1046 (Sep. 2003).

Perabo, L., et al., "In Vitro Selection of Viral Vectors with Modified Tropism: The Adeno-Associated Virus Display," Molecular Therapy, Elsevier Inc., vol. 8, No. 1, pp. 151-157 (Jul. 1, 2003).

Sharma, R., et al., "In vivo Genome Editing of the Albumin Locus as a Platform for Protein Replacement Tehrapy," Blood, The Journal of the American Society of Hematology, Cvol. 126, No. 15, pp. 1777-1784 (Oct. 8, 2015).

Shi, W., et al., "Insertional Mutagenesis of the Adeno-Associated Virus Type 2 (AAV2) Capsid Gene and Generation of AAV2 Vectors Targeted to Alternative Cell-Surface Receptors," Human Gene Therapy, vol. 12, No. 14, pp. 1697-1711 (Sep. 20, 2001).

Varadi, K., et al. "Novel Random Peptide Libraries Displayed on AAV Serotype 9 for Selection of Endothelial Cell- Directed Gene Transfer Vectors," Gene Therapy, vol. 19, pp. 800-809 (Aug. 2012).

Wu, P., et al., "Mutational Analysis of the Adeno-Associated Virus Type 2 (AAV-2) Capsid Gene and Construction of AAV2 Vectors with Altered Tropism," Journal of Viroloy, vol. 74, No. 18, pp. 9635-8657 (Sep. 15, 2000).

Yu, C-Y., et al., A Muscle-Targeting Peptide Displayed on AAV2 Improves Muscle Tropism on Systemic Delivery, Gene Therapy, vol. 16, p. 953-962 (2009).

Certificate of Grant for Australian Patent No. 2018337833 dated Oct. 8, 2020.

Notice of Acceptance of Application for Australian Patent Application No. 2018337833 dated Jun. 12, 2020.

Notice of Grant for Patent for Australian Patent Application No. 2018337833 dated Oct. 8, 2020.

Allowed claims of Japanese Patent Application 2020-516735.

Notice of Allowance for Japanese Patent Application 2020-516735 dated Dec. 22, 2020.

International Search Report of PCT/US2018/051812 dated Apr. 1, 2019.

Written Opinion of PCT/US2018/051812 dated Apr. 1, 2019.

Sequence alignments instant SEQ ID 43 with sequences from inventor's co-pending U.S. Pat. No. 10,214,566 B2 and U.S. Appl. No. 16/300,466 (Year 2021).

Sequence alignments instant SEQ ID 48 with sequences from inventor's co-pending U.S. Pat. No. 10,214,566 B2 and U.S. Appl. No. 16/300,466 (Year 2021).

The recent Office action issued by the EPO for the corresponding European application (EP18859241).

The claims deemed allowable by the EPO in the Office action.

* cited by examiner

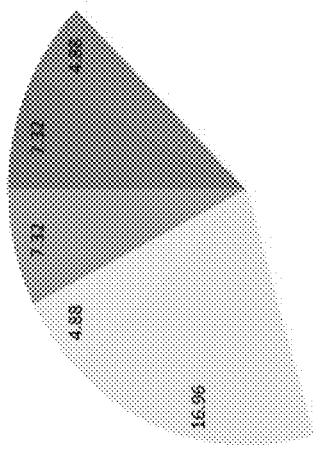
FIGURE 3A
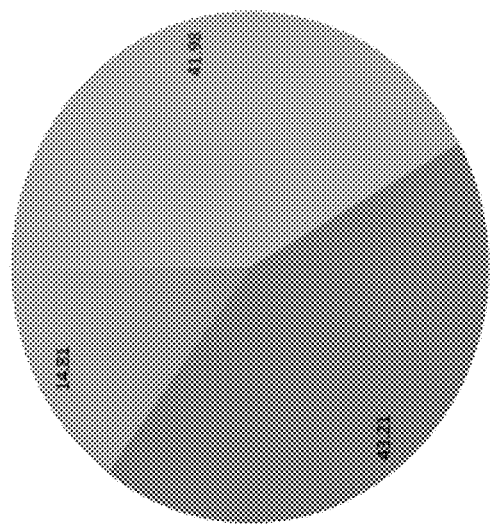
FIGURE 3C
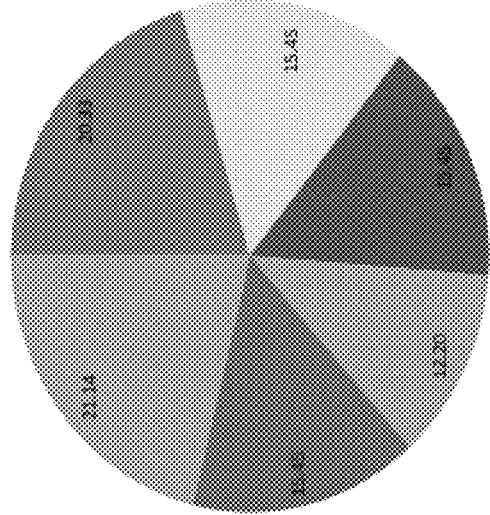
FIGURE 3B
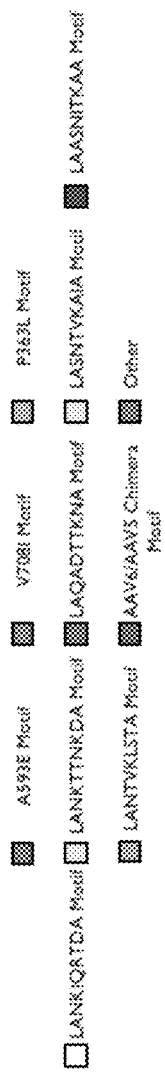

FIGURE 5

```
            1        10         20         30         40
AAV1    MAADGYLPDWLEDNLSEGIREWWDLKPGAPKPKANQQKQDDG
AAV2    MAADGYLPDWLEDTLSEGIRQWWKLKPGPPPPKPAERHKDDS
AAV3A   MAADGYLPDWLEDNLSEGIREWWALKPGVPQPKANQQHQDNR
AAV3B   MAADGYLPDWLEDNLSEGIREWWALKPGVPQPKANQQHQDNR
AAV4    M-TDGYLPDWLEDNLSEGVREWWALQPGAPKPKANQQHQDNA
AAV5    MSFVDHPPDWLEE-VGEGLREFLGLEAGPPKPKPNQQHQDQA
AAV6    MAADGYLPDWLEDNLSEGIREWWDLKPGAPKPKANQQKQDDG
AAV7    MAADGYLPDWLEDNLSEGIREWWDLKPGAPKPKANQQKQDNG
AAV8    MAADGYLPDWLEDNLSEGIREWWALKPGAPKPKANQQKQDDG
AAV9    MAADGYLPDWLEDNLSEGIREWWALKPGAPQPKANQQHQDNA
AAV10   MAADGYLPDWLEDNLSEGIREWWDLKPGAPKPKANQQKQDDG
                50         60         70         80
AAV1    RGLVLPGYKYLGPFNGLDKGEPVNAADAAALEHDKAYDQQLK
AAV2    RGLVLPGYKYLGPFNGLDKGEPVNEADAAALEHDKAYDRQLD
AAV3A   RGLVLPGYKYLGPGNGLDKGEPVNEADAAALEHDKAYDQQLK
AAV3B   RGLVLPGYKYLGPGNGLDKGEPVNEADAAALEHDKAYDQQLK
AAV4    RGLVLPGYKYLGPGNGLDKGEPVNAADAAALEHDKAYDQQLK
AAV5    RGLVLPGYNYLGPGNGLDRGEPVNRADEVAREHDISYNEQLE
AAV6    RGLVLPGYKYLGPFNGLDKGEPVNAADAAALEHDKAYDQQLK
AAV7    RGLVLPGYKYLGPFNGLDKGEPVNAADAAALEHDKAYDQQLK
AAV8    RGLVLPGYKYLGPFNGLDKGEPVNAADAAALEHDKAYDQQLQ
AAV9    RGLVLPGYKYLGPGNGLDKGEPVNAADAAALEHDKAYDQQLK
AAV10   RGLVLPGYKYLGPFNGLDKGEPVNAADAAALEHDKAYDQQLK
                90        100        110        120
AAV1    AGDNPYLRYNHADAEFQERLQEDTSFGGNLGRAVFQAKKRVL
AAV2    SGDNPYLKYNHADAEFQERLKEDTSFGGNLGRAVFQAKKRVL
AAV3A   AGDNPYLKYNHADAEFQERLQEDTSFGGNLGRAVFQAKKRIL
AAV3B   AGDNPYLKYNHADAEFQERLQEDTSFGGNLGRAVFQAKKRIL
AAV4    AGDNPYLKYNHADAEFQQRLQGDTSFGGNLGRAVFQAKKRVL
AAV5    AGDNPYLKYNHADAEFQEKLADDTSFGGNLGKAVFQAKKRVL
AAV6    AGDNPYLRYNHADAEFQERLQEDTSFGGNLGRAVFQAKKRVL
AAV7    AGDNPYLRYNHADAEFQERLQEDTSFGGNLGRAVFQAKKRVL
AAV8    AGDNPYLRYNHADAEFQERLQEDTSFGGNLGRAVFQAKKRVL
AAV9    AGDNPYLKYNHADAEFQERLKEDTSFGGNLGRAVFQAKKRLL
AAV10   AGDNPYLRYNHADAEFQERLQEDTSFGGNLGRAVFQAKKRVL
               130        140        150        160
AAV1    EPLGLVEEGAKTAPGKKRPVEQSPQ-EPDSSSGIGKTGQQPA
AAV2    EPLGLVEEPVKTAPGKKRPVEHSPV-EPDSSSGTGKAGQQPA
AAV3A   EPLGLVEEAAKTAPGKKGAVDQSPQ-EPDSSSGVGKSGKQPA
AAV3B   EPLGLVEEAAKTAPGKKRPVDQSPQ-EPDSSSGVGKSGKQPA
AAV4    EPLGLVEQAGETAPGKKRPLIESPQ-QPDSSTGIGKKGKQPA
AAV5    EPFGLVEEGAKTAPTGKRIDDHFPKRKKART----EEDSKPS
AAV6    EPFGLVEEGAKTAPGKKRPVEQSPQ-EPDSSSGIGKTGQQPA
AAV7    EPLGLVEEGAKTAPAKKRPVEPSPQRSPDSSTGIGKKGQQPA
AAV8    EPLGLVEEGAKTAPGKKRPVEPSPQRSPDSSTGIGKKGQQPA
AAV9    EPLGLVEEAAKTAPGKKRPVEQSPQ-EPDSSAGIGKSGAQPA
AAV10   EPLGLVEEAAKTAPGKKRPVEPSPQRSPDSSTGIGKKGQQPA
```

FIGURE 5 (continued)

```
         170       180       190       200       210
AAV1   KKRLNFGQTGDSESVPDPQPLGEPPATP-AAVGPTTMASGGG
AAV2   RKRLNFGQTGDADSVPDPQPLGQPPAAP-SGLGTNTMATGSG
AAV3A  RKRLNFGQTGDSESVPDPQPLGEPPAAP-TSLGSNTMASGGG
AAV3B  RKRLNFGQTGDSESVPDPQPLGEPPAAP-TSLGSNTMASGGG
AAV4   KKKLVFE----DETGAGDGPPEGSTSGA--MSDDSEMRAAAGG
AAV5   T-------SSDAEAGPSGSQQLQIPAQPASSLGADTMSAGGG
AAV6   KKRLNFGQTGDSESVPDPQPLGEPPATP-AAVGPTTMASGGG
AAV7   RKRLNFGQTGDSESVPDPQPLGEPPAAP-SSVGSGTVAAGGG
AAV8   RKRLNFGQTGDSESVPDPQPLGEPPAAP-SGVGPNTMAAGGG
AAV9   KKRLNFGQTGDTESVPDPQPIGEPPAAP-SGVGSLTMASGGG
AAV10  KKRLNFGQTGESESVPDPQPIGEPPAGP-SGLGSGTMAAGGG 220       230       240       250
AAV1   APMADNNEGADGVGNASGNWHCDSTWLGDRVITTSTRTWALP
AAV2   APMADNNEGADGVGNSSGNWHCDSTWMGDRVITTSTRTWALP
AAV3A  APMADNNEGADGVGNSSGNWHCDSQWLGDRVITTSTRTWALP
AAV3B  APMADNNEGADGVGNSSGNWHCDSQWLGDRVITTSTRTWALP
AAV4   AAV-EGGQGADGVGNASGDWHCDSTWSEGHVTTTSTRTWVLP
AAV5   GPLGDNNQGADGVGNASGDWHCDSTWMGDRVVTKSTRTWVLP
AAV6   APMADNNEGADGVGNASGNWHCDSTWLGDRVITTSTRTWALP
AAV7   APMADNNEGADGVGNASGNWHCDSTWLGDRVITTSTRTWALP
AAV8   APMADNNEGADGVGSSSGNWHCDSTWLGDRVITTSTRTWALP
AAV9   APVADNNEGADGVGSSSGNWHCDSQWLGDRVITTSTRTWALP
AAV10  APMADNNEGADGVGSSSGNWHCDSTWLGDRVITTSTRTWALP 260       270       280       290
AAV1   TYNNHLYKQISSA-STGASNDNHYFGYSTPWGYFDFNRFHCH
AAV2   TYNNHLYKQISSQ--SGASNDNHYFGYSTPWGYFDFNRFHCH
AAV3A  TYNNHLYKQISSQ--SGASNDNHYFGYSTPWGYFDFNRFHCH
AAV3B  TYNNHLYKQISSQ--SGASNDNHYFGYSTPWGYFDFNRFHCH
AAV4   TYNNHLYKRLGE-----SLQSNTYNGFSTPWGYFDFNRFHCH
AAV5   SYNNHQYREIKSGSVDG-SNANAYFGYSTPWGYFDFNRFHSH
AAV6   TYNNHLYKQISSA-STGASNDNHYFGYSTPWGYFDFNRFHCH
AAV7   TYNNHLYKQISSE-TAGSTNDNTYFGYSTPWGYFDFNRFHCH
AAV8   TYNNHLYKQISNGTSGGATNDNTYFGYSTPWGYFDFNRFHCH
AAV9   TYNNHLYKQISNSTSGGSSNDNAYFGYSTPWGYFDFNRFHCH
AAV10  TYNNHLYKQISNGTSGGSTNDNTYFGYSTPWGYFDFNRFHCH 300       310       320       330
AAV1   FSPRDWQRLINNNWGFRPKRLNFKLFNIQVKEVTTNDGVTTI
AAV2   FSPRDWQRLINNNWGFRPKRLNFKLFNIQVKEVTQNDGTTTI
AAV3A  FSPRDWQRLINNNWGFRPKKLSFKLFNIQVRGVTQNDGTTTI
AAV3B  FSPRDWQRLINNNWGFRPKKLSFKLFNIQVKEVTQNDGTTTI
AAV4   FSPRDWQRLINNNWGMRPKAMRVKIFNIQVKEVTTSNGETTV
AAV5   WSPRDWQRLINNYWGFRPRSLRVKIFNIQVKEVTVQDSTTTI
AAV6   FSPRDWQRLINNNWGFRPKRLNFKLFNIQVKEVTTNDGVTTI
AAV7   FSPRDWQRLINNNWGFRPKKLRFKLFNIQVKEVTTNDGVTTI
AAV8   FSPRDWQRLINNNWGFRPKRLSFKLFNIQVKEVTQNEGTKTI
AAV9   FSPRDWQRLINNNWGFRPKRLNFKLFNIQVKEVTDNNGVKTI
AAV10  FSPRDWQRLINNNWGFRPKRLSFKLFNIQVKEVTQNEGTKTI
```

FIGURE 5 (continued)

```
              340         350         360         370
AAV1    ANNLTSTVQVFSDSEYQLPYVLGSAHQGCLPPFPADVFMIPQ
AAV2    ANNLTSTVQVFTDSEYQLPYVLGSAHQGCLPPFPADVFMVPQ
AAV3A   ANNLTSTVQVFTDSEYQLPYVLGSAHQGCLPPFPADVFMVPQ
AAV3B   ANNLTSTVQVFTDSEYQLPYVLGSAHQGCLPPFPADVFMVPQ
AAV4    ANNLTSTVQIFADSSYELPYVMDAGQEGSLPPFPNDVFMVPQ
AAV5    ANNLTSTVQVFTDDDYQLPYVVGNTEGCLPAFPPQVFTLPQ
AAV6    ANNLTSTVQVFSDSEYQLPYVLGSAHQGCLPPFPADVFMIPQ
AAV7    ANNLTSTIQVFSDSEYQLPYVLGSAHQGCLPPFPADVFMIPQ
AAV8    ANNLTSTIQVFTDSEYQLPYVLGSAHQGCLPPFPADVFMIPQ
AAV9    ANNLTSTVQVFTDSDYQLPYVLGSAHEGCLPPFPADVFMIPQ
AAV10   ANNLTSTIQVFTDSEYQLPYVLGSAHQGCLPPFPADVFMIPQ
              380         390         400         410         420
AAV1    YGYLTLN--NGS-QAVGRSSFYCLEYFPSQMLRTGNNFTFSY
AAV2    YGYLTLN--NGS-QAVGRSSFYCLEYFPSQMLRTGNNFTFSY
AAV3A   YGYLTLN--NGS-QAVGRSSFYCLEYFPSQMLRTGNNFQFSY
AAV3B   YGYLTLN--NGS-QAVGRSSFYCLEYFPSQMLRTGNNFQFSY
AAV4    YGYCGLVTGNTSQQQTDRNAFYCLEYFPSQMLRTGNNFEITY
AAV5    YGYATLNRDNTE-NPTERSSFFCLEYFPSKMLRTGNNFEFTY
AAV6    YGYLTLN--NGS-QAVGRSSFYCLEYFPSQMLRTGNNFTFSY
AAV7    YGYLTLN--NGS-QSVGRSSFYCLEYFPSQMLRTGNNFEFSY
AAV8    YGYLTLN--NGS-QAVGRSSFYCLEYFPSQMLRTGNNFQFTY
AAV9    YGYLTLN--DGS-QAVGRSSFYCLEYFPSQMLRTGNNFQFSY
AAV10   YGYLTLN--NGS-QAVGRSSFYCLEYFPSQMLRTGNNFEFSY
              430         440         450         460
AAV1    TFEEVPFHSSYAHSQSLDRLMNPLIDQYLYYLNRTQNQ-SGS
AAV2    TFEDVPFHSSYAHSQSLDRLMNPLIDQYLYYLSRT-NTPSGT
AAV3A   TFEDVPFHSSYAHSQSLDRLMNPLIDQYLYYLNRTQGTTSGT
AAV3B   TFEDVPFHSSYAHSQSLDRLMNPLIDQYLYYLNRTQGTTSGT
AAV4    SFEKVPFHSMYAHSQSLDRLMNPLIDQYLWGLQSTTTGTTLN
AAV5    NFEEVPFHSSFAPSQNLFKLANPLVDQYLYRFVSTNNTGG---
AAV6    TFEDVPFHSSYAHSQSLDRLMNPLIDQYLYYLNRTQNQ-SGS
AAV7    SFEDVPFHSSYAHSQSLDRLMNPLIDQYLYYLARTQSNPGGT
AAV8    TFEDVPFHSSYAHSQSLDRLMNPLIDQYLYYLSRTQTT-GGT
AAV9    EFENVPFHSSYAHSQSLDRLMNPLIDQYLYYLSKTIN---GSG
AAV10   TFEDVPFHSSYAHSQSLDRLMNPLIDQYLYYLSRTQST-GGT
              470         480         490         500
AAV1    AQNKDLLFSRGSPAGMSVQPKNWLPGPCYRQQRVSKTKTDN-
AAV2    TTQSRLQFSQAGASDIRDQSRNWLPGPCYRQQRVSKTSADN-
AAV3A   TNQSRLLFSQAGPQSMSLQARNWLPGPCYRQQRLSKTANDN-
AAV3B   TNQSRLLFSQAGPQSMSLQARNWLPGPCYRQQRLSKTANDN-
AAV4    AGTATTNFTKLRPTNFSNFKKNWLPGPSIKQQGFSKTANQNY
AAV5    -----VQFNKNLAGRYANTYKNWFPGPMGRTQGWNLGSGVNR
AAV6    AQNKDLLFSRGSPAGMSVQPKNWLPGPCYRQQRVSKTKTDN-
AAV7    AGNRELQFYQGGPSTMAEQAKNWLPGPCFRQQRVSKTLDQN-
AAV8    ANTQTLGFSQGGPNTMANQAKNWLPGPCYRQQRVSTTTGQN-
AAV9    QNQQTLKFSVAGPSNMAVQGRNYIPGPSYRQQRVSTTVTQN-
AAV10   QGTQQLLFSQAGPANMSAQAKNWLPGPCYRQQRVSTTLSQN-
```

FIGURE 5 (continued)

```
          510         520         530         540
AAV1    -----NNSNFTWTGASKYNLNGRESIINPGTAMASHKDDEDKF
AAV2    -----NNSEYSWTGATKYHLNGRDSLVNPGPAMASHKDDEEKF
AAV3A   -----NNSNFPWTAASKYHLNGRDSLVNPGPAMASHKDDEEKF
AAV3B   -----NNSNFPWTAASKYHLNGRDSLVNPGPAMASHKDDEEKF
AAV4    KIPATGSDSLIKYETHSTLDGRWSALTPGPPMATAGPADSKF
AAV5    -----ASVSAFATTNRMELEGASYQVPPQPNGMTNNLQGSNT
AAV6    -----NNSNFTWTGASKYNLNGRESIINPGTAMASHKDDKDKF
AAV7    -----NNSNFAWTGATKYHLNGRNSLVNPGVAMATHKDDEDRF
AAV8    -----NNSNFAWTAGTKYHLNGRNSLANPGIAMATHKDDEERF
AAV9    -----NNSEFAWPGASSWALNGRNSLMNPGPAMASHKEGEDRF
AAV10   -----NNSNFAWTGATKYHLNGRDSLVNPGVAMATHKDDEERF 550         560         570         580
AAV1    FPMSGVMIF-GKESAGASNTAL--DNVMITDEEEIKATNPVA
AAV2    FPQSGVLIF-GKQGSEKTNVDI--EKVMITDEEEIRTTNPVA
AAV3A   FPMHGNLIF-GKEGTTASNAEL--DNVMITDEEEIRTTNPVA
AAV3B   FPMHGNLIF-GKEGTTASNAEL--DNVMITDEEEIRTTNPVA
AAV4    --SNSQLIPAGPKQNGNTATVP--GTLIFTSEEELAATNATD
AAV5    YALENTMIFNSQPANPGTTATYLEGNMLITSESETQPVNRVA
AAV6    FPMSGVMIF-GKESAGASNTAL--DNVMITDEEEIKATNPVA
AAV7    FPSSGVLIF-GKTGATNKTTL---ENVLMTNEEEIRPTNPVA
AAV8    FPSNGILIF-GKQNAARDNADY--SDVMLTSEEEIKTTNPVA
AAV9    FPLSGSLIF-GKQGTGRDNVDA--DKVMITNEEEIKTTNPVA
AAV10   FPSSGVLMF-GKQGAGRDNVDY--SSVMLTSEEEIKTTNPVA 590         600         610         620
AAV1    TERFGTVAVNFQSSSTDPATGDVHAMGALPGMVWQDRDVYLQ
AAV2    TEQYGSVSTNLQRGNRQAATADVNTQGVLPGMVWQDRDVYLQ
AAV3A   TEQYGTVANNLQSSNTAPTTGTVNHQGALPGMVWQDRDVYLQ
AAV3B   TEQYGTVANNLQSSNTAPTTRTVNDQGALPGMVWQDRDVYLQ
AAV4    TDMWGNLPGGDQSNSNLPTVDRLTALGAVPGMVWQNRDIYYQ
AAV5    YNVGGQMATNNQSSTTAPATGTYNLQEIVPGSVWMERDVYLQ
AAV6    TERFGTVAVNLQSSSTDPATGDVHVMGALPGMVWQDRDVYLQ
AAV7    TEEYGIVSSNLQAANTAAQTQVVNNQGALPGMVWQNRDVYLQ
AAV8    TEEYGIVADNLQQQNTAPQIGTVNSQGALPGMVWQNRDVYLQ
AAV9    TESYGQVATNHQSAQAQAQTGWVQNQGILPGMVWQDRDVYLQ
AAV10   TEQYGVVADNLQQANTGPIVGNVSQGALPGMVWQNRDVYLQ 630         650         660         670
AAV1    GPIWAKIPHTDGHFHPSPLMGGFGLKNPPPQILIKNTPVPAN
AAV2    GPIWAKIPHTDGHFHPSPLMGGFGLKHPPPQILIKNTPVPAN
AAV3A   GPIWAKIPHTDGHFHPSPLMGGFGLKHPPPQIMIKNTPVPAN
AAV3B   GPIWAKIPHTDGHFHPSPLMGGFGLKHPPPQIMIKNTPVPAN
AAV4    GPIWAKIPHTDGHFHPSPLIGGFGLKHPPPQIFIKNTPVPAN
AAV5    GPIWAKIPETGAHFHPSPAMGGFGLKHPPPMLIKNTPVPGN
AAV6    GPIWAKIPHTDGHFHPSPLMGGFGLKHPPPQILIKNTPVPAN
AAV7    GPIWAKIPHTDGNFHPSPLMGGFGLKHPPPQILIKNTPVPAN
AAV8    GPIWAKIPHTDGNFHPSPLMGGFGLKHPPPQILIKNTPVPAD
AAV9    GPIWAKIPHTDGNFHPSPLMGGFGMKHPPPQILIKNTPVPAD
AAV10   GPIWAKIPHTDGNFHPSPLMGGFGLKHPPPQILIKNTPVPAD
```

FIGURE 5 (continued)

```
              680            690            700            710
AAV1    PPAEFSATKFASFITQYSTGQVSVEIEWELQKENSKRWNPEV
AAV2    PSTTFSAAKFASFITQYSTGQVSVEIEWELQKENSKRWNPEI
AAV3A   PPTTFSPAKFASFITQYSTGQVSVEIEWELQKENSKRWNPEI
AAV3B   PPTTFSPAKFASFITQYSTGQVSVEIEWELQKENSKRWNPEI
AAV4    PATTFSSTPVNSFITQYSTGQVSVQIDWEIQKERSKRWNPEV
AAV5    -ITSFSDVPVSSFITQYSTGQVTVEMEWELKKENSKRWNPEI
AAV6    PPAEFSATKFASFITQYSTGQVSVEIEWELQKENSKRWNPEV
AAV7    PPEVFTPAKFASFITQYSTGQVSVEIEWELQKENSKRWNPEI
AAV8    PPTTFNQSKLNSFITQYSTGQVSVEIEWELQKENSKRWNPEI
AAV9    PPTAFNKDKLNSFITQYSTGQVSVEIEWELQKENSKRWNPEI
AAV10   PPTTFSQAKLASFITQYSTGQVSVEIEWELQKENSKRWNPEI
              720            730            740            750 752
AAV1    QYTSNYAKSANVDFTVDNNGLYTEPRPIGTRYLTRPL*
AAV2    QYTSNYNKSVNVDFTVDTNGVYSEPRPIGTRYLTRNL*
AAV3A   QYTSNYNKSVNVDFTVDTNGVYSEPRPIGTRYLTRNL*
AAV3B   QYTSNYNKSVNVDFTVDTNGVYSEPRPIGTRYLTRNL*
AAV4    QFTSNYGQQNSLLWAPDAAGKYTEPRAIGTRYLTHHL*
AAV5    QYTNNYNDPQFVDFAPDSTGEYRTTRPIGTRYLTRPL*
AAV6    QYTSNYAKSANVDFTVDNNGLYTEPRPIGTRYLTRPL*
AAV7    QYTSNFEKQTGVDFAVDSQGVYSEPRPIGTRYLTRNL*
AAV8    QYTSNYYKSTSVDFAVNTEGVYSEPRPIGTRYLTRNL*
AAV9    QYTSNYYKSNNVEFAVNTEGVYSEPRPIGTRYLTRNL*
AAV10   QYTSNYYKSTNVDFAVNTEGTYSEPRPIGTRYLTRNL*
```

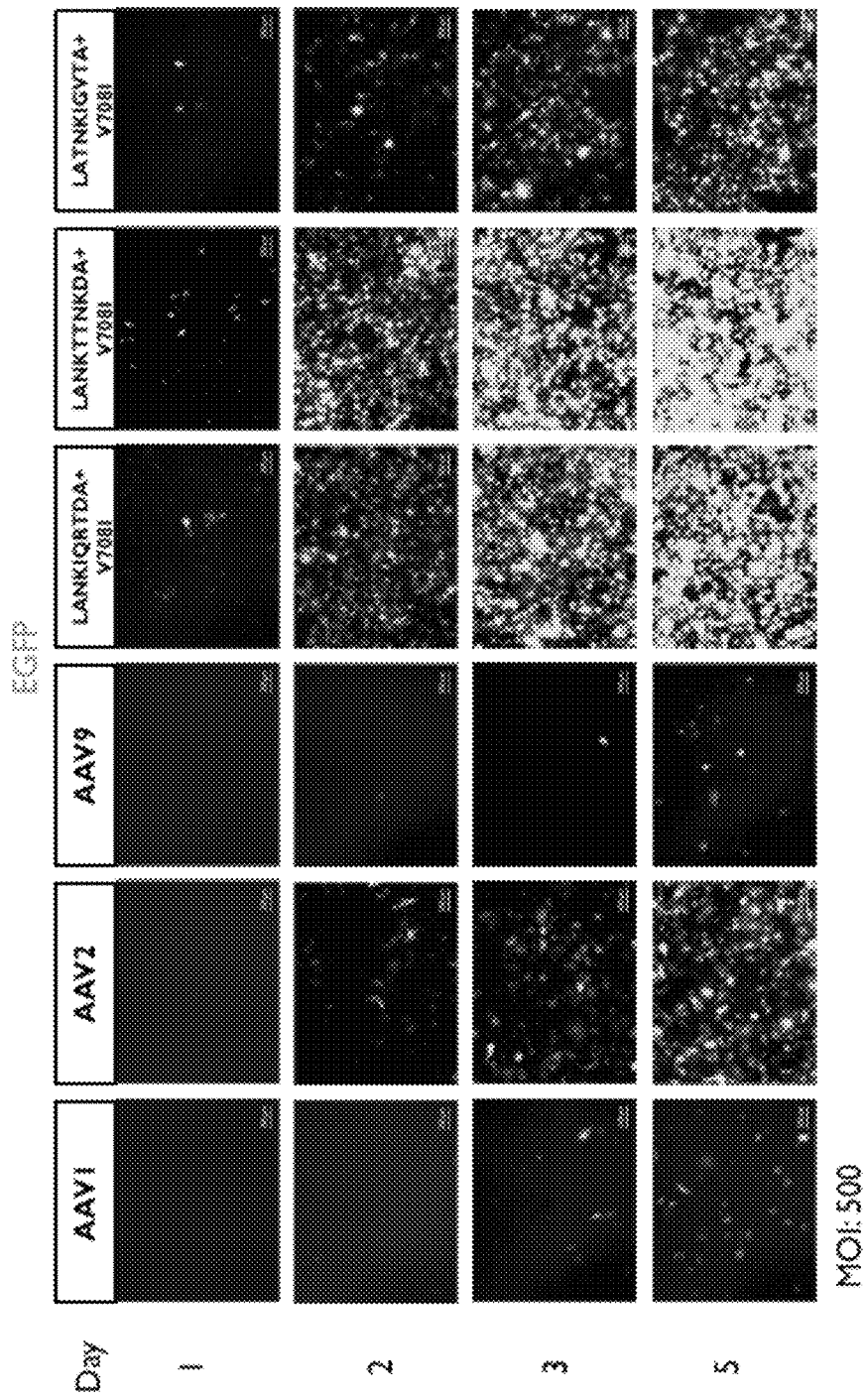

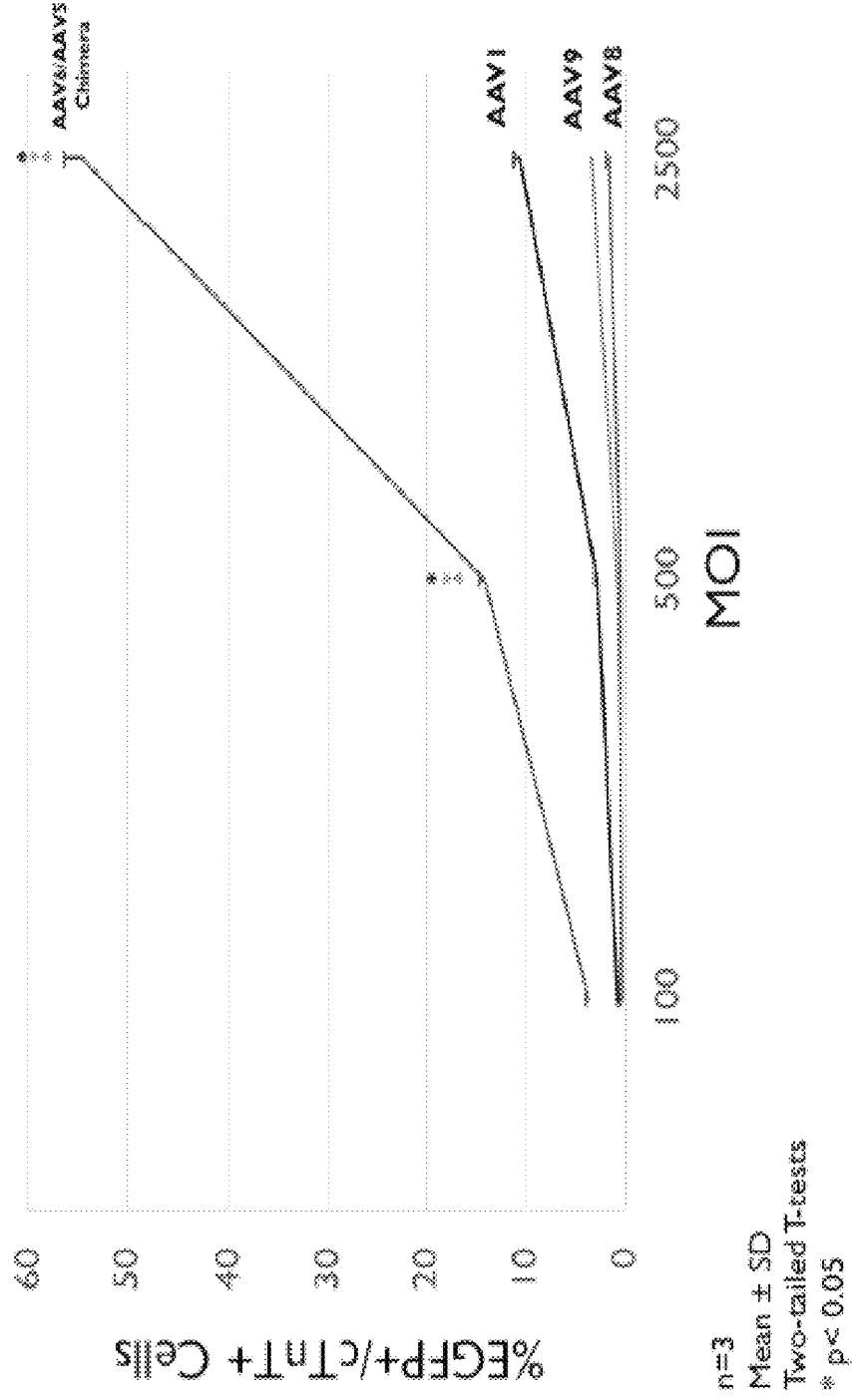

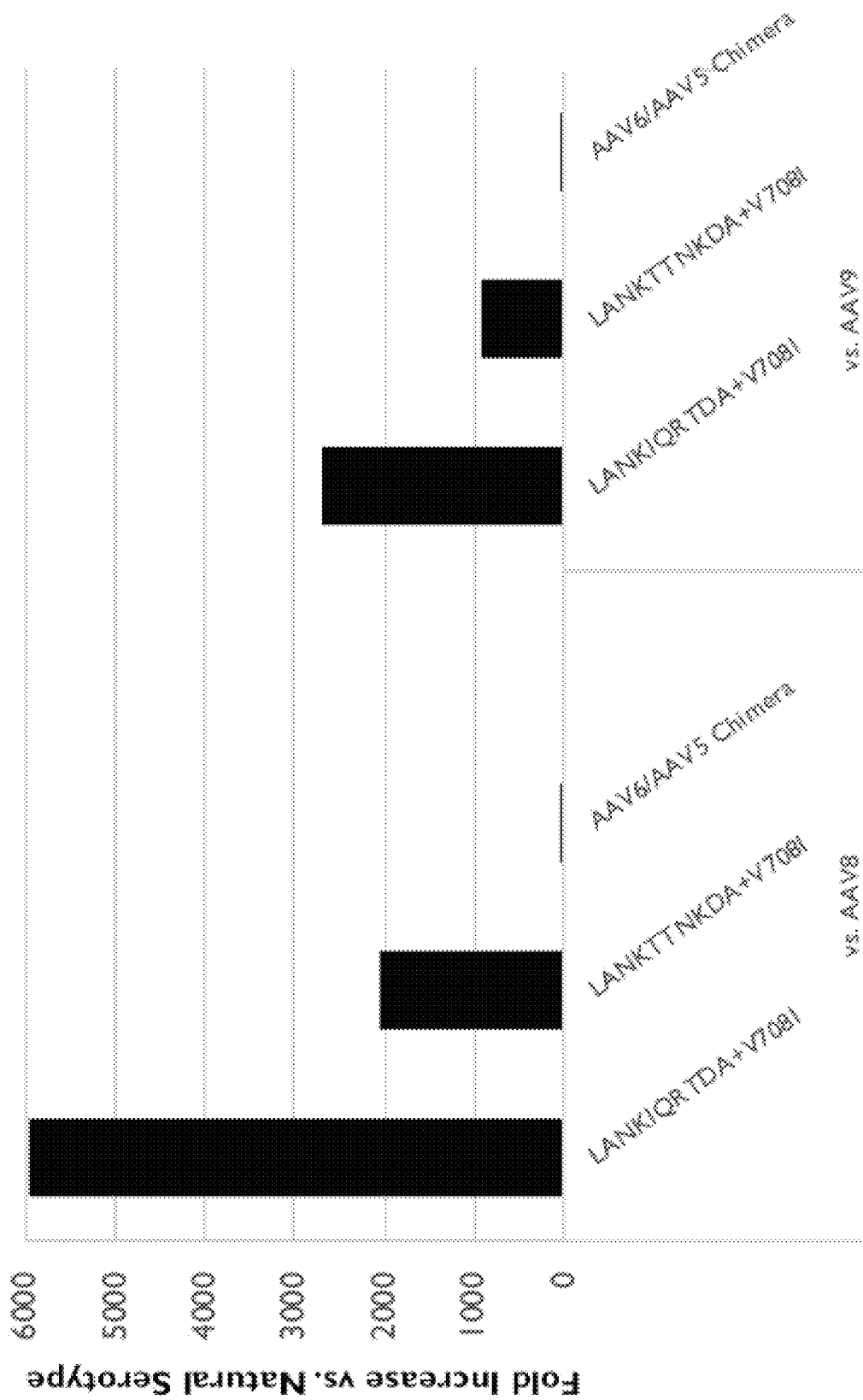

SEQUENCE LISTING

```
<160> NUMBER OF SEQ ID NOS: 69

<210> SEQ ID NO 1
<211> LENGTH: 736
<212> TYPE: PRT
<213> ORGANISM: Adeno-associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480
```

-continued

```
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: adeno-associated virus 2

<400> SEQUENCE: 2

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
                20                  25                  30
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
```

```
Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
530                 535                 540
```

```
Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Adeno-associated virus 3A

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190
```

```
Ala Ala Pro Thr Ser Leu Gly Ser Asn Thr Met Ala Ser Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
            595                 600                 605
```

```
Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Adeno-associated virus 3B

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 734
<212> TYPE: PRT
<213> ORGANISM: Adeno-associated virus 4

<400> SEQUENCE: 5

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320
```

```
Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
    530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
    690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730
```

<210> SEQ ID NO 6
<211> LENGTH: 724
<212> TYPE: PRT
<213> ORGANISM: Adeno-associated virus 5

<400> SEQUENCE: 6

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380
```

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Val Pro Phe His Ser Ser
            405                 410                 415

Phe Ala Pro Ser Gln Asn Leu Phe Lys Leu Ala Asn Pro Leu Val Asp
        420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
            485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
            565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
        610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 7
<211> LENGTH: 736
<212> TYPE: PRT
<213> ORGANISM: Adeno-associated virus 6

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

```
Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Gly Ile Gly
145             150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445
```

```
Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 8
<211> LENGTH: 737
<212> TYPE: PRT
<213> ORGANISM: Adeno-associated virus 7

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gly Ala Lys Thr Ala Pro Ala Lys Lys Arg
            130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                    165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
                    195                 200                 205

Gly Ala Pro Met Ala Asp Asn Glu Gly Ala Asp Gly Val Gly Asn
            210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                    245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                    325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                    485                 490                 495

Gln Asn Asn Asn Ser Asn Phe Ala Trp Thr Gly Ala Thr Lys Tyr His
            500                 505                 510
```

```
Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
        530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
            565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
        690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
            725                 730                 735

Leu

<210> SEQ ID NO 9
<211> LENGTH: 738
<212> TYPE: PRT
<213> ORGANISM: Adeno-associated virus 8

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140
```

-continued

```
Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Gly Ile Leu Ile
            530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
```

```
                565                 570                 575
Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 10
<211> LENGTH: 736
<212> TYPE: PRT
<213> ORGANISM: Adeno-associated virus 9

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
```

```
            195                 200                 205
Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620
```

```
Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 738
<212> TYPE: PRT
<213> ORGANISM: Adeno-associated virus 10

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
```

-continued

```
            260                 265                 270
Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                    325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                    405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
            450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                    485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                    565                 570                 575

Glu Gln Tyr Gly Val Val Ala Asp Asn Leu Gln Gln Ala Asn Thr Gly
                580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                    645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685
```

```
Leu Gln Lys Glu Asn Ser Lys Arg Trp Asn Pro Glu Ile Gln Tyr Thr
    690             695             700

Ser Asn Tyr Tyr Lys Ser Thr Asn Val Asp Phe Ala Val Asn Thr Glu
705             710             715             720

Gly Thr Tyr Ser Glu Pro Arg Pro Ile Gly Thr Arg Tyr Leu Thr Arg
                725             730             735

Asn Leu

<210> SEQ ID NO 12
<211> LENGTH: 738
<212> TYPE: PRT
<213> ORGANISM: Adeno-associated virus rh10

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Gly Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Ser Leu Asn Phe Lys Leu Phe Asn
305                 310                 315                 320
```

```
Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asp Asn Ser Asn Phe Ala Trp Thr Gly Ala Thr Lys Tyr His
        500                 505                 510

Leu Asn Gly Arg Asp Ser Leu Val Asn Pro Gly Val Ala Met Ala Thr
    515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
    595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
        660                 665                 670

Ile Thr Gln Tyr Ser Thr Gly Gln Val Ser Val Glu Ile Glu Trp Glu
    675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
            725                 730                 735
```

Asn Leu

```
<210> SEQ ID NO 13
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 13

Asn Lys Ile Gln Arg Thr Asp
1               5

<210> SEQ ID NO 14
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 14

Asn Lys Thr Thr Asn Lys Asp
1               5

<210> SEQ ID NO 15
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 15

Thr Asn Lys Ile Gly Val Thr
1               5

<210> SEQ ID NO 16
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 16

Gly Asn Leu Thr Lys Gly Asn
1               5

<210> SEQ ID NO 17
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 17

Asn Thr Val Lys Leu Ser Thr
1               5

<210> SEQ ID NO 18
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 18

Ser Asn Thr Val Lys Ala Ile
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 19

Ala Ser Asn Ile Thr Lys Ala
1               5

<210> SEQ ID NO 20
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 20

Asp Asn Thr Val Thr Arg Ser
1               5

<210> SEQ ID NO 21
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 21

Asn Lys Ile Ser Ala Lys Asp
1               5

<210> SEQ ID NO 22
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 22

Asn Gln Asp Tyr Thr Lys Thr
1               5

<210> SEQ ID NO 23
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 23

Gln Ala Asp Thr Thr Lys Asn
1               5

<210> SEQ ID NO 24
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 24

Thr Asn Arg Thr Ser Pro Asp
1               5
```

<210> SEQ ID NO 25
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 25

Ser Asn Thr Thr Gln Lys Thr
1               5

<210> SEQ ID NO 26
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 26

Ala Ser Asp Ser Thr Lys Ala
1               5

<210> SEQ ID NO 27
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 27

Leu Ala Asn Lys Ile Gln Arg Thr Asp Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 28

Leu Ala Asn Lys Thr Thr Asn Lys Asp Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 29

Leu Ala Thr Asn Lys Ile Gly Val Thr Ala
1               5                   10

<210> SEQ ID NO 30
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 30

Leu Ala Gly Asn Leu Thr Lys Gly Asn Ala
1               5                   10

```
<210> SEQ ID NO 31
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 31

Leu Ala Asn Thr Val Lys Leu Ser Thr Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 32

Leu Ala Ser Asn Thr Val Lys Ala Ile Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 33

Leu Ala Ala Ser Asn Ile Thr Lys Ala Ala
1               5                   10

<210> SEQ ID NO 34
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 34

Leu Ala Asp Asn Thr Val Thr Arg Ser Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 35

Leu Ala Asn Lys Ile Ser Ala Lys Asp Ala
1               5                   10

<210> SEQ ID NO 36
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 36

Leu Ala Asn Gln Asp Tyr Thr Lys Thr Ala
1               5                   10

<210> SEQ ID NO 37
```

```
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 37

Leu Ala Thr Asn Lys Ile Gly Val Thr Ser
1               5                   10

<210> SEQ ID NO 38
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 38

Leu Ala Thr Asn Lys Ile Gly Val Thr Ala
1               5                   10

<210> SEQ ID NO 39
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 39

Leu Ala Gln Ala Asp Thr Thr Lys Asn Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 40

Leu Ala Thr Asn Arg Thr Ser Pro Asp Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 41

Leu Ala Ser Asn Thr Thr Gln Lys Thr Ala
1               5                   10

<210> SEQ ID NO 42
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 42

Leu Ala Ala Ser Asp Ser Thr Lys Ala Ala
1               5                   10

<210> SEQ ID NO 43
<211> LENGTH: 745
```

```
<212> TYPE: PRT
<213> ORGANISM: Artificial Sequence
<220> FEATURE:
<223> OTHER INFORMATION: variant AAV capsid

<400> SEQUENCE: 43
```

| | | | | | | | | | | | | |
|---|---|---|---|---|---|---|---|---|---|---|---|---|
| Met | Ala | Ala | Asp | Gly | Tyr | Leu | Pro | Asp | Trp | Leu | Glu | Asp | Thr | Leu | Ser |

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
    355                 360                 365

Val Phe Met Val Pro Gln Tyr Gly Tyr Leu Thr Leu Asn Asn Gly Ser
    370                 375                 380

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Ile
            580                 585                 590

Gln Arg Thr Asp Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 44
<211> LENGTH: 745
<212> TYPE: PRT
<213> ORGANISM: Artificial Sequence
<220> FEATURE:
<223> OTHER INFORMATION: variant AAV capsid

<400> SEQUENCE: 44
```

-continued

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Lys Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg 420                 425                 430
Leu Met Asn Pro Leu Ile Asp Gln Tyr Leu Tyr Tyr Leu Ser Arg Thr
            435                 440                 445

Asp Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Ser Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Ile
            580                 585                 590

Gln Arg Thr Asp Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Val Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Gln
            740                 745

<210> SEQ ID NO 45
<211> LENGTH: 745
<212> TYPE: PRT
<213> ORGANISM: Artificial Sequence
<220> FEATURE:
<223> OTHER INFORMATION: variant AAV capsid

<400> SEQUENCE: 45

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro

-continued

```
                35                  40                  45
Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460
```

```
Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Ile
            580                 585                 590

Gln Arg Thr Asp Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 46
<211> LENGTH: 745
<212> TYPE: PRT
<213> ORGANISM: Artificial Sequence
<220> FEATURE:
<223> OTHER INFORMATION: variant AAV capsid

<400> SEQUENCE: 46

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80
```

```
Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495
```

```
Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Thr Asn Lys
            580                 585                 590

Ile Gly Val Thr Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 47
<211> LENGTH: 745
<212> TYPE: PRT
<213> ORGANISM: Artificial Sequence
<220> FEATURE:
<223> OTHER INFORMATION: variant AAV capsid

<400> SEQUENCE: 47

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110
```

-continued

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys

```
                    530                 535                 540
Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                    565                 570                 575

Gly Ser Val Ser Thr Asn Leu Gln Arg Gly Asn Leu Ala Thr Asn Lys
                    580                 585                 590

Ile Gly Val Thr Ala Arg Gln Ala Ala Thr Ala Asp Val Asn Thr Gln
                    595                 600                 605

Gly Val Leu Pro Gly Met Val Trp Gln Asp Arg Asp Val Tyr Leu Gln
                    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                    645                 650                 655

Leu Ile Lys Asn Thr Pro Val Pro Ala Asn Pro Ser Thr Thr Phe Ser
                    660                 665                 670

Ala Ala Lys Phe Ala Ser Phe Ile Thr Gln Tyr Ser Thr Gly Gln Val
                    675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                    725                 730                 735

Gly Thr Arg Tyr Leu Thr Arg Asn Leu
                    740                 745

<210> SEQ ID NO 48
<211> LENGTH: 745
<212> TYPE: PRT
<213> ORGANISM: Artificial Sequence
<220> FEATURE:
<223> OTHER INFORMATION: variant AAV capsid

<400> SEQUENCE: 48

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
            50                  55                  60

Val Asn Glu Ala Asp Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
            130                 135                 140

Pro Val Glu His Ser Pro Val Glu Pro Asp Ser Ser Ser Gly Thr Gly
```

-continued

```
            145                 150                 155                 160
Lys Ala Gly Gln Gln Pro Ala Arg Lys Arg Leu Asn Phe Gly Gln Thr
                    165                 170                 175
Gly Asp Ala Asp Ser Val Pro Asp Pro Gln Pro Leu Gly Gln Pro Pro
                180                 185                 190
Ala Ala Pro Ser Gly Leu Gly Thr Asn Thr Met Ala Thr Gly Ser Gly
                195                 200                 205
Ala Pro Met Ala Asp Asn Asn Glu Gly Ala Asp Gly Val Gly Asn Ser
            210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                    245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
            290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                    325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                    405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
                435                 440                 445
Asn Thr Pro Ser Gly Thr Thr Thr Gln Ser Arg Leu Gln Phe Ser Gln
                450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                    485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
                515                 520                 525
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                    565                 570                 575
```

```
Gly Ser Val Ser Thr Asn Leu Gln Arg Gly Asn Leu Ala Asn Lys Thr
            580                 585                 590

Thr Asn Lys Asp Ala Arg Gln Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
            725                 730                 735

Gly Thr Arg Tyr Leu Thr Arg Asn Leu
            740                 745

<210> SEQ ID NO 49
<211> LENGTH: 745
<212> TYPE: PRT
<213> ORGANISM: Artificial Sequence
<220> FEATURE:
<223> OTHER INFORMATION: variant AAV capsid

<400> SEQUENCE: 49

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
            50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
            130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
            180                 185                 190
```

```
Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Lys Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asp Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Ser Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Thr
            580                 585                 590

Thr Asn Lys Asp Ala Arg Gln Ala Ala Thr Ala Asp Val Asn Thr Gln
            595                 600                 605
```

Gly Val Leu Pro Gly Met Val Trp Gln Asp Arg Asp Val Tyr Leu Gln
            610             615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Val Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Gln
                740                 745

<210> SEQ ID NO 50
<211> LENGTH: 745
<212> TYPE: PRT
<213> ORGANISM: Artificial Sequence
<220> FEATURE:
<223> OTHER INFORMATION: variant AAV capsid

<400> SEQUENCE: 50

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Thr
            580                 585                 590

Thr Asn Lys Asp Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
```

```
                    645                 650                 655
Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
        690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 51
<211> LENGTH: 745
<212> TYPE: PRT
<213> ORGANISM: Artificial Sequence
<220> FEATURE:
<223> OTHER INFORMATION: variant AAV capsid

<400> SEQUENCE: 51

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65              70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
```

```
              260                 265                 270
Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Gly Asn Leu
            580                 585                 590

Thr Lys Gly Asn Ala Arg Gln Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685
```

```
Ser Val Glu Ile Glu Trp Glu Leu Gln Lys Glu Asn Ser Lys Arg Trp
    690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 52
<211> LENGTH: 745
<212> TYPE: PRT
<213> ORGANISM: Artificial Sequence
<220> FEATURE:
<223> OTHER INFORMATION: variant AAV capsid

<400> SEQUENCE: 52

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Arg
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Thr Val
                580                 585                 590

Lys Leu Ser Thr Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Val Asn Val
705                 710                 715                 720
```

```
Asp Phe Thr Val Asp Thr Asn Gly Val Tyr Ser Glu Pro Arg Pro Ile
                725                 730                 735
Gly Thr Arg Tyr Leu Thr Arg Asn Leu
        740                 745

<210> SEQ ID NO 53
<211> LENGTH: 745
<212> TYPE: PRT
<213> ORGANISM: Artificial Sequence
<220> FEATURE:
<223> OTHER INFORMATION: variant AAV capsid

<400> SEQUENCE: 53

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

-continued

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ser Asn Thr
            580                 585                 590

Val Lys Ala Ile Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745
```

```
<210> SEQ ID NO 54
<211> LENGTH: 745
<212> TYPE: PRT
<213> ORGANISM: Artificial Sequence
<220> FEATURE:
<223> OTHER INFORMATION: variant AAV capsid

<400> SEQUENCE: 54

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
```

```
            370                 375                 380
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ala Ser Asn
                580                 585                 590

Ile Thr Lys Ala Ala Arg Gln Ala Ala Thr Ala Asp Val Asn Thr Gln
                595                 600                 605

Gly Val Leu Pro Gly Met Val Trp Gln Asp Arg Asp Val Tyr Leu Gln
                610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
                675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
                740                 745

<210> SEQ ID NO 55
<211> LENGTH: 745
<212> TYPE: PRT
<213> ORGANISM: Artificial Sequence
<220> FEATURE:
<223> OTHER INFORMATION: variant AAV capsid
```

```
<400> SEQUENCE: 55

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415
```

```
Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asp Asn Thr
            580                 585                 590

Val Thr Arg Ser Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 56
<211> LENGTH: 745
<212> TYPE: PRT
<213> ORGANISM: Artificial Sequence
<220> FEATURE:
<223> OTHER INFORMATION: variant AAV capsid

<400> SEQUENCE: 56

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30
```

```
Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65              70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445
```

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Ile
            580                 585                 590

Ser Ala Lys Asp Ala Arg Gln Ala Ala Thr Ala Asp Val Asn Thr Gln
595                 600                 605

Gly Val Leu Pro Gly Met Val Trp Gln Asp Arg Asp Val Tyr Leu Gln
610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 57
<211> LENGTH: 745
<212> TYPE: PRT
<213> ORGANISM: Artificial Sequence
<220> FEATURE:
<223> OTHER INFORMATION: variant AAV capsid

<400> SEQUENCE: 57

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
            50                  55                  60

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
```

```
                    485                 490                 495
Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Gln Asp
            580                 585                 590

Tyr Thr Lys Thr Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
        610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
        690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 58
<211> LENGTH: 745
<212> TYPE: PRT
<213> ORGANISM: Artificial Sequence
<220> FEATURE:
<223> OTHER INFORMATION: variant AAV capsid

<400> SEQUENCE: 58

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
```

```
                100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
        130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
```

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Gln Ala Asp
                580                 585                 590

Thr Thr Lys Asn Ala Arg Gln Ala Thr Ala Asp Val Asn Thr Gln
                595                 600                 605

Gly Val Leu Pro Gly Met Val Trp Gln Asp Arg Asp Val Tyr Leu Gln
                610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
                675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
                740                 745

<210> SEQ ID NO 59
<211> LENGTH: 745
<212> TYPE: PRT
<213> ORGANISM: Artificial Sequence
<220> FEATURE:
<223> OTHER INFORMATION: variant AAV capsid

<400> SEQUENCE: 59

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
        180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560
```

```
Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Thr Asn Arg
            580                 585                 590

Thr Ser Pro Asp Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
            645                 650                 655

Leu Ile Lys Asn Thr Pro Val Pro Ala Asn Pro Ser Thr Thr Phe Ser
        660                 665                 670

Ala Ala Lys Phe Ala Ser Phe Ile Thr Gln Tyr Ser Thr Gly Gln Val
    675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Ile Asn Val
705                 710                 715                 720

Asp Phe Thr Val Asp Thr Asn Gly Val Tyr Ser Glu Pro Arg Pro Ile
            725                 730                 735

Gly Thr Arg Tyr Leu Thr Arg Asn Leu
            740                 745

<210> SEQ ID NO 60
<211> LENGTH: 745
<212> TYPE: PRT
<213> ORGANISM: Artificial Sequence
<220> FEATURE:
<223> OTHER INFORMATION: variant AAV capsid

<400> SEQUENCE: 60

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175
```

```
Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Leu Ala Ser Asn Thr
            580                 585                 590

Thr Gln Lys Thr Ala Arg Gln Ala Ala Thr Ala Asp Val Asn Thr Gln
```

```
                595                 600                 605
Gly Val Leu Pro Gly Met Val Trp Gln Asp Arg Asp Val Tyr Leu Gln
            610                 615                 620
Gly Pro Ile Trp Ala Lys Ile Pro His Thr Asp Gly His Phe His Pro
625                 630                 635                 640
Ser Pro Leu Met Gly Phe Gly Leu Lys His Pro Pro Gln Ile
                645                 650                 655
Leu Ile Lys Asn Thr Pro Val Pro Ala Asn Pro Ser Thr Thr Phe Ser
            660                 665                 670
Ala Ala Lys Phe Ala Ser Phe Ile Thr Gln Tyr Ser Thr Gly Gln Val
            675                 680                 685
Ser Val Glu Ile Glu Trp Glu Leu Gln Lys Glu Asn Ser Lys Arg Trp
            690                 695                 700
Asn Pro Glu Ile Gln Tyr Thr Ser Asn Tyr Asn Lys Ser Val Asn Val
705                 710                 715                 720
Asp Phe Thr Val Asp Thr Asn Gly Val Tyr Ser Glu Pro Arg Pro Ile
                725                 730                 735
Gly Thr Arg Tyr Leu Thr Arg Asn Leu
            740                 745

<210> SEQ ID NO 61
<211> LENGTH: 745
<212> TYPE: PRT
<213> ORGANISM: Artificial Sequence
<220> FEATURE:
<223> OTHER INFORMATION: variant AAV capsid

<400> SEQUENCE: 61

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65              70                  75                  80
Arg Gln Leu Asp Ser Gly Asp Asn Pro Tyr Leu Lys Tyr Asn His Ala
            85                  90                  95
Asp Ala Glu Phe Gln Glu Arg Leu Lys Glu Asp Thr Ser Phe Gly Gly
        100                 105                 110
Asn Leu Gly Arg Ala Val Phe Gln Ala Lys Lys Arg Val Leu Glu Pro
    115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
            165                 170                 175
Gly Asp Ala Asp Ser Val Pro Asp Pro Gln Pro Leu Gly Gln Pro Pro
        180                 185                 190
Ala Ala Pro Ser Gly Leu Gly Thr Asn Thr Met Ala Thr Gly Ser Gly
    195                 200                 205
Ala Pro Met Ala Asp Asn Asn Glu Gly Ala Asp Gly Val Gly Asn Ser
```

-continued

```
                210                 215                 220
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
                290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ala Ser Asp
                580                 585                 590

Ser Thr Lys Ala Ala Arg Gln Ala Ala Thr Ala Asp Val Asn Thr Gln
                595                 600                 605

Gly Val Leu Pro Gly Met Val Trp Gln Asp Arg Asp Val Tyr Leu Gln
                610                 615                 620

Gly Pro Ile Trp Ala Lys Ile Pro His Thr Asp Gly His Phe His Pro
625                 630                 635                 640
```

```
Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
            725                 730                 735

Gly Thr Arg Tyr Leu Thr Arg Asn Leu
            740                 745

<210> SEQ ID NO 62
<211> LENGTH: 725
<212> TYPE: PRT
<213> ORGANISM: Artificial Sequence
<220> FEATURE:
<223> OTHER INFORMATION: Variant AAV capsid chimera

<400> SEQUENCE: 62

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Ile Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255
```

-continued

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

```
Glu Trp Glu Leu Lys Lys Glu Asn Ser Lys Arg Trp Asn Pro Glu Ile
            675                 680                 685

Gln Tyr Thr Asn Asn Tyr Asn Asp Pro Gln Phe Val Asp Phe Ala Pro
        690                 695                 700

Asp Ser Thr Gly Glu Tyr Arg Thr Thr Arg Pro Ile Gly Thr Arg Tyr
705                 710                 715                 720

Leu Thr Arg Pro Leu
            725

<210> SEQ ID NO 63
<211> LENGTH: 725
<212> TYPE: PRT
<213> ORGANISM: Artificial Sequence
<220> FEATURE:
<223> OTHER INFORMATION: Variant AAV capsid chimera

<400> SEQUENCE: 63

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Thr Gly Lys Arg
    130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Ile Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300
```

```
Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
385                 390                 395                 400

Asn Asn Phe Glu Phe Thr Tyr Asn Phe Glu Glu Val Pro Phe His Ser
                405                 410                 415

Ser Phe Ala Pro Ser Gln Asn Leu Phe Lys Leu Ala Asn Pro Leu Val
            420                 425                 430

Asp Gln Tyr Leu Tyr Arg Phe Val Ser Thr Asn Asn Thr Gly Gly Val
        435                 440                 445

Gln Phe Asn Lys Asn Leu Ala Gly Arg Tyr Ala Asn Thr Tyr Lys Asn
    450                 455                 460

Trp Phe Pro Gly Pro Met Gly Arg Thr Gln Gly Trp Asn Leu Gly Ser
465                 470                 475                 480

Gly Val Asn Arg Ala Ser Val Ser Ala Phe Thr Thr Thr Asn Arg Met
                485                 490                 495

Glu Leu Glu Gly Ala Ser Tyr Gln Val Pro Pro Gln Pro Asn Gly Met
            500                 505                 510

Thr Asn Asn Leu Gln Gly Ser Asn Thr Tyr Ala Leu Glu Asn Thr Met
        515                 520                 525

Ile Phe Asn Ser Gln Pro Ala Asn Pro Gly Thr Thr Ala Thr Tyr Leu
    530                 535                 540

Glu Gly Asn Met Leu Ile Thr Ser Glu Ser Glu Thr Gln Pro Val Asn
545                 550                 555                 560

Arg Val Ala Tyr Asn Val Gly Gly Gln Met Ala Thr Asn Asn Gln Ser
                565                 570                 575

Ser Thr Thr Ala Pro Thr Thr Gly Thr Tyr Asn Leu Gln Glu Ile Val
            580                 585                 590

Pro Gly Ser Val Trp Met Glu Arg Asp Val Tyr Leu Gln Gly Pro Ile
        595                 600                 605

Trp Ala Lys Ile Pro Glu Thr Gly Ala His Phe His Pro Ser Pro Ala
    610                 615                 620

Met Gly Gly Phe Gly Leu Lys His Pro Pro Met Met Leu Ile Lys
625                 630                 635                 640

Asn Thr Pro Val Pro Gly Asn Ile Thr Ser Phe Ser Asp Val Pro Val
                645                 650                 655

Ser Ser Phe Ile Thr Gln Tyr Ser Thr Gly Gln Val Thr Val Glu Met
            660                 665                 670

Glu Trp Glu Leu Lys Lys Glu Asn Ser Lys Arg Trp Asn Pro Glu Ile
        675                 680                 685

Gln Tyr Thr Asn Asn Tyr Asp Pro Gln Phe Val Asp Phe Ala Pro
    690                 695                 700

Asp Ser Thr Gly Glu Tyr Arg Thr Thr Arg Pro Ile Gly Thr Arg Tyr
705                 710                 715                 720

Leu Thr Arg Pro Leu
```

<210> SEQ ID NO 64
<211> LENGTH: 3685
<212> TYPE: PRT
<213> ORGANISM: Homo sapiens

<400> SEQUENCE: 64

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365
```

```
Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
```

-continued

```
                785                 790                 795                 800
       Ile Lys Gln Ala Ser Glu Gln Leu Asn Ser Arg Trp Ile Glu Phe Cys
                       805                 810                 815

Gln Leu Leu Ser Glu Arg Leu Asn Trp Leu Glu Tyr Gln Asn Asn Ile
                       820                 825                 830

Ile Ala Phe Tyr Asn Gln Leu Gln Gln Leu Glu Gln Met Thr Thr Thr
                       835                 840                 845

Ala Glu Asn Trp Leu Lys Ile Gln Pro Thr Thr Pro Ser Glu Pro Thr
       850                 855                 860

Ala Ile Lys Ser Gln Leu Lys Ile Cys Lys Asp Glu Val Asn Arg Leu
       865                 870                 875                 880

Ser Gly Leu Gln Pro Gln Ile Glu Arg Leu Lys Ile Gln Ser Ile Ala
                       885                 890                 895

Leu Lys Glu Lys Gly Gln Gly Pro Met Phe Leu Asp Ala Asp Phe Val
                       900                 905                 910

Ala Phe Thr Asn His Phe Lys Gln Val Phe Ser Asp Val Gln Ala Arg
                       915                 920                 925

Glu Lys Glu Leu Gln Thr Ile Phe Asp Thr Leu Pro Pro Met Arg Tyr
                       930                 935                 940

Gln Glu Thr Met Ser Ala Ile Arg Thr Trp Val Gln Ser Glu Thr
       945                 950                 955                 960

Lys Leu Ser Ile Pro Gln Leu Ser Val Thr Asp Tyr Glu Ile Met Glu
                       965                 970                 975

Gln Arg Leu Gly Glu Leu Gln Ala Leu Gln Ser Ser Leu Gln Glu Gln
                       980                 985                 990

Gln Ser Gly Leu Tyr Tyr Leu Ser Thr Thr Val Lys Glu Met Ser Lys
                       995                 1000                1005

Lys Ala Pro Ser Glu Ile Ser Arg Lys Tyr Gln Ser Glu Phe Glu
                       1010                1015                1020

Glu Ile Glu Gly Arg Trp Lys Lys Leu Ser Ser Gln Leu Val Glu
                       1025                1030                1035

His Cys Gln Lys Leu Glu Glu Gln Met Asn Lys Leu Arg Lys Ile
                       1040                1045                1050

Gln Asn His Ile Gln Thr Leu Lys Lys Trp Met Ala Glu Val Asp
                       1055                1060                1065

Val Phe Leu Lys Glu Glu Trp Pro Ala Leu Gly Asp Ser Glu Ile
                       1070                1075                1080

Leu Lys Lys Gln Leu Lys Gln Cys Arg Leu Leu Val Ser Asp Ile
                       1085                1090                1095

Gln Thr Ile Gln Pro Ser Leu Asn Ser Val Asn Glu Gly Gly Gln
                       1100                1105                1110

Lys Ile Lys Asn Glu Ala Glu Pro Glu Phe Ala Ser Arg Leu Glu
                       1115                1120                1125

Thr Glu Leu Lys Glu Leu Asn Thr Gln Trp Asp His Met Cys Gln
                       1130                1135                1140

Gln Val Tyr Ala Arg Lys Glu Ala Leu Lys Gly Gly Leu Glu Lys
                       1145                1150                1155

Thr Val Ser Leu Gln Lys Asp Leu Ser Glu Met His Glu Trp Met
                       1160                1165                1170

Thr Gln Ala Glu Glu Glu Tyr Leu Glu Arg Asp Phe Glu Tyr Lys
                       1175                1180                1185

Thr Pro Asp Glu Leu Gln Lys Ala Val Glu Glu Met Lys Arg Ala
                       1190                1195                1200
```

```
Lys Glu Glu Ala Gln Gln Lys Glu Ala Lys Val Lys Leu Leu Thr
    1205              1210              1215

Glu Ser Val Asn Ser Val Ile Ala Gln Ala Pro Pro Val Ala Gln
    1220              1225              1230

Glu Ala Leu Lys Lys Glu Leu Glu Thr Leu Thr Thr Asn Tyr Gln
    1235              1240              1245

Trp Leu Cys Thr Arg Leu Asn Gly Lys Cys Lys Thr Leu Glu Glu
    1250              1255              1260

Val Trp Ala Cys Trp His Glu Leu Leu Ser Tyr Leu Glu Lys Ala
    1265              1270              1275

Asn Lys Trp Leu Asn Glu Val Glu Phe Lys Leu Lys Thr Thr Glu
    1280              1285              1290

Asn Ile Pro Gly Gly Ala Glu Glu Ile Ser Glu Val Leu Asp Ser
    1295              1300              1305

Leu Glu Asn Leu Met Arg His Ser Glu Asp Asn Pro Asn Gln Ile
    1310              1315              1320

Arg Ile Leu Ala Gln Thr Leu Thr Asp Gly Gly Val Met Asp Glu
    1325              1330              1335

Leu Ile Asn Glu Glu Leu Glu Thr Phe Asn Ser Arg Trp Arg Glu
    1340              1345              1350

Leu His Glu Glu Ala Val Arg Arg Gln Lys Leu Leu Glu Gln Ser
    1355              1360              1365

Ile Gln Ser Ala Gln Glu Thr Glu Lys Ser Leu His Leu Ile Gln
    1370              1375              1380

Glu Ser Leu Thr Phe Ile Asp Lys Gln Leu Ala Ala Tyr Ile Ala
    1385              1390              1395

Asp Lys Val Asp Ala Ala Gln Met Pro Gln Glu Ala Gln Lys Ile
    1400              1405              1410

Gln Ser Asp Leu Thr Ser His Glu Ile Ser Leu Glu Glu Met Lys
    1415              1420              1425

Lys His Asn Gln Gly Lys Glu Ala Ala Gln Arg Val Leu Ser Gln
    1430              1435              1440

Ile Asp Val Ala Gln Lys Lys Leu Gln Asp Val Ser Met Lys Phe
    1445              1450              1455

Arg Leu Phe Gln Lys Pro Ala Asn Phe Glu Gln Arg Leu Gln Glu
    1460              1465              1470

Ser Lys Met Ile Leu Asp Glu Val Lys Met His Leu Pro Ala Leu
    1475              1480              1485

Glu Thr Lys Ser Val Glu Gln Glu Val Val Gln Ser Gln Leu Asn
    1490              1495              1500

His Cys Val Asn Leu Tyr Lys Ser Leu Ser Glu Val Lys Ser Glu
    1505              1510              1515

Val Glu Met Val Ile Lys Thr Gly Arg Gln Ile Val Gln Lys Lys
    1520              1525              1530

Gln Thr Glu Asn Pro Lys Glu Leu Asp Glu Arg Val Thr Ala Leu
    1535              1540              1545

Lys Leu His Tyr Asn Glu Leu Gly Ala Lys Val Thr Glu Arg Lys
    1550              1555              1560

Gln Gln Leu Glu Lys Cys Leu Lys Leu Ser Arg Lys Met Arg Lys
    1565              1570              1575

Glu Met Asn Val Leu Thr Glu Trp Leu Ala Ala Thr Asp Met Glu
    1580              1585              1590
```

```
Leu Thr Lys Arg Ser Ala Val Glu Gly Met Pro Ser Asn Leu Asp
1595                1600                1605

Ser Glu Val Ala Trp Gly Lys Ala Thr Gln Lys Glu Ile Glu Lys
1610                1615                1620

Gln Lys Val His Leu Lys Ser Ile Thr Glu Val Gly Glu Ala Leu
1625                1630                1635

Lys Thr Val Leu Gly Lys Lys Glu Thr Leu Val Glu Asp Lys Leu
1640                1645                1650

Ser Leu Leu Asn Ser Asn Trp Ile Ala Val Thr Ser Arg Ala Glu
1655                1660                1665

Glu Trp Leu Asn Leu Leu Leu Glu Tyr Gln Lys His Met Glu Thr
1670                1675                1680

Phe Asp Gln Asn Val Asp His Ile Thr Lys Trp Ile Ile Gln Ala
1685                1690                1695

Asp Thr Leu Leu Asp Glu Ser Glu Lys Lys Lys Pro Gln Gln Lys
1700                1705                1710

Glu Asp Val Leu Lys Arg Leu Lys Ala Glu Leu Asn Asp Ile Arg
1715                1720                1725

Pro Lys Val Asp Ser Thr Arg Asp Gln Ala Ala Asn Leu Met Ala
1730                1735                1740

Asn Arg Gly Asp His Cys Arg Lys Leu Val Glu Pro Gln Ile Ser
1745                1750                1755

Glu Leu Asn His Arg Phe Ala Ala Ile Ser His Arg Ile Lys Thr
1760                1765                1770

Gly Lys Ala Ser Ile Pro Leu Lys Glu Leu Glu Gln Phe Asn Ser
1775                1780                1785

Asp Ile Gln Lys Leu Leu Glu Pro Leu Glu Ala Glu Ile Gln Gln
1790                1795                1800

Gly Val Asn Leu Lys Glu Glu Asp Phe Asn Lys Asp Met Asn Glu
1805                1810                1815

Asp Asn Glu Gly Thr Val Lys Glu Leu Leu Gln Arg Gly Asp Asn
1820                1825                1830

Leu Gln Gln Arg Ile Thr Asp Glu Arg Lys Arg Glu Glu Ile Lys
1835                1840                1845

Ile Lys Gln Gln Leu Leu Gln Thr Lys His Asn Ala Leu Lys Asp
1850                1855                1860

Leu Arg Ser Gln Arg Arg Lys Lys Ala Leu Glu Ile Ser His Gln
1865                1870                1875

Trp Tyr Gln Tyr Lys Arg Gln Ala Asp Asp Leu Leu Lys Cys Leu
1880                1885                1890

Asp Asp Ile Glu Lys Lys Leu Ala Ser Leu Pro Glu Pro Arg Asp
1895                1900                1905

Glu Arg Lys Ile Lys Glu Ile Asp Arg Glu Leu Gln Lys Lys Lys
1910                1915                1920

Glu Glu Leu Asn Ala Val Arg Arg Gln Ala Glu Gly Leu Ser Glu
1925                1930                1935

Asp Gly Ala Ala Met Ala Val Glu Pro Thr Gln Ile Gln Leu Ser
1940                1945                1950

Lys Arg Trp Arg Glu Ile Glu Ser Lys Phe Ala Gln Phe Arg Arg
1955                1960                1965

Leu Asn Phe Ala Gln Ile His Thr Val Arg Glu Glu Thr Met Met
1970                1975                1980

Val Met Thr Glu Asp Met Pro Leu Glu Ile Ser Tyr Val Pro Ser
```

```
               1985                1990                1995

Thr Tyr Leu Thr Glu Ile Thr His Val Ser Gln Ala Leu Leu Glu
        2000            2005            2010

Val Glu Gln Leu Leu Asn Ala Pro Asp Leu Cys Ala Lys Asp Phe
        2015            2020            2025

Glu Asp Leu Phe Lys Gln Glu Glu Ser Leu Lys Asn Ile Lys Asp
        2030            2035            2040

Ser Leu Gln Gln Ser Ser Gly Arg Ile Asp Ile Ile His Ser Lys
        2045            2050            2055

Lys Thr Ala Ala Leu Gln Ser Ala Thr Pro Val Glu Arg Val Lys
        2060            2065            2070

Leu Gln Glu Ala Leu Ser Gln Leu Asp Phe Gln Trp Glu Lys Val
        2075            2080            2085

Asn Lys Met Tyr Lys Asp Arg Gln Gly Arg Phe Asp Arg Ser Val
        2090            2095            2100

Glu Lys Trp Arg Arg Phe His Tyr Asp Ile Lys Ile Phe Asn Gln
        2105            2110            2115

Trp Leu Thr Glu Ala Glu Gln Phe Leu Arg Lys Thr Gln Ile Pro
        2120            2125            2130

Glu Asn Trp Glu His Ala Lys Tyr Lys Trp Tyr Leu Lys Glu Leu
        2135            2140            2145

Gln Asp Gly Ile Gly Gln Arg Gln Thr Val Val Arg Thr Leu Asn
        2150            2155            2160

Ala Thr Gly Glu Glu Ile Ile Gln Gln Ser Ser Lys Thr Asp Ala
        2165            2170            2175

Ser Ile Leu Gln Glu Lys Leu Gly Ser Leu Asn Leu Arg Trp Gln
        2180            2185            2190

Glu Val Cys Lys Gln Leu Ser Asp Arg Lys Lys Arg Leu Glu Glu
        2195            2200            2205

Gln Lys Asn Ile Leu Ser Glu Phe Gln Arg Asp Leu Asn Glu Phe
        2210            2215            2220

Val Leu Trp Leu Glu Glu Ala Asp Asn Ile Ala Ser Ile Pro Leu
        2225            2230            2235

Glu Pro Gly Lys Glu Gln Gln Leu Lys Glu Lys Leu Glu Gln Val
        2240            2245            2250

Lys Leu Leu Val Glu Glu Leu Pro Leu Arg Gln Gly Ile Leu Lys
        2255            2260            2265

Gln Leu Asn Glu Thr Gly Gly Pro Val Leu Val Ser Ala Pro Ile
        2270            2275            2280

Ser Pro Glu Glu Gln Asp Lys Leu Glu Asn Lys Leu Lys Gln Thr
        2285            2290            2295

Asn Leu Gln Trp Ile Lys Val Ser Arg Ala Leu Pro Glu Lys Gln
        2300            2305            2310

Gly Glu Ile Glu Ala Gln Ile Lys Asp Leu Gly Gln Leu Glu Lys
        2315            2320            2325

Lys Leu Glu Asp Leu Glu Glu Gln Leu Asn His Leu Leu Leu Trp
        2330            2335            2340

Leu Ser Pro Ile Arg Asn Gln Leu Glu Ile Tyr Asn Gln Pro Asn
        2345            2350            2355

Gln Glu Gly Pro Phe Asp Val Gln Glu Thr Glu Ile Ala Val Gln
        2360            2365            2370

Ala Lys Gln Pro Asp Val Glu Glu Ile Leu Ser Lys Gly Gln His
        2375            2380            2385
```

```
Leu Tyr Lys Glu Lys Pro Ala Thr Gln Pro Val Lys Arg Lys Leu
    2390            2395                2400
Glu Asp Leu Ser Ser Glu Trp Lys Ala Val Asn Arg Leu Leu Gln
    2405            2410                2415
Glu Leu Arg Ala Lys Gln Pro Asp Leu Ala Pro Gly Leu Thr Thr
    2420            2425                2430
Ile Gly Ala Ser Pro Thr Gln Thr Val Thr Leu Val Thr Gln Pro
    2435            2440                2445
Val Val Thr Lys Glu Thr Ala Ile Ser Lys Leu Glu Met Pro Ser
    2450            2455                2460
Ser Leu Met Leu Glu Val Pro Ala Leu Ala Asp Phe Asn Arg Ala
    2465            2470                2475
Trp Thr Glu Leu Thr Asp Trp Leu Ser Leu Leu Asp Gln Val Ile
    2480            2485                2490
Lys Ser Gln Arg Val Met Val Gly Asp Leu Glu Asp Ile Asn Glu
    2495            2500                2505
Met Ile Ile Lys Gln Lys Ala Thr Met Gln Asp Leu Glu Gln Arg
    2510            2515                2520
Arg Pro Gln Leu Glu Glu Leu Ile Thr Ala Ala Gln Asn Leu Lys
    2525            2530                2535
Asn Lys Thr Ser Asn Gln Glu Ala Arg Thr Ile Ile Thr Asp Arg
    2540            2545                2550
Ile Glu Arg Ile Gln Asn Gln Trp Asp Glu Val Gln Glu His Leu
    2555            2560                2565
Gln Asn Arg Arg Gln Gln Leu Asn Glu Met Leu Lys Asp Ser Thr
    2570            2575                2580
Gln Trp Leu Glu Ala Lys Glu Glu Ala Glu Gln Val Leu Gly Gln
    2585            2590                2595
Ala Arg Ala Lys Leu Glu Ser Trp Lys Glu Gly Pro Tyr Thr Val
    2600            2605                2610
Asp Ala Ile Gln Lys Lys Ile Thr Glu Thr Lys Gln Leu Ala Lys
    2615            2620                2625
Asp Leu Arg Gln Trp Gln Thr Asn Val Asp Val Ala Asn Asp Leu
    2630            2635                2640
Ala Leu Lys Leu Leu Arg Asp Tyr Ser Ala Asp Asp Thr Arg Lys
    2645            2650                2655
Val His Met Ile Thr Glu Asn Ile Asn Ala Ser Trp Arg Ser Ile
    2660            2665                2670
His Lys Arg Val Ser Glu Arg Glu Ala Ala Leu Glu Glu Thr His
    2675            2680                2685
Arg Leu Leu Gln Gln Phe Pro Leu Asp Leu Glu Lys Phe Leu Ala
    2690            2695                2700
Trp Leu Thr Glu Ala Glu Thr Thr Ala Asn Val Leu Gln Asp Ala
    2705            2710                2715
Thr Arg Lys Glu Arg Leu Leu Glu Asp Ser Lys Gly Val Lys Glu
    2720            2725                2730
Leu Met Lys Gln Trp Gln Asp Leu Gln Gly Glu Ile Glu Ala His
    2735            2740                2745
Thr Asp Val Tyr His Asn Leu Asp Glu Asn Ser Gln Lys Ile Leu
    2750            2755                2760
Arg Ser Leu Glu Gly Ser Asp Asp Ala Val Leu Leu Gln Arg Arg
    2765            2770                2775
```

```
Leu Asp Asn Met Asn Phe Lys Trp Ser Glu Leu Arg Lys Lys Ser
    2780            2785            2790

Leu Asn Ile Arg Ser His Leu Glu Ala Ser Ser Asp Gln Trp Lys
    2795            2800            2805

Arg Leu His Leu Ser Leu Gln Glu Leu Leu Val Trp Leu Gln Leu
    2810            2815            2820

Lys Asp Asp Glu Leu Ser Arg Gln Ala Pro Ile Gly Gly Asp Phe
    2825            2830            2835

Pro Ala Val Gln Lys Gln Asn Asp Val His Arg Ala Phe Lys Arg
    2840            2845            2850

Glu Leu Lys Thr Lys Glu Pro Val Ile Met Ser Thr Leu Glu Thr
    2855            2860            2865

Val Arg Ile Phe Leu Thr Glu Gln Pro Leu Glu Gly Leu Glu Lys
    2870            2875            2880

Leu Tyr Gln Glu Pro Arg Glu Leu Pro Pro Glu Glu Arg Ala Gln
    2885            2890            2895

Asn Val Thr Arg Leu Leu Arg Lys Gln Ala Glu Glu Val Asn Thr
    2900            2905            2910

Glu Trp Glu Lys Leu Asn Leu His Ser Ala Asp Trp Gln Arg Lys
    2915            2920            2925

Ile Asp Glu Thr Leu Glu Arg Leu Gln Glu Leu Gln Glu Ala Thr
    2930            2935            2940

Asp Glu Leu Asp Leu Lys Leu Arg Gln Ala Glu Val Ile Lys Gly
    2945            2950            2955

Ser Trp Gln Pro Val Gly Asp Leu Leu Ile Asp Ser Leu Gln Asp
    2960            2965            2970

His Leu Glu Lys Val Lys Ala Leu Arg Gly Glu Ile Ala Pro Leu
    2975            2980            2985

Lys Glu Asn Val Ser His Val Asn Asp Leu Ala Arg Gln Leu Thr
    2990            2995            3000

Thr Leu Gly Ile Gln Leu Ser Pro Tyr Asn Leu Ser Thr Leu Glu
    3005            3010            3015

Asp Leu Asn Thr Arg Trp Lys Leu Leu Gln Val Ala Val Glu Asp
    3020            3025            3030

Arg Val Arg Gln Leu His Glu Ala His Arg Asp Phe Gly Pro Ala
    3035            3040            3045

Ser Gln His Phe Leu Ser Thr Ser Val Gln Gly Pro Trp Glu Arg
    3050            3055            3060

Ala Ile Ser Pro Asn Lys Val Pro Tyr Tyr Ile Asn His Glu Thr
    3065            3070            3075

Gln Thr Thr Cys Trp Asp His Pro Lys Met Thr Glu Leu Tyr Gln
    3080            3085            3090

Ser Leu Ala Asp Leu Asn Asn Val Arg Phe Ser Ala Tyr Arg Thr
    3095            3100            3105

Ala Met Lys Leu Arg Arg Leu Gln Lys Ala Leu Cys Leu Asp Leu
    3110            3115            3120

Leu Ser Leu Ser Ala Ala Cys Asp Ala Leu Asp Gln His Asn Leu
    3125            3130            3135

Lys Gln Asn Asp Gln Pro Met Asp Ile Leu Gln Ile Ile Asn Cys
    3140            3145            3150

Leu Thr Thr Ile Tyr Asp Arg Leu Glu Gln Glu His Asn Asn Leu
    3155            3160            3165

Val Asn Val Pro Leu Cys Val Asp Met Cys Leu Asn Trp Leu Leu
```

```
              3170                3175                3180
Asn Val Tyr Asp Thr Gly Arg Thr Gly Arg Ile Arg Val Leu Ser
              3185                3190                3195
Phe Lys Thr Gly Ile Ile Ser Leu Cys Lys Ala His Leu Glu Asp
              3200                3205                3210
Lys Tyr Arg Tyr Leu Phe Lys Gln Val Ala Ser Ser Thr Gly Phe
              3215                3220                3225
Cys Asp Gln Arg Arg Leu Gly Leu Leu Leu His Asp Ser Ile Gln
              3230                3235                3240
Ile Pro Arg Gln Leu Gly Glu Val Ala Ser Phe Gly Gly Ser Asn
              3245                3250                3255
Ile Glu Pro Ser Val Arg Ser Cys Phe Gln Phe Ala Asn Asn Lys
              3260                3265                3270
Pro Glu Ile Glu Ala Ala Leu Phe Leu Asp Trp Met Arg Leu Glu
              3275                3280                3285
Pro Gln Ser Met Val Trp Leu Pro Val Leu His Arg Val Ala Ala
              3290                3295                3300
Ala Glu Thr Ala Lys His Gln Ala Lys Cys Asn Ile Cys Lys Glu
              3305                3310                3315
Cys Pro Ile Ile Gly Phe Arg Tyr Arg Ser Leu Lys His Phe Asn
              3320                3325                3330
Tyr Asp Ile Cys Gln Ser Cys Phe Phe Ser Gly Arg Val Ala Lys
              3335                3340                3345
Gly His Lys Met His Tyr Pro Met Val Glu Tyr Cys Thr Pro Thr
              3350                3355                3360
Thr Ser Gly Glu Asp Val Arg Asp Phe Ala Lys Val Leu Lys Asn
              3365                3370                3375
Lys Phe Arg Thr Lys Arg Tyr Phe Ala Lys His Pro Arg Met Gly
              3380                3385                3390
Tyr Leu Pro Val Gln Thr Val Leu Glu Gly Asp Asn Met Glu Thr
              3395                3400                3405
Pro Val Thr Leu Ile Asn Phe Trp Pro Val Asp Ser Ala Pro Ala
              3410                3415                3420
Ser Ser Pro Gln Leu Ser His Asp Asp Thr His Ser Arg Ile Glu
              3425                3430                3435
His Tyr Ala Ser Arg Leu Ala Glu Met Glu Asn Ser Asn Gly Ser
              3440                3445                3450
Tyr Leu Asn Asp Ser Ile Ser Pro Asn Glu Ser Ile Asp Asp Glu
              3455                3460                3465
His Leu Leu Ile Gln His Tyr Cys Gln Ser Leu Asn Gln Asp Ser
              3470                3475                3480
Pro Leu Ser Gln Pro Arg Ser Pro Ala Gln Ile Leu Ile Ser Leu
              3485                3490                3495
Glu Ser Glu Glu Arg Gly Glu Leu Glu Arg Ile Leu Ala Asp Leu
              3500                3505                3510
Glu Glu Glu Asn Arg Asn Leu Gln Ala Glu Tyr Asp Arg Leu Lys
              3515                3520                3525
Gln Gln His Glu His Lys Gly Leu Ser Pro Leu Pro Ser Pro Pro
              3530                3535                3540
Glu Met Met Pro Thr Ser Pro Gln Ser Pro Arg Asp Ala Glu Leu
              3545                3550                3555
Ile Ala Glu Ala Lys Leu Leu Arg Gln His Lys Gly Arg Leu Glu
              3560                3565                3570
```

| | | | | | | | | | | | |
|---|---|---|---|---|---|---|---|---|---|---|---|
| Ala | Arg | Met | Gln | Ile | Leu | Glu | Asp | His | Asn | Lys | Gln | Leu | Glu | Ser |
| 3575 | | | | | 3580 | | | | | 3585 | |

Ala Arg Met Gln Ile Leu Glu Asp His Asn Lys Gln Leu Glu Ser
    3575                3580                3585

Gln Leu His Arg Leu Arg Gln Leu Leu Glu Gln Pro Gln Ala Glu
    3590                3595                3600

Ala Lys Val Asn Gly Thr Thr Val Ser Ser Pro Ser Thr Ser Leu
    3605                3610                3615

Gln Arg Ser Asp Ser Ser Gln Pro Met Leu Leu Arg Val Val Gly
    3620                3625                3630

Ser Gln Thr Ser Asp Ser Met Gly Glu Glu Asp Leu Leu Ser Pro
    3635                3640                3645

Pro Gln Asp Thr Ser Thr Gly Leu Glu Glu Val Met Glu Gln Leu
    3650                3655                3660

Asn Asn Ser Phe Pro Ser Ser Arg Gly Arg Asn Thr Pro Gly Lys
    3665                3670                3675

Pro Met Arg Glu Asp Thr Met
    3680                3685

<210> SEQ ID NO 65
<211> LENGTH: 19841
<212> TYPE: DNA
<213> ORGANISM: Homo sapiens

<400> SEQUENCE: 65

```
tttcctactt gaagcctgac gtagtaaaga tcggggagg gttagacaga tacagtggtc      60
cccaaccatt ttggcaccag ggactggtct tatggaagac agttttttcca cagactgttg    120
gggggatggt tttgggatga aaccgttctg cctctgatca tcaggtgtta gattctaata    180
aggagcgcac acctagatcc ctcgcatgca tagttcatgg tggggttcgc actcttacga    240
ggattgaatg gtgcgctgct ccggtaggag gctgggctca ggctgtaatg cctgctcgcc    300
caccactcac ctcctgctgc atggcctggt tcctaacagg ccacggacca ctactgttcc    360
atggcccgga ggttgaggac cccgagatac aggacaattc tgtggcaagc aggactgtcc    420
cctcgccaaa gatgggacat cgaggctcct tggagcaccc tgtggccacc ttgcagcagc    480
ctctgtttcc ccatgtttcc atgacctggt gtccatctgt cttccccagt ttgggagctt    540
ctctccgagg aggacctggg cctggtgtgg cacctgctgt gtgagcgggg ccatgtccaa    600
cggccttctt ggggactttg ggtcgggag aagttctgcc tgggttttac tgccttctcc      660
caacccccaca ctgtctcccc tggcagcggt tgatcgacaa gaccaaggtg acatatctga   720
agtggctgcc tgagtcggag agcctgttcc tggcatcaca cgccagtggc cacctgtacc    780
tgtacaacgt cagccaccc tgcgcctcgg ccccgcccca gtacagcctg ctgaagcagg     840
gcgagggctt ctctgtctat gctgccaaga gcaaggcacc ccgcaacccg ctggccaagt    900
gggcggtggg tgaggggccc ctcaacgagt tcgccttctc gcccgatggc cggcacctgg    960
cctgtgtgag ccaggatggc tgcctgcgcg tcttccactt cgactccatg ctcctgcgtg   1020
ggctcatgaa gagctacttt ggggggcctgc tgtgtgtgtg ctggagccct gacggccgct   1080
acgtggtgac gggtggcgaa gatgacctgg tcaccgtgtg gtccttcacc gagggccgcg   1140
tggtggctcg aggccatggc cacaagtcct gggtcaacgc tgtggccttt gaccctacac   1200
ccacaagggc agaggaggcg gcgacagcag ccggtgctga tggggagcgg agcggcgaag   1260
aggaggagga ggagcccgag gctgcggca caggctcggc cggggcgcc ccgctctctc      1320
cactgcccaa ggctggctcc attacttacc gctttggctc ggcgggccag gacacgcagt   1380
```

```
tctgcctgtg ggacctcact gaagacgtgc tctacccgca ccccccctg gcccgcaccc    1440
gcacctccc  tggcacacct ggcaccacgc caccggccgc cagcagctcg agggtggcg    1500
agcctggccc aggcccctg  cctcgctcgc tgtcccgctc aacagtctc  ccgcacccag   1560
ctggcggggg caaggcgggc ggcccgggtg tggcggcaga gcctggcaca ccattcagca   1620
ttggccgctt cgccacgctc acactgcagg agcggcggga ccgggggca  gagaaggagc   1680
acaagcgcta ccacagcctg gcaacatca  gccggggtgg cagtggcggc agtggcagtg   1740
gtggggagaa gcccagcggc cctgttcccc gcagccgcct ggaccccgcc aaggtgctgg   1800
gcactgcgct gtgcccgcgc atccacgagg tgccctgct  ggagccctt  gtgtgcaaga   1860
agatcgccca ggagcggctc acagtcctcc tgttcctgga ggactgcatc atcactgcct   1920
gccaggaggg cctcatctgc acctgggccc ggccgggcaa gcggtgagt  ggccccacac   1980
cagcctgccg gggacctggc aggaccttc  gtgggaagag gcaggcattg gcagagagag   2040
ggctttgttg ctgtcacagc ctctggctcc gtggggtgag gggaagccag ggaaatctta   2100
gtgtctcagt acaagacctc tcagatcctt agagtgaggg ggtctagccc taggcagcag   2160
gcagcagaaa gaggggtggg tgtgagagcc agctaggaat tggggcatcc aaggctggcc   2220
gtctgaaggg cagcagatgg gccccacatg gccaggtctt actgcctgtc actcgaacca   2280
gaatctattt ctgttgaaca tctgtttttt aaatcgtgaa acttttttga gtacttcagg   2340
ccaaaactag gggcgagctc aagcctgtgg gcatggctgc cagcctgggt ctgggactca   2400
ggatctgagc ctcctgctga aggcacaggc tgggaatccc aggcctgggt tccagtccca   2460
ctccctctgt gaccctggac aagtcactgc cccctctgac ctccaactca tcacctctta   2520
gaacagagcc tgtaggatgg gcagtgggtg gatgtgcttg cctcctgggt gggctgtggc   2580
gttgggaagg tcatagtagg cgaatcaggc ctggcatctt gtaagttcgg agctcgtctt   2640
gggtgtctca gcttcttagg gcttggactc agttgcccag ggtcctggag gccgtggctt   2700
ggttcctcag atcctcagtt ttggaatcgt agagtcctga gtcccctagaa cttgagagca   2760
cagtctgagt gactcagagg caagagtggt gggatttggg gagtctggtt gagtcctaaa   2820
agagacccct ctgtctccgt agttcacaga cgaggagacc gaggcccaga caggggaagg   2880
aagttggccc aggtcaccca gcaagtcagt ggtagaggta ggactgtccc tgagttcttt   2940
ccccagcacc tcagggtccc tcccaagtta aagggagct  ccagtttccc cctcccctcc   3000
caccttacc  cttaccccat ggtctcactc aggatccgcc aaggactttg attattgcgt   3060
gaaagtgctg actgccagga caggaagcta gctaagatgc aagttcccag cctagagcag   3120
tggcctctgg ggggtctagg gcggacccaa gggcaaggcc agggtggcag cagctttggg   3180
gactctgggc tggctccctc cccttgacac tggctgaagc ccaggtggtc tctaaccct   3240
cccatctctc cctctcatct tccccagggc atctcctccc aaccaggcaa ctccccgagt   3300
ggcacagtgg tgtgaagcca tggatatcgg gccccccaa  ccccatgccc ccagcctcct   3360
agccataacc ctccctgctg acctcacaga tcaacgtatt aacaagacta accatgatgg   3420
atggactgct ccagtccccc cacctgcaca aaatttgggg gcccccaga  ctggcccgga   3480
cacgggcgat gtaatagccc ttgtggcctc agccttgtcc cccacccact gccaagtaca   3540
atgacctctt cctctgaaac atcagtgtta ccctcatccc tgtcccagc  atgtgactgg   3600
tcactcctgg ggagagactc cccgcccctg ccacaagagc cccaggtctg cagtgtgccc   3660
ctcagttgag tggcagggc  cggggtggt  ccagccctcg cccggccccc accccagctg   3720
cccttgctat tgtctgtgct tttgaagagt gttaaattat ggaagcccct caggttcctc   3780
```

```
cctgtcccgc aggacctctt atttatacta aagttccctg ttttctcagc gggtctgtcc    3840
ccttcggagg agatgatgta gaggacctgt gtgtgtactc tgtggttcta ggcagtccgc    3900
tttccccaga ggaggagtgc aggcctgctc ccagcccagc gcctcccacc cctttttcata   3960 gcaggaaaag ccggagccca gggagggaac ggacctgcga gtcacacaac tggtgaccca    4020
caccagcggc tggagcagga ccctcttggg gagaagagca tcctgcccgc agccagggcc    4080
cctcatcaaa gtcctcggtg ttttttaaat tatcagaact gcccaggacc acgtttccca    4140
ggccctgccc agctgggact cctcggtcct tgcctcctag tttctcaggc ctggccctct    4200
caaggcccag gcaccccagg ccggttggag gccccgactt ccactctgga gaaccgtcca    4260
ccctggaaag aagagctcag attcctcttg gctctcggag ccgcagggag tgtgtcttcc    4320
cgcgccaccc tccaccccc gaaatgtttc tgtttctaat cccagcctgg gcaggaatgt     4380
ggctccccgg ccaggggcca aggagctatt tgggggtctc gtttgcccag ggagggcttg    4440
gctccaccac tttcctcccc cagcctttgg gcagcaggtc accctgttc aggctctgag     4500 ggtgcccct cctggtcctg tcctcaccac cccttcccca cctcctggga aaaaaaaaa      4560 aaaaaaaaa aaaagctggt ataaagcaga gagcctgagg gctaaattta actgtccgag     4620
tcggaatcca tctctgagtc acccaagaag ctgcctggc ctcccgtccc cttcccaggc     4680 ctcaaccct ttctcccacc cagccccaac ccccagccct cacccctag cccccagttc      4740 tggagcttgt cgggagcaag ggggtggttg ctactgggtc actcagcctc aattggccct    4800
gtttcagcaa tggcaggtt cttcttgaaa ttcatcacac ctgtggcttc ctctgtgctc     4860 tacctttta ttggggtgac agtgtgacag ctgagattct ccatgcattc ccctactct      4920 agcactgaag ggttctgaag ggccctggaa ggagggagct tggggggctg gcttgtgagg    4980
ggttaaggct gggaggcggg aggggggctg gaccaagggg tggggagaag gggaggaggc    5040
ctcggccggc cgcagagaga agtggccaga gaggcccagg ggacagccag ggacaggcag    5100
acatgcagcc agggctccag ggcctggaca ggggctgcca ggccctgtga caggaggacc    5160
ccgagccccc ggcccgggga ggggccatgg tgctgcctgt ccaacatgtc agccgaggtg    5220
cggctgaggc ggctccagca gctggtgttg gaccgggct tcctggggct ggagcccctg     5280
ctcgaccttc tcctgggcgt ccaccaggag ctgggcgcct ccgaactggc ccaggacaag    5340
tacgtggccg acttcttgca gtggggtgag tgcctaccct cggggctcct gcagatgggg    5400
tgggggtggg gcaggagaca ggtctgggca cagaggcctg gctgttgggg gggcaggatg    5460
gcaggatggg catggggaga tcctcccatc ctggggctca gagtgtggac ctgggccctg    5520
gggcaacatt tctctgtcct atgccaccac tctggagggg cagagtaagg tcagcagagg    5580
ctagggtggc tgtgactcag agccatggct taggagtcac agcaggctag gctgccaaca    5640
gcctcccatg gcctctctgc acccgcctc agggtcaggg tcagggtcat gctgggagct    5700
ccctctccta ggaccctccc cccaaaaagtg ggctctatgg ccctctcccc tggtttcctg   5760
tggcctgggg caagccagga gggccagcat ggggcagctg ccaggggcgc agccgacagg    5820
caggtgttcg gcgccagcct ctccagctgc cccaacaggt gcccaggcac tggagggcg     5880 gtgactcacg cgggccctgt gggagaacca gctttgcaga caggcgccac cagtgccccc    5940
tcctctgcga tccaggaggg acaactttgg gttcttctgg gtgtgtctcc ttctttttgta   6000 ggttctgcac ccaccccac ccccagcccc aaagtctcgg ttcctatgag ccgtgtgggt     6060
cagccaccat tcccgccacc ccgggtccct gcgtccttta gttctcctgg cccagggcct    6120
```

```
ccaaccttcc agctgtccca caaaacccct tcttgcaagg gctttccagg gcctggggcc    6180
agggctggaa ggaggatgct tccgcttctg ccagctgcct tgtctgccca cctcctcccc    6240
aagcccagga ctcgggctca ctggtcactg gtttctttca ttcccagcac cctgcccctc    6300
tggccctcat atgtctggcc ctcagtgact ggtgtttggt ttttggcctg tgtgtaacaa    6360
actgtgtgtg acacttgttt cctgtttctc cgccttcccc tgcttcctct tgtgtccatc    6420
tctttctgac ccaggcctgg ttcctttccc tcctcctccc atttcacaga tgggaaggtg    6480
gaggccaaga agggccaggc cattcagcct ctggaaaaac cttctcccaa cctcccacag    6540
cccctaatga ctctcctggc ctccctttag tagaggatga agttgggttg gcagggtaaa    6600
ctgagaccgg gtggggtagg ggtctggcgc tcccgggagg agcactcctt ttgtggcccg    6660
agctgcatct cgcggcccct cccctgccag gctgggggcg ggggagggggg ccagggttcc    6720 tgctgcctta aaagggctca atgtcttggc tctctcctcc ctcccccgtc ctcagccctg    6780
gctggttcgt ccctgctggc ccactctccc ggaaccccc ggaaccctc tctttcctcc      6840 agaacccact gtctcctctc cttccctccc ctcccatacc catccctctc tccatcctgc    6900
ctccacttct tccaccccg ggagtccagg cctccctgtc cccacagtcc ctgagccaca     6960
agcctccacc ccagctggtc cccacccag gctgcccagt ttaacattcc tagtcatagg     7020
accttgactt ctgagaggcc tgattgtcat ctgtaaataa ggggtaggac taaagcactc    7080
ctcctggagg actgagagat gggctggacc ggagcacttg agtctgggat atgtgaccat    7140
gctacctttg tctccctgtc ctgttccttc cccagccccc aaatccaggg ttttccaaag    7200
tgtggttcaa gaaccacctg catctgaatc tagaggtact ggatacaacc ccacgtctgg    7260
gccgttaccc aggacattct acatgagaac gtgggggtgg ggccctggct gcacctgaac    7320
tgtcacctgg agtcagggtg gaaggtggaa gaactgggtc ttatttcctt ctccccttgt    7380
tctttagggt ctgtccttct gcagactccg ttaccccacc ctaaccatcc tgcacaccct    7440
tggagccctc tgggccaatg ccctgtcccg caaagggctt tcaggcatc tcacctctat     7500 gggagggcat ttttggcccc cagaacctta cacggtgttt atgtggggaa gcccctggga    7560
agcagacagt cctagggtga agctgagagg cagagagaag gggagacaga cagagggtgg    7620
ggctttcccc cttgtctcca gtgccctttc tggtgaccct cggttctttt cccccaccac    7680 cccccagcg gagcccatcg tggtgaggct taaggaggtc cgactgcaga gggacgactt     7740
cgagattctg aaggtgatcg gacgcggggc gttcagcgag gtaagccgaa ccgggcggga    7800
gcctgacttg actcgtggtg ggcggggcat aggggttggg gcgggccctt agaaattgat    7860
gaatgaccga gccttagaac ctagggctgg gctggaggcg gggcttggga ccaatgggcg    7920
tggtgtggca ggtggggcgg ggccacggct gggtgcagaa gcggtggag ttgggtctgg     7980 gcgagccctt ttgttttccc gccgtctcca ctctgtctca ctatctcgac ctcaggtagc    8040
ggtagtgaag atgaagcaga cgggccaggt gtatgccatg aagatcatga acaagtggga    8100
catgctgaag aggggcgagg tgaggggctg ggcggacgtg gggggctttg aggatccgcg    8160
ccccgtctcc ggctgcagct cctccgggtg ccctgcaggt gtcgtgcttc cgtgaggaga    8220
gggacgtgtt ggtgaatggg gaccggcggt ggatcacgca gctgcacttc gccttccagg    8280
atgagaacta cctggtgagc tccgggccgg ggtgactagg aagagggaca agagcccgtg    8340
ctgtcactgg acgaggaggt ggggagagga agctctagga ttgggggtgc tgcccggaaa    8400
cgtctgtggg aaagtctgtg tgcggtaaga gggtgtgtca ggtggatgag gggccttccc    8460
tatctgagac ggggatggtg tccttcactg cccgtttctg gggtgatctg ggggactctt    8520
```

```
ataaagatgt ctctgttgcg gggggtctct tacctggaat gggataggtc ttcaggaatt   8580
ctaacggggc cactgcctag ggaaggagtg tctgggacct attctctggg tgttgggtgg   8640
cctctgggtt ctcttcccca gaacatctca gggggagtga atctgcccag tgacatccca   8700
ggaaagtttt tttgtttgtg ttttttttg agggcgggg gcggggccg caggtggtct   8760 ctgatttggc ccggcagatc tctatggtta tctctgggct ggggctgcag gtctctgccc   8820
aaggatgggg tgtctctggg aggggttgtc ccagccatcc gtgatggatc agggcctcag   8880
gggactacca accacccatg acgaaccct tctcagtacc tggtcatgga gtattacgtg   8940 ggcgggacc tgctgacact gctgagcaag tttgggagc ggattccggc cgagatggcg   9000
cgcttctacc tggcggagat tgtcatggcc atagactcgg tgcaccggct tggctacgtg   9060
cacaggtggg tgcagcatgg ccgaggggat agcaagcttg ttccctggcc gggttcttgg   9120
aaggtcagag cccagagagg ccagggcctg gagagggacc ttcttggttg ggcccaccg   9180 gggggtgcct gggagtaggg gtcagaactg tagaagccct acaggggcgg aacccgagga   9240
agtggggtcc caggtggcac tgcccggagg ggcggagcct ggtgggacca cagaagggag   9300
gttcatttat cccacccttc tcttttcctc cgtgcaggga catcaaaccc gacaacatcc   9360
tgctggaccg ctgtggccac atccgcctgg ccgacttcgg ctcttgcctc aagctgcggg   9420
cagatggaac ggtgagccag tgccctggcc acagagcaac tggggctgct gatgagggat   9480
ggaaggcaca gagtgtggga gcgggactgg atttggaggg gaaagaggt ggtgtgaccc   9540 aggcttaagt gtgcatctgt gtggcggagt attagaccag gcagagggag gggctaagca   9600 tttgggagt ggttggaagg agggcccaga gctggtgggc ccagaggggt gggcccaagc   9660
ctcgctctgc tcctttggt ccaggtgcgg tcgctggtgg ctgtgggcac cccagactac   9720
ctgtcccccg agatcctgca ggctgtgggc ggtgggcctg ggacaggcag ctacgggccc   9780
gagtgtgact ggtgggcgct gggtgtattc gcctatgaaa tgttctatgg gcagacgccc   9840
ttctacgcgg attccacggc ggagacctat ggcaagatcg tccactacaa ggtgagcacg   9900
gccgcaggga gacctggcct ctcccggtag gcgctcccag gctatcgcct cctctccctc   9960
tgagcaggag cacctctctc tgccgctggt ggacgaaggg gtccctgagg aggctcgaga  10020
cttcattcag cggttgctgt gtccccgga gacacggctg ggccggggtg gagcaggcga  10080
cttccggaca catcccttct tctttggcct cgactgggat ggtctccggg acagcgtgcc  10140 ccccttttaca ccggatttcg aaggtgccac cgacacatgc aacttcgact tggtggagga  10200
cgggctcact gccatggtga gcggggggcgg ggtaggtacc tgtggcccct gctcggctgc  10260
gggaacctcc ccatgctccc tccataaagt tggagtaagg acagtgccta ccttctgggg  10320
tcctgaatca ctcattcccc agagcacctg ctctgtgccc atctactact gaggacccag  10380
cagtgaccta gacttacagt ccagtggggg aacacagagc agtcttcaga cagtaaggcc  10440
ccagagtgat cagggctgag acaatggagt gcaggggtg ggggactcct gactcagcaa  10500
ggaaggtcct ggagggcttt ctggagtggg gagctatctg agctgagact tggagggatg  10560
agaagcagga gaggactcct cctcccttag gccgtctctc ttcaccgtgt aacaagctgt  10620
catggcatgc ttgctcggct ctgggtgccc ttttgctgaa caatactggg gatccagcac  10680
ggaccagatg agctctggtc cctgccctca tccagttgca gtctagagaa ttagagaatt  10740
atggagagtg tggcaggtgc cctgaaggga agcaacagga tacaagaaaa aatgatgggg  10800
ccaggcacgg tggctcacgc ctgtaacccc agcaatttgg caggccgaag tgggtggatt  10860
```

```
gcttgagccc aggagttcga gaccagcctg gcaatgtgg tgagacccc gtctctacaa    10920 aaatgtttta aaaattggtt gggcgtggtt gcgcatgcct gtatactcag ctactagggt    10980
ggccgacgtg ggcttgagcc caggaggtca aggctgcagt gagctgtgat tgtgccactg    11040
cactccagcc tgggcaacgg agagagactc tgtctcaaaa ataagataaa ctgaaattaa    11100
aaaataggct gggctggccg ggcgtggtgg ctcacgcctg taatctcagc actttgggag    11160
gccgaggcgg gtggatcacg aggtcaggag atcgagacca tcttggctaa cacggtgaaa    11220
ccccatctct cctaaaaata caaaaaatta gccaggcgtg gtggcgggcg cctgtagtcc    11280
cagctactca ggaggctgag gcaggagaat ggcgtgaacc cgggaggcag agtttgcagt    11340
gagccgagat cgtgccactg cactccagcc tgggcgacag agcgagactc tgtctcagaa    11400
aaaaaaaaaa aaaaaaaaaa aaataggct gaccgcggcc gggcgctgtg gctcatgcct    11460
gtaatcccag cactttggga gtccaaggcc ggtgggtcat gagatcagga gttttgagac    11520
taggctggcc aacacggtga aaccccgtct ctactaaaaa tacaagaaaa ttagctgggt    11580
gtggtctcgg gtgcctgtaa ttccagttac tgggaagct gaggcaggag aattgcttga    11640
acctgggagg cagagtttgc agtgagccaa gatcatgcca ctacactcca gtctgggtga    11700
cagagtgaga ctctgtctca aaaaaaaaaa aaaaaaaag ggttgggcaa ggtggttcac    11760
gcctgtaatc ccagaacttt gggaggctga ggcaggcaga tcactggaag tcaggagttc    11820
aagaccagcc tggccaacat ggtgaaaccc tgtgtctact aaaaatacaa aatttagcca    11880
ggcttggtgg cgtatgcctg taatgccagc tactcaggag gctgaggcag gagaatcgct    11940
tgattgaacc tgggaggcag agtttgcagt gggctgggt tgtgccactg cactctaggc    12000
tgggagacag caagactcca tctaaaaaaa aaaacagaa ctgggctggg cacagtggct    12060
tatatttgta atcccagcac tttgggagc tgaggttgga ggactgcttg agcccagagt    12120
ttgggactac aacagctgag gtaggcggat cacttgaggt cagaagatgg agaccagcct    12180
ggccagcgtg gcgaaacccc gtctctacca aaaatataaa aaattagcca ggcgtggtag    12240
agggcgcctg taatctcagc tactcaggac gctgaggcag gagaatcgcc tgaacctggg    12300
aggcggaggt tgcagtgagc tgagattgca ccactgcact ccagcctggg taacagagcg    12360
agactccgta tcaaagaaaa agaaaaaaga aaaatgctg gaggggccac tttagataag    12420
ccctgagttg gggctggttt gggggggaaca tgtaagccaa gatcaaaaag cagtgagggg    12480
cccgccctga cgactgctgc tcacatctgt gtgtcttgcg caggagacac tgtcggacat    12540
tcgggaaggt gcgccgctag gggtccacct gcctttgtg ggctactcct actcctgcat    12600
ggccctcagg taagcactgc cctggacggc ctccaggggc cacgaggctg cttgagcttc    12660
ctgggtcctg ctccttggca gccaatggag ttgcaggatc agtcttggaa ccttactgtt    12720
ttgggcccaa agactcctaa gaggccagag ttggaggacc ttaaattttc agatctatgt    12780
acttcaaaat gttagattga attttaaaac ctcagagtca cagactgggc ttcccagaat    12840
cttgtaacca ttaacttta cgtctgtagt acacagagcc acaggacttc agaacttgga    12900
aaatatgaag tttagacttt tacaatcagt tgtaaaagaa tgcaaattct ttgaatcagc    12960
catataacaa taaggccatt taaaagtatt aatttaggcg ggccgcggtg gctcacgcct    13020
gtaatcctag cactttggga ggccaaggca ggtggatcat gaggtcagga gatcgagacc    13080
atcctggcta acacggtgaa accccgtctc tactaaaaat acaaaaaaat tagccgggca    13140
tggtggcggg cgcttgcggt cccagctact gggaggcga ggcaggagaa tggcatgaac    13200
ccgggaggcg gagcttgcag tgagccgaga tcatgccact gcactccagc ctgggcgaca    13260
```

```
gagcaagact ccgtctcaaa aaaaaaaaaa aaaaagtatt tatttaggcc gggtgtggtg    13320
gctcacgcct gtaattccag tgctttggga ggatgaggtg ggtggatcac ctgaggtcag    13380
gagttcgaga ccagcctgac caacgtggag aaacctcatc tctactaaaa aacaaaatta    13440
gccaggcgtg gtggcatata cctgtaatcc cagctactca ggaggctgag gcaggagaat    13500
cagaacccag gaggggagg ttgtggtgag ctgagatcgt gccattgcat tccagcctgg    13560
gcaacaagag tgaaacttca tctcaaaaaa aaaaaaaaaa aagtactaat ttacaggctg    13620
ggcatggtgg ctcacgcttg gaatcccagc actttgggag gctgaagtgg acggattgct    13680
tcagcccagt agttcaagac cagcctgagc aacataatga gaccctgtct ctacaaaaaa    13740
ttgaaaaaat cgtgccaggc atggtggtct gtgcctgcag tcctagctac tcaggagtct    13800
gaagtaggag aatcacttga gcctggagtt tgaggcttca gtgagccatg atagattcca    13860
gcctaggcaa caaagtgaga cctggtctca acaaaagtat taattacaca aataatgcat    13920
tgcttatcac aagtaaatta gaaaatacag ataaggaaaa ggaagttgat atctcgtgag    13980
ctcaccagat ggcagtggtc cctggctcac acgtgtactg acacatgttt aaatagtgga    14040
gaacaggtgt tttttttggtt tgtttttttc cccttcctca tgctactttg tctaagagaa    14100
cagttggttt tctagtcagc ttttattact ggacaacatt acacatacta taccttatca    14160
ttaatgaact ccagcttgat tctgaaccgc tgcggggcct gaacggtggg tcaggattga    14220
acccatcctc tattagaacc caggcgcatg tccaggatag ctaggtcctg agccgtgttc    14280
ccacaggagg gactgctggg ttggaggga cagccacttc ataccccagg gaggagctgt    14340 cccccttccca cagctgagtg gggtgtgctg acctcaagtt gccatcttgg ggtcccatgc    14400
ccagtcttag gaccacatct gtggaggtgg ccagagccaa gcagtctccc catcaggtcg    14460
gcctccctgt cctgaggccc tgagaagagg ggtctgcagc ggtcacatgt caagggagga    14520
gatgagctga ccctagaaca tggggtctg gaccccaagt ccctgcagaa ggtttagaaa    14580
gagcagctcc caggggccca aggccaggag aggggcaggg cttttcctaa gcagaggagg    14640
ggctattggc ctacctggga ctctgttctc ttcgctctgc tgctcccctt cctcaaaatca    14700 ggaggtcttg gaagcagctg cccctaccca caggccagaa gttctggttc tccaccagag    14760
aatcagcatt ctgtctccct ccccactccc tcctcctctc cccagggaca gtgaggtccc    14820
aggccccaca cccatggaac tggaggccga gcagctgctt gagccacacg tgcaagcgcc    14880
cagcctggag ccctcggtgt ccccacagga tgaaacagta agttggtgga ggggagggg    14940 tccgtcaggg acaattggga gagaaaaggt gagggcttcc cgggtggcgt gcactgtaga    15000
gccctctagg gacttcctga acagaagcag acagaaacca cggagagacg aggttacttc    15060
agacatggga cggtctctgt agttacagtg gggcattaag taagggtgtg tgtgttgctg    15120
gggatctgag aagtcgatct ttgagctgag cgctggtgaa ggagaaacaa gccatggaag    15180
gaaaggtgcc aagtggtcag gcgagagcct ccagggcaaa ggccttgggc agtgggaat    15240 cctgatttgt tcctgaaagg tagtttggct gaatcattcc tgagaaggct ggagaggcca    15300
gcaggaaaca aaacccagca aggccttttg tcgtgagggc attagggagc tggagggatt    15360
ttgagcagca gagggacata ggttgtgtta gtgtttgagc accagccctc tggtccctgt    15420
gtagatttag aggaccagac tcagggatgg ggctgaggga ggtagggaag ggaggggct    15480 tggatcattg caggagctat ggggattcca gaaatgttga ggggacgag gagtagggga    15540 taaacaagga ttcctagcct ggaaccagtg cccaagtcct gagtcttcca ggagccacag    15600
```

```
gcagccttaa gcctggtccc catacacagg ctgaagtggc agttccagcg gctgtccctg   15660
cggcagaggc tgaggccgag gtgacgctgc gggagctcca ggaagccctg gaggaggagg   15720
tgctcacccg gcagagcctg agccgggaga tggaggccat ccgcacggac aaccagaact   15780
tcgccaggtc gggatcgggg ccggggccgg ggccgggatg cgggccggtg caacccttg    15840 gcatcccctc tcgtccggcc cggacggact caccgtcctt acctcccac agtcaactac     15900 gcgaggcaga ggctcggaac cgggacctag aggcacacgt ccggcagttg caggagcgga   15960
tggagttgct gcaggcagag ggagccacag gtgagtccct catgtgtccc cttccccgga   16020
ggaccgggag gaggtgggcc gtctgctccg cggggcgtgt atagacacct ggaggaggga   16080
agggacccac gctggggcac gccgcgccac cgccctcctt cgcccctcca cgcgccctat   16140
gcctctttct tctccttcca gctgtcacgg gggtcccag tccccgggcc acggatccac      16200
cttcccatgt aagacccctc tctttcccct gcctcagacc tgctgcccat tctgcagatc   16260
ccctccctgg ctcctggtct ccccgtccag atatagggct caccctacgt ctttgcgact   16320
ttagagggca gaagcccttt attcagcccc agatctccct ccgttcaggc ctcaccagat   16380
tccctccggg atctccctag ataacctccc caacctcgat tcccctcgct gtctctcgcc    16440
ccaccgctga gggctgggct gggctccgat cgggtcacct gtcccttctc tctccagcta   16500
gatggccccc cggccgtggc tgtgggccag tgcccgctgg tggggccagg ccccatgcac   16560
cgccgccacc tgctgctccc tgccagggta cgtccggctg cccacgcccc cctccgccgt     16620
cgcgccccgc gctccacccg ccccttgcca cccgcttagc tgcgcatttg cggggctggg   16680
cccacggcag gagggcggat cttcgggcag ccaatcaaca caggccgcta ggaagcagcc   16740
aatgacgagt tcggacggga ttcgaggcgt gcgagtggac taacaacagc tgtaggctgt   16800
tggggcgggg gcggggcgca gggaagagtg cgggcccacc tatgggcgta ggcggggcga   16860
gtcccaggag ccaatcagag gcccatgccg ggtgttgacc tcgccctctc cccgcaggtc    16920
cctaggcctg gcctatcgga ggcgcttttcc ctgctcctgt tcgccgttgt tctgtctcgt    16980
gccgccgccc tgggctgcat tgggttggtg gcccacgccg gccaactcac cgcagtctgg   17040
cgccgcccag gagccgcccg cgctccctga accctagaac tgtcttcgac tccggggccc   17100
cgttggaaga ctgagtgccc ggggcacggc acagaagccg cgcccaccgc ctgccagttc   17160
acaaccgctc cgagcgtggg tctccgccca gctccagtcc tgtgatccgg gcccgccccc   17220
tagcggccgg ggagggaggg gccgggtccg cggccggcga acggggctcg aagggtcctt   17280
gtagccggga atgctgctgc tgctgctgct gctgctgctg ctgctgctgc tgctgctgct   17340
gctgctgctg ctgggggggat cacagaccat ttctttcttt cggccaggct gaggccctga   17400
cgtggatggg caaactgcag gcctgggaag gcagcaagcc gggccgtccg tgttccatcc   17460
tccacgcacc cccacctatc gttggttcgc aaagtgcaaa gctttcttgt gcatgacgcc    17520
ctgctctggg gagcgtctgg cgcgatctct gcctgcttac tcgggaaatt tgcttttgcc   17580
aaacccgctt tttcggggat cccgcgcccc cctcctcact tgcgctgctc tcggagcccc   17640
agccggctcc gcccgcttcg gcggtttgga tatttattga cctcgtcctc cgactcgctg   17700
acaggctaca ggacccccaa caaccccaat ccacgttttg gatgcactga dcccccgaca   17760
ttcctcggta tttattgtct gtcccacct aggaccccca ccccgaccc tcgcgaataa     17820 aaggccctcc atctgcccaa agctctggac tccacagtgt ccgcggtttg cgttgtgggc   17880
cggaggctcc gcagcgggcc aatcggagg cgtgtggagg cggccgaagg tctgggagga    17940
gctagcggga tgcgaagcgg ccgaatcagg gttgggggag gaaaagccac ggggcgggc    18000
```

```
tttggcgtcc ggccaatagg agggcgagcg ggccacccgg aggcaccgcc cccgcccagc    18060
tgtggcccag ctgtgccacc gagcgtcgag aagaggggga tgggctggca gcgcgcgcg    18120
ccatcctcct tccactgcgc ctgcgcacgc cacgcgcatc cgctcctggg acgcaagctc    18180
gagaaaagtt gctgcaaact ttctagcccg ttcccccgccc ctcctcccgg ccagacccgc    18240
ccccctgcg gagccgggaa ttccgagggg cggagcgcag gccgagatgg ggaatgtggg    18300
ggcctgcaga ggaccctgga gacggaggcg tgcagaagct cagtctcggg gcggaggctt    18360
cgcgccctta gtcctcctgg acggcccgtt accttctgcg ttgtcccgat ggggaaactg    18420
aggccctgag ccagaagcac acgctggggg gaggcagaaa gcgcggccag aggcggaggg    18480
aaaacaaagg gagaatcaca gacagacggg aggggacgg acacacacaa ggggacagag    18540
acccgagtgg agagctggat ctcgccttcc cggcgtgggg cgcagggtcg gccagaaaga    18600
agatcgagaa gagcggggag tgggggcgaa aaggggggac aggtggggga ggaggctggg    18660
gaaagcccga gggaggaaga gagggaggga ggaacttccc aaagttgcaa aacatggcta    18720
ccttgcctgc ggagccgagc gcggggccgg cggctggggg ggaggcggtg gcggcggcgg    18780
cggcgaccga agaggaggag gaggaagcgc gccagctctt gcagactttg caggcggccg    18840
agggtgaggc ggcggcggcg gccggggccg gggcgggcgc agcggctgcg ggagctgagg    18900
gcccgggatc cccggggcgtc cccggtcgc ccccgaggc cgcttccgaa ccgcccacgg    18960
gcctccgctt ctcgcccgag caggtggcgt gcgtctgcga ggcgctgctc caggcgggcc    19020
acgccggccg cttgagccgc ttcctgggcg cactgccccc ggccgagcgc ctacgtggca    19080
gcgacccggt gttgcgcgcg cgggccctgg tggccttcca gcggggcgag tacgccgagc    19140
tctaccggct actcgagagc cgccccttcc ccgccgccca ccacgccttc ctgcaggacc    19200
tctacctgcg cgcgcgctac catgaggccg agcgggcccg cggccgcgcg cttggcgcag    19260
tggacaagta tcgactgcgc aagaagttcc cgctgcccaa gaccatctgg gacggcgagg    19320
agacagtcta ctgcttcaag gagcgctccc gcgcagcgct caaggcctgc taccgcggca    19380
accgctaccc cacgccggac gagaagcgcc gcctggccac actcaccggc ctgtcgctca    19440
cgcaggtcag caactggttc aagaaccggc gacagcgcga ccggaccggg gccggaggcg    19500
gcgcgccctg caagaggtga ggggcctcgg gcggcgcaag tccagctctc ccggggacat    19560
cccgtccacc agccctcttc ccccgtgccc actgctgggg ccggcgcgcc gaggtcctcg    19620
gacatctccc gggaccagct cacaatctca ggcgcccgcg gggcgcgggg actaagtgtg    19680
gacgggacag gcacccgccc gggccctctc cccgcacgcg tctcctcttc cagcggctcc    19740
attccgagct ccttcccaaa tcccatcggt gttggggaat cacactgcgg ggggcactag    19800
agggactgag gaaaaaggac agggcctgtg gccactccac t                       19841
```

<210> SEQ ID NO 66
<211> LENGTH: 842
<212> TYPE: PRT
<213> ORGANISM: Homo sapiens

<400> SEQUENCE: 66

```
Met Ser Arg Pro Leu Ser Asp Gln Glu Lys Arg Lys Gln Ile Ser Val
 1               5                  10                  15

Arg Gly Leu Ala Gly Val Glu Asn Val Thr Glu Leu Lys Lys Asn Phe
            20                  25                  30

Asn Arg His Leu His Phe Thr Leu Val Lys Asp Arg Asn Val Ala Thr
        35                  40                  45
```

```
Pro Arg Asp Tyr Tyr Phe Ala Leu Ala His Thr Val Arg Asp His Leu
    50              55                  60

Val Gly Arg Trp Ile Arg Thr Gln Gln His Tyr Tyr Glu Lys Asp Pro
65              70                  75                  80

Lys Arg Ile Tyr Tyr Leu Ser Leu Glu Phe Tyr Met Gly Arg Thr Leu
                85                  90                  95

Gln Asn Thr Met Val Asn Leu Ala Leu Glu Asn Ala Cys Asp Glu Ala
            100                 105                 110

Thr Tyr Gln Leu Gly Leu Asp Met Glu Glu Leu Glu Glu Ile Glu Glu
        115                 120                 125

Asp Ala Gly Leu Gly Asn Gly Gly Leu Gly Arg Leu Ala Ala Cys Phe
130                 135                 140

Leu Asp Ser Met Ala Thr Leu Gly Leu Ala Ala Tyr Gly Tyr Gly Ile
145                 150                 155                 160

Arg Tyr Glu Phe Gly Ile Phe Asn Gln Lys Ile Ser Gly Gly Trp Gln
                165                 170                 175

Met Glu Glu Ala Asp Asp Trp Leu Arg Tyr Gly Asn Pro Trp Glu Lys
            180                 185                 190

Ala Arg Pro Glu Phe Thr Leu Pro Val His Phe Tyr Gly His Val Glu
        195                 200                 205

His Thr Ser Gln Gly Ala Lys Trp Val Asp Thr Gln Val Val Leu Ala
    210                 215                 220

Met Pro Tyr Asp Thr Pro Val Pro Gly Tyr Arg Asn Asn Val Val Asn
225                 230                 235                 240

Thr Met Arg Leu Trp Ser Ala Lys Ala Pro Asn Asp Phe Asn Leu Lys
                245                 250                 255

Asp Phe Asn Val Gly Gly Tyr Ile Gln Ala Val Leu Asp Arg Asn Leu
            260                 265                 270

Ala Glu Asn Ile Ser Arg Val Leu Tyr Pro Asn Asp Asn Phe Phe Glu
        275                 280                 285

Gly Lys Glu Leu Arg Leu Lys Gln Glu Tyr Phe Val Val Ala Ala Thr
    290                 295                 300

Leu Gln Asp Ile Ile Arg Arg Phe Lys Ser Ser Lys Phe Gly Cys Arg
305                 310                 315                 320

Asp Pro Val Arg Thr Asn Phe Asp Ala Phe Pro Asp Lys Val Ala Ile
                325                 330                 335

Gln Leu Asn Asp Thr His Pro Ser Leu Ala Ile Pro Glu Leu Met Arg
            340                 345                 350

Ile Leu Val Asp Leu Glu Arg Met Asp Trp Asp Lys Ala Trp Asp Val
        355                 360                 365

Thr Val Arg Thr Cys Ala Tyr Thr Asn His Thr Val Leu Pro Glu Ala
    370                 375                 380

Leu Glu Arg Trp Pro Val His Leu Leu Glu Thr Leu Leu Pro Arg His
385                 390                 395                 400

Leu Gln Ile Ile Tyr Glu Ile Asn Gln Arg Phe Leu Asn Arg Val Ala
                405                 410                 415

Ala Ala Phe Pro Gly Asp Val Asp Arg Leu Arg Arg Met Ser Leu Val
            420                 425                 430

Glu Glu Gly Ala Val Lys Arg Ile Asn Met Ala His Leu Cys Ile Ala
        435                 440                 445

Gly Ser His Ala Val Asn Gly Val Ala Arg Ile His Ser Glu Ile Leu
    450                 455                 460
```

```
Lys Lys Thr Ile Phe Lys Asp Phe Tyr Glu Leu Glu Pro His Lys Phe
465                 470                 475                 480
Gln Asn Lys Thr Asn Gly Ile Thr Pro Arg Arg Trp Leu Val Leu Cys
            485                 490                 495
Asn Pro Gly Leu Ala Glu Val Ile Ala Glu Arg Ile Gly Glu Asp Phe
        500                 505                 510
Ile Ser Asp Leu Asp Gln Leu Arg Lys Leu Leu Ser Phe Val Asp Asp
    515                 520                 525
Glu Ala Phe Ile Arg Asp Val Ala Lys Val Lys Gln Glu Asn Lys Leu
530                 535                 540
Lys Phe Ala Ala Tyr Leu Glu Arg Glu Tyr Lys Val His Ile Asn Pro
545                 550                 555                 560
Asn Ser Leu Phe Asp Ile Gln Val Lys Arg Ile His Glu Tyr Lys Arg
            565                 570                 575
Gln Leu Leu Asn Cys Leu His Val Ile Thr Leu Tyr Asn Arg Ile Lys
        580                 585                 590
Arg Glu Pro Asn Lys Phe Phe Val Pro Arg Thr Val Met Ile Gly Gly
        595                 600                 605
Lys Ala Ala Pro Gly Tyr His Met Ala Lys Met Ile Ile Arg Leu Val
610                 615                 620
Thr Ala Ile Gly Asp Val Val Asn His Asp Pro Ala Val Gly Asp Arg
625                 630                 635                 640
Leu Arg Val Ile Phe Leu Glu Asn Tyr Arg Val Ser Leu Ala Glu Lys
            645                 650                 655
Val Ile Pro Ala Ala Asp Leu Ser Glu Gln Ile Ser Thr Ala Gly Thr
        660                 665                 670
Glu Ala Ser Gly Thr Gly Asn Met Lys Phe Met Leu Asn Gly Ala Leu
        675                 680                 685
Thr Ile Gly Thr Met Asp Gly Ala Asn Val Glu Met Ala Glu Glu Ala
690                 695                 700
Gly Glu Glu Asn Phe Phe Ile Phe Gly Met Arg Val Glu Asp Val Asp
705                 710                 715                 720
Lys Leu Asp Gln Arg Gly Tyr Asn Ala Gln Glu Tyr Tyr Asp Arg Ile
            725                 730                 735
Pro Glu Leu Arg Gln Val Ile Glu Gln Leu Ser Ser Gly Phe Phe Ser
        740                 745                 750
Pro Lys Gln Pro Asp Leu Phe Lys Asp Ile Val Asn Met Leu Met His
        755                 760                 765
His Asp Arg Phe Lys Val Phe Ala Asp Tyr Glu Asp Tyr Ile Lys Cys
770                 775                 780
Gln Glu Lys Val Ser Ala Leu Tyr Lys Asn Pro Arg Glu Trp Thr Arg
785                 790                 795                 800
Met Val Ile Arg Asn Ile Ala Thr Ser Gly Lys Phe Ser Ser Asp Arg
            805                 810                 815
Thr Ile Ala Gln Tyr Ala Arg Glu Ile Trp Gly Val Glu Pro Ser Arg
        820                 825                 830
Gln Arg Leu Pro Ala Pro Asp Glu Ala Ile
        835                 840
```

<210> SEQ ID NO 67  
<211> LENGTH: 429  
<212> TYPE: PRT  
<213> ORGANISM: Homo sapiens

<400> SEQUENCE: 67

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
                20                  25                  30

Asp Asn Gly Leu Ala Arg Thr Pro Thr Met Gly Trp Leu His Trp Glu
            35                  40                  45

Arg Phe Met Cys Asn Leu Asp Cys Gln Glu Glu Pro Asp Ser Cys Ile
        50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415
```

```
Leu Glu Asn Thr Met Gln Met Ser Leu Lys Asp Leu Leu
            420                 425
```

```
<210> SEQ ID NO 68
<211> LENGTH: 952
<212> TYPE: PRT
<213> ORGANISM: Homo sapiens

<400> SEQUENCE: 68

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365
```

```
Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Val Glu Ala Leu Gly
770                 775                 780
```

```
Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
            850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
                915                 920                 925

Ser Pro Asp Thr Lys Val Leu Asp Ile Cys Val Ser Leu Leu Met Gly
            930                 935                 940

Glu Gln Phe Leu Val Ser Trp Cys
945                 950

<210> SEQ ID NO 69
<211> LENGTH: 210
<212> TYPE: PRT
<213> ORGANISM: Homo sapiens

<400> SEQUENCE: 69

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
                20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
            130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190
```

```
Ala Leu Lys Thr Lys Leu Asp Leu Ser Ser Leu Ala Tyr Ser Gly Lys
        195                 200                 205

Asp Ala
    210
```

ADENO-ASSOCIATED VIRUS VARIANT CAPSIDS AND METHODS OF USE THEREOF

CROSS-REFERENCE TO RELATED APPLICATIONS

This application is a continuation of U.S. patent application Ser. No. 16/648,195 filed Mar. 17, 2020, which is a 35 U.S.C. 371 national stage of International Application Number PCT/US2018/051812 filed Sep. 19, 2018, which claims the benefit of U.S. Provisional Patent Application Ser. No. 62/560,901, filed Sep. 20, 2017, the full disclosure of each of which are incorporated herein by reference.

SEQUENCE LISTING SUBMISSION VIA EFS-WEB

A computer readable text file, A computer readable text file, entitled "090400-5009-US-01-Sequence-Listing-ST25" created on or about Mar. 17, 2020, with a file size of about 290 KB contains the sequence listing for this application and is hereby incorporated by reference in its entirety.

FIELD OF THE INVENTION

The invention disclosed herein relates generally to the field of adeno-associated virus (AAV) virions comprising variant capsid proteins and the generation of such variant capsids using directed evolution techniques.

BACKGROUND OF THE DISCLOSURE

Muscle is associated with a variety of severe genetic disorders. Muscle is the target tissue in gene therapy for many muscular dystrophy diseases and also can be exploited as a biofactory to produce secretory factors to treat systemic disease. Delivering therapeutic genes to muscle tissue in human is arguably the most urgent unmet need in treating muscle-related diseases.

One approach to accomplish muscle-directed gene delivery is gene-based adeno-associated virus (AAV)-mediated therapy, in which a recombinant adeno associated virus (rAAV) is used to deliver a gene to one or more muscle cells, for example to replace a missing gene, to correct a dominant defective gene, or to provide a template for continuous protein therapy. While AAV-based clinical gene therapy has been increasingly successful, it is still fraught with shortcomings with regard to viral vector properties, including, for example, targeting the desired cells of the muscle with high efficiency. Accordingly, there is a need in the art for new AAV variants with superior transduction capabilities that will provide for more effective gene-based delivery to the cells of the muscle for the treatment of disease. There is a need in the art for such AAV variants which exhibit an enhanced muscle transduction profile—in some instances broadly, in other instances preferentially to certain muscle cell types—as compared to wild-type AAVs and AAV variants as known in the art.

Naturally occurring AAV is a single stranded DNA virus that contains three open reading frames, rep, cap, and aap. The first gene, rep, encodes four proteins necessary for genome replication (Rep78, Rep68, Rep52, and Rep40), the second, cap, expresses three structural proteins (VP1-3) that assemble to form the viral capsid, and the third expresses the assembly activating protein (AAP) that is essential for capsid assembly. AAV is dependent upon the presence of a helper virus, such as an adenovirus or herpesvirus, for active replication. In the absence of a helper virus, AAV establishes a latent state in which its genome is maintained episomally or integrated into the host chromosome in the AAVS1 locus.

J In vitro and in vivo directed evolution techniques may be used to select for AAV variants that offer an improvement over current AAV-based gene delivery vectors. Such directed evolution techniques are known in the art and described, e.g., in PCT publication WO 2014/194132 and Kotterman & Schaffer (Nature Review Genetics, AOP, published online 20 May 2014; doi: 10.1038/nrg3742), both of which are incorporated herein in their entirety by reference. Directed evolution is a capsid engineering approach that emulates natural evolution through iterative rounds of genetic diversification and selection processes, thereby enabling the accumulation of beneficial mutations that progressively improve the function of a biomolecule such as an AAV-based virion. In this approach, wild-type AAV cap genes are diversified to create large genetic libraries that are packaged to generate libraries of viral particles, and selective pressure is applied to isolate unique variants with superior phenotypes that can overcome gene delivery barriers.

AAV variants have been disclosed in, for example, U.S. Pat. Nos. 9,193,956; 9,186,419; 8,632,764; 8,663,624; 8,927,514; 8,628,966; 8,263,396; 8,734,809; 8,889,641; 8,632,764; 8,691,948; 8,299,295; 8,802,440; 8,445,267; 8,906,307; 8,574,583; 8,067,015; 7,588,772; 7,867,484; 8,163,543; 8,283,151; 8,999,678; 7,892,809; 7,906,111; 7,259,151; 7,629,322; 7,220,577; 8,802,080; 7,198,951; 8,318,480; 8,962,332; 7,790,449; 7,282,199; 8,906,675; 8,524,446; 7,712,893; 6,491,907; 8,637,255; 7,186,522; 7,105,345; 6,759,237; 6,984,517; 6,962,815; 7,749,492; 7,259,151; and 6,156,303; United States Publication Numbers 2013/0295614; 2015/0065562; 2014/0364338; 2013/0323226; 2014/0359799; 2013/0059732; 2014/0037585; 2014/0056854; 2013/0296409; 2014/03350542013/0195801; 20-12/0070899; 2011/0275529; 2011/0171262; 2009/0215879; 2010/0297177; 2010/0203083; 2009/0317417; 2009/0202490; 2012/0220492; 2006/0292117; and 2004/0002159; European Publication Numbers 2692731 A1; 2383346 B1; 2359865 B1; 2359866 B1; 2359867 B1; and 2357010 B1; 1791858 B1; 1668143 B1; 1660678 B1; 1664314 B1; 1496944 B1; 1456383 B1; 2341068 BL; 2338900 B; 1456419 B1; 1310571 B; 1456383 B1; 1633772 B1; and 1135468 B1; and International (PCT) Publication Numbers WO 2014/124282; WO 2013/170078; WO 2014/160092; WO 2014/103957; WO 2014/052789; WO 2013/174760; WO 2013/123503; WO 2011/038187; and WO 2008/124015; WO 2003/054197; however, none of these references disclose the embodiments and/or features and/or composition of matter structures of the AAV variants disclosed herein.

All documents and references cited herein and in the referenced patent documents, are hereby incorporated herein by reference.

SUMMARY OF THE INVENTION

Provided herein are variant adeno-associated virus (AAV) capsid proteins having one or more modifications in amino acid sequence relative to a parental AAV capsid protein, which, when present in an AAV virion, confer increased infectivity of one or more types of muscle cells as compared to the infectivity of the muscle cells by an AAV virion comprising an unmodified parental AAV capsid protein. Also provided are recombinant AAV virions and pharmaceutical compositions thereof comprising a variant AAV capsid protein as described herein, methods of making variant rAAV capsid proteins and virions, and methods for using these rAAV capsid proteins and virions in research and in clinical practice, for example in the delivery of nucleic acid sequences to one or more muscle cells for the treatment of disorders and diseases.

In some aspects of the disclosure, variant adeno-associated virus (AAV) capsid proteins are provided, these variant AAV capsid proteins having one or more modifications in amino acid sequence relative to a parental AAV capsid, which, when present in an AAV virion, confer increased infectivity of one or more types of muscle cells (e.g. skeletal muscle cells and/or cardiac muscle cells) as compared to the infectivity of the muscle cells by an AAV virion comprising a parental AAV capsid protein that does not comprise the amino acid sequence modification. In related aspects of the disclosure, the variant AAV capsid proteins, when present in an AAV virion also confer enhanced resistance to neutralization by anti-AAV antibodies.

In some aspects of the disclosure, recombinant AAV (rAAV) virions are provided, these rAAV virions comprising a variant capsid protein as described herein, wherein the rAAV virions exhibit increased infectivity of one or more types of muscle cells (e.g. skeletal muscle cells and/or cardiac muscle cells) relative to the infectivity of the muscle cell by an AAV virion comprising a corresponding unmodified parental AAV capsid protein. In some embodiments, the rAAV virion exhibits increased infectivity of all muscle cells relative to the AAV virion comprising the parental AAV capsid protein. In other embodiments, the rAAV virion exhibits increased infectivity of certain muscle cell types but not others relative of the AAV virion comprising the parental AAV capsid protein. Put another way, the rAAV virion exhibits increased infectivity that is preferential for certain muscle cell types but not others, e.g. the rAAV demonstrates a preferentially increased infectivity of one or more cell types selected from skeletal muscle fibroblasts, skeletal muscle satellite cells, cardiac fibroblasts, cardiac progenitor cells, smooth muscle cells and/or diaphragm muscle cells, but does not demonstrate increased infectivity of all cell types.

In some embodiments, the rAAV virion comprises a heterologous nucleic acid. In some such embodiments, the heterologous nucleic acid encodes an RNA that encodes a polypeptide. In other such embodiments, the heterologous nucleic acid sequence encodes an RNA that does not encode a polypeptide, e.g. the heterologous nucleic acid sequence is an RNA interference agent, a guide RNA for a nuclease, etc.

Also provided herein are pharmaceutical compositions comprising the subject infectious rAAV virions and a pharmaceutically acceptable carrier.

Also provided is the use of an rAAV virion comprising a variant capsid protein as herein described in a method of delivering a heterologous nucleic acid to a target cell (such as a cardiomyocyte) by contacting the target cell with the rAAV virion. In some embodiments, the target cell is in vivo, such as in the heart of an individual in need of treatment for a cardiovascular disorder. In other embodiments, the target cell is in vitro.

Also provided are methods of treating and/or preventing a disease (e.g. a cardiac or skeletal muscle disorder) by administering to a subject in need of such treatment an effective amount of rAAV virions comprising a variant capsid protein as herein described or a pharmaceutical composition comprising an effective amount of the rAAV virions.

Also provided is an isolated nucleic acid comprising a sequence encoding a variant AAV capsid protein as described herein and a host cell comprising the isolated nucleic acid. In yet other embodiments, the isolated nucleic acid and/or isolated host cell comprises the rAAV.

In some aspects, the variant AAV capsid protein comprises an insertion of from about 5 amino acids to about 20 amino acids (a "heterologous peptide", or "peptide insertion") in the GH-loop of the capsid protein, relative to a corresponding parental AAV capsid protein, wherein the variant capsid protein, when present in an AAV virion, confers increased infectivity of a muscle cell compared to the infectivity of a muscle cell by an AAV virion comprising the corresponding parental AAV capsid protein. In some embodiments, the peptide comprises or consists essentially of a sequence selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42). In some preferred embodiments, the peptide comprises or consists essentially of a sequence selected from the group consisting of NKIQRTD (SEQ ID NO:13), NKTTNKD (SEQ ID NO:14), TNKIGVT (SEQ ID NO:15), LANKIQRTDA (SEQ ID NO:27), LANKTTNKDA (SEQ ID NO:28), LATNKIGVTA (SEQ ID NO:29) and LATNKIGVTS (SEQ ID NO:37).

In some aspects, the variant AAV capsid protein comprises one or more amino acid substitutions relative to a corresponding parental AAV capsid protein, wherein the variant capsid protein, when present in an AAV virion, confers increased infectivity of a muscle cell compared to the infectivity of a muscle cell by an AAV virion comprising the corresponding parental AAV capsid protein.

In some embodiments, a variant AAV capsid protein is disclosed comprising a P363L substitution relative to AAV2 and optionally further comprising an E347K and/or V708I substitution relative to AAV2.

In related aspects, the variant AAV capsid protein comprises a peptide insertion and one or more amino acid substitutions relative to a corresponding parental AAV capsid protein, wherein the variant capsid protein, when present in an AAV virion, confers increased infectivity of a muscle cell compared to the infectivity of a muscle cell by an AAV virion comprising the corresponding parental AAV capsid protein. In several embodiments, a variant AAV capsid protein is provided comprising a peptide insertion and a V708I substitution relative to AAV2, wherein the peptide insertion is optionally selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTINKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID N0:42), preferably from the group consisting of NKIQRTD (SEQ ID NO:13), NKTTNKD (SEQ ID NO:14), TNKIGVT (SEQ ID NO:15), LANKIQRTDA (SEQ ID NO:27), LANKTTNKDA (SEQ ID NO:28), LATNKIGVTA (SEQ ID N0:29) and LATNKIGVTS (SEQ ID NO:37). In several embodiments, a variant AAV capsid protein is provided comprising a peptide insertion and a P363L substitution relative to AAV2, wherein the peptide insertion is optionally selected from the group consisting of GNLTKGN (SEQ ID NO:16), LAGNLTKGNA (SEQ ID NO:30), QADTTKN (SEQ ID NO:23) and LAQADTTKNA (SEQ ID NO:39).

In some embodiments, a variant AAV capsid protein is disclosed comprising the heterologous peptide LANKIQRTDA (SEQ ID NO:27) and a V708I substitution relative to AAV2 and optionally further comprising an A593E and/or S109T and/or T330A and/or R588M substitution relative to AAV2. In other embodiments, a variant AAV capsid protein is disclosed comprising the heterologous peptide LANKIQRTDA (SEQ ID NO:27) and an A35P substitution relative to AAV2. In other embodiments, a variant AAV capsid protein is disclosed comprising the heterologous peptide LANKIQRTDA (SEQ ID NO:27) and amino acid substitutions N312K, N449D, N551S, I698V, and L735Q relative to AAV2 and optionally further comprising a V708I substitution relative to AAV2.

In some embodiments, a variant AAV capsid protein is disclosed comprising the heterologous peptide LANKTTNKDA (SEQ ID NO:28) and a V708I substitution relative to AAV2 and optionally further comprising an S109T and/or W694C and/or W606C substitution relative to AAV2. In other embodiments, a variant AAV capsid protein is disclosed comprising the heterologous peptide LANKTTNKDA (SEQ ID NO:28) and an I698V substitution relative to AAV2. In other embodiments, a variant AAV capsid protein is disclosed comprising the heterologous peptide LANKTTNKDA (SEQ ID NO:28) and amino acid substitutions N312K, N449D, N551S, I698V, and L735Q relative to AAV2 and optionally further comprising a V708I substitution relative to AAV2.

In some embodiments, a variant AAV capsid protein is disclosed comprising the heterologous peptide LATNKIGVTA (SEQ ID NO:29) and a V708I substitution relative to AAV2 and optionally further comprising an N449K and/or G222S substitution relative to AAV2. In other embodiments, a variant AAV capsid protein is disclosed comprising the heterologous peptide LATNKIGVTA (SEQ ID NO:29) and amino acid substitutions N312K, N449D, N551S, I698V, and L735Q relative to AAV2 and optionally further comprising a V708I substitution relative to AAV2.

In some embodiments, a variant AAV capsid protein is disclosed comprising a heterologous peptide as described herein and a P363L substitution relative to AAV2.

Also disclosed herein are methods for manufacture and/or delivery of an rAAV comprising a variant AAV capsid as disclosed herein. In addition, provided herein are kits comprising an rAAV comprising a variant AAV capsid as disclosed herein and for use in methods described herein.

In other embodiments, the AAV virion comprising the variant capsid protein in the preceding paragraphs may incorporate any of the preceding or subsequently disclosed embodiments. Indeed, it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the invention and are disclosed herein just as if each and every combination was individually and explicitly disclosed. In addition, all sub-combinations of the various embodiments and elements thereof are also specifically embraced by the invention and are disclosed herein just as if each and every such sub-combination was individually and explicitly disclosed herein.

The Summary of the Invention is not intended to define the claims nor is it intended to limit the scope of the invention in any manner.

Other features and advantages of the invention disclosed herein will be apparent from the following Figures, Detailed Description, and the Claims.

BRIEF DESCRIPTION OF THE FIGURES

It is emphasized that, according to common practice, the various features of the drawings are not to-scale. On the contrary, the dimensions of the various features are arbitrarily expanded or reduced for clarity. Included in the drawings are the following figures.

FIGS. 3A-3C show frequency of motifs within sequencing analysis. FIG. 3A provides Round 4 sequencing analysis for the selective pressure of intravenous delivery to cardiac tissue. FIG. 3B provides Round 2 sequencing analysis for the selective pressure of intravenous delivery in the presence of neutralizing antibodies to cardiac tissue. FIG. 3C provides Round 3 sequencing analysis for the selective pressure of intravenous delivery to skeletal muscle tissue. FIG. 3A shows 57.40% LANKIQRTDA (SEQ ID NO: 27) Motif, 16.96% LANKTTNKDA (SEQ ID NO: 28) Motif, 7.32% A593E Motif, 7.32% Other, 4.88% V708I Motif and 4.88% LASNTVKAIA (SEQ ID NO: 32) Motif. FIG. 3B shows 21.14% Other, 20.33% LAQADTTKNA (SEQ ID NO: 39) Motif, 15.45% LANKTTNKDA (SEQ ID NO: 28) Motif, 15.45% LAASNITKAA (SEQ ID NO: 33) Motif, 15.45% AAV6/AAV5 Chimera Motif and 12.20% LANTVKLSTA (SEQ ID NO: 31) Motif. FIG. 3C shows 43.21% A593E Motif, 41.98% P363L Motif and 14.81% Other.

FIG. 4B is a representative three-dimensional model of the AAV6/AAV5 chimera containing V229I, A490T, and A581T substitutions (corresponding to the amino acid sequence set forth as SEQ ID NO:62). FIG. 4C is a representative three-dimensional model of AAV2 containing a P363L substitution.

FIG. 5 provides an alignment of wild-type AAV SEQ ID NOS:1-11 showing amino acid locations between and across the wild-type (naturally occurring) serotypes AAV1, AAV2, AAV3A, AAV3B, and AAV4-10.

FIGS. 6A-6E provide data on the transduction of human cardiomyocytes in vitro by recombinant AAV virus comprising the novel AAV variant LANKIQRTDA+V708I (SEQ ID NO:43) capsid, the novel AAV variant LANKTTNKDA+V708I (SEQ ID NO:48) capsid, and the novel LATNKIGVTA+V708I (SEQ ID NO:46) variant capsid, each expressing a GFP transgene under the control of the CAG promoter. FIG. 6A: Cells that were differentiated into cardiomyocytes from a human pluripotent stem cell line were infected with novel AAV variant LANKIQRTDA+V708I (SEQ ID NO:43).CAG.GFP, novel AAV variant LANKTTNKDA+V708I (SEQ ID NO:48).CAG.GFP, novel AAV variant LATNKIGVTA+V708I (SEQ ID NO:46).CAG.GFP or wild type controls AAV1.CAG.GFP, AAV2.CAG.GFP, and AAV9.CAG.GFP at MOIs of 20, 100, 500, and 2500. Immunofluorescence imaging of the cell cultures 6 days after infection at all MOIs demonstrate that the novel AAV variant capsids transduce cardiomyocytes better than wild type AAV1, AAV2, or AAV9 capsids. FIG. 6B: Quantification of the percent of GFP-positive cardiomyocytes in each culture by flow cytometry reveals that the novel AAV variant capsids provide for a significant, dose-dependent improvement in the number of cells transduced over wild type AAV1, AAV2, or AAV9 capsids. * p<0.05 FIGS. 6C-6D: Quantification of the amount of GFP in each culture by Western blot reveals that the novel AAV variants provide for significant improvement in expression of the transgene over wild type AAV1, AAV2, or AAV9 capsids. NT=not transduced. FIG. 6E: Cells that were differentiated into cardiomyocytes from a human pluripotent stem cell line were infected with novel AAV variant LANKIQRTDA+V708I (SEQ ID NO:43).CAG.GFP, novel AAV variant LANKTTNKDA+V708I (SEQ ID NO:48).CAG.GFP, novel AAV variant LATNKIGVTA+V708I (SEQ ID NO:46).CAG.GFP or wild type controls AAV1.CAG.GFP, AAV2.CAG.GFP, and AAV9.CAG.GFP. Immunofluorescence imaging of the cell cultures on days 1, 2, 3, and 5 after infection at an MOI of 500 demonstrate that the novel AAV variant capsids transduce cardiomyocytes better and begin expressing the GFP transgene earlier than wild type AAV1, AAV2, or AAV9 capsids.

FIGS. 7A-E provide data on the transduction of human cardiomyocytes in vitro by recombinant AAV virus comprising the novel AAV variant AAV6/AAV5 chimera capsid of SEQ ID NO: 62, expressing a GFP transgene under the control of the CAG promoter. FIG. 7A: Cells that were differentiated into cardiomyocytes from a human pluripotent stem cell line were infected with novel AAV variant AAV6/AAV5 chimera capsid or wild type controls AAV1.CAG.GFP, AAV8.CAG.GFP, and AAV9.CAG.GFP at MOIs of 100, 500, and 2500. Immunofluorescence imaging of the cell cultures 6 days after infection at all MOIs demonstrate that the novel AAV variant capsid transduces cardiomyocytes better than wild type AAV1, AAV8, or AAV9 capsids. FIG. 7B: Quantification of the percent of GFP-positive cardiomyocytes in each culture by flow cytometry reveals that the novel AAV variant capsid provides for a significant, dose-dependent improvement in the number of cells transduced over wild type AAV1, AAV8, or AAV9 capsids. * p<0.05 FIGS. 7C-7D: Quantification of the amount of GFP in each culture by Western blot reveals that the novel AAV variant provides for significant improvement in expression of the transgene over wild type AAV1, AAV8, or AAV9 capsids. vehicle=not transduced. FIG. 7E: Cells that were differentiated into cardiomyocytes from a human pluripotent stem cell line were infected with novel AAV variant AAV6/AAV5 chimera capsid or wild type control AAV8.CAG.GFP. Immunofluorescence imaging of the cell cultures on days 3, 4, 5, and 6 after infection at an MOI of 2500 demonstrate that the novel AAV variant capsids transduce cardiomyocytes better and begin expressing the GFP transgene earlier than the wild type AAV8 capsid.

FIG. 8A: Cells that were differentiated into skeletal myofibers from human primary myoblasts were infected with novel AAV variant LANKIQRTDA+V708I (SEQ ID NO:43).CAG.GFP, novel AAV variant LANKTTNKDA+V708I (SEQ ID NO:48).CAG.GFP, novel AAV variant AAV6/AAV5 chimera.CAG.GFP or wild type controls AAV8.CAG.GFP and AAV9.CAG.GFP at MOIs of 100, 500, and 2500. Immunofluorescence imaging of the cell cultures 7 days after infection at all MOIs demonstrate that the novel AAV variant capsids transduce skeletal myofibers better than wild type AAV8 or AAV9 capsids. FIG. 8B: Quantification of the percent of GFP-positive skeletal myofibers in each culture by flow cytometry reveals that the novel AAV variant capsids provide for a significant, dose-dependent improvement in the number of cells transduced over wild type AAV8 or AAV9 capsids. * p<0.05 FIG. 8C: Cells that were differentiated into skeletal myofibers from human primary myoblasts were infected with novel AAV variant LANKIQRTDA+V708I (SEQ ID NO:43).CAG.GFP, novel AAV variant AAV6/AAV5 chimera.CAG.GFP or wild type controls AAV8.CAG.GFP and AAV9.CAG.GFP. Immunofluorescence imaging of the cell cultures on days 2-7 after infection at an MOI of 2500 demonstrate that the novel AAV variant capsids transduce skeletal myofibers better and begin expressing the GFP transgene earlier than wild type AAV8 or AAV9 capsids.

FIG. 9A: Cells that were differentiated into muscle progenitor cells from a human pluripotent stem cell line were infected with novel AAV variant LANKIQRTDA+ V708I (SEQ ID NO:43).CAG.GFP, novel AAV variant LANKTTNKDA+V708I (SEQ ID NO:48).CAG.GFP, novel AAV variant AAV6/AAV5 chimera.CAG.GFP or wild type control AAV9.CAG.GFP at an MOI of 500. Immunofluorescence imaging of the cell cultures 6 days after infection at all MOIs demonstrate that the novel AAV variant capsids transduce muscle progenitor cells better than wild type AAV9. FIG. 9B: Quantification of the percent of GFP-positive muscle progenitor cells in each culture by flow cytometry reveals that the novel AAV variant capsids provide for a significant improvement in the number of cells transduced over wild type AAV9. * p<0.05

FIGS. 10A-B provide data on the magnitude of improvement of transduction of human cardiomyocytes and human skeletal myofibers in vitro by recombinant AAV virus comprising the novel AAV variant LANKIQRTDA+V708I (SEQ ID NO:43) capsid, the novel AAV variant LANKTTNKDA+ V708I (SEQ ID NO:48) capsid, and the novel AAV variant AAV6/AAV5 chimera capsid, each expressing a GFP transgene under the control of the CAG promoter. FIG. 10A: Fold increase in transduction of human cardiomyocytes by the novel AAV capsid variants compared to wild type AAV8 and AAV9, the serotypes most widely used in clinical applications for muscle diseases. FIG. 10B: Fold increase in transduction of human skeletal myofibers by the novel AAV capsid variants compared to wild type AAV8 and AAV9.

FIG. 11A: In life imaging of luciferase at day 14 (left) and day 28 (right) post-administration demonstrate that the novel AAV variant LANKIQRTDA+ V708I (SEQ ID NO:43) capsid can transduce mouse cells in vivo. FIG. 11B: Luciferase activity in heart, diaphragm, and quadriceps 56 days post-administration demonstrate that the novel AAV variant LANKIQRTDA+V708I (SEQ ID NO:43) capsid can transduce mouse cardiac and skeletal muscle in vivo.

FIG. 12A: Representative images of haemotoxylin and eosin (H&E) and anti-GFP antibody staining of cross-sections of the proximal biopsy site at 2×, 4×, and 20× magnification demonstrate that the novel AAV variant LANKIQRTDA+ V708I (SEQ ID NO:43) capsid can transduce primate skeletal muscle cells in vivo. FIG. 12B: Representative images of haemotoxylin and eosin (H&E) and anti-GFP antibody staining of longitudinal sections of the distal biopsy site at 2×, 4×, and 20× magnification demonstrate that the novel AAV variant LANKIQRTDA+V708I (SEQ ID NO:43) capsid can transduce primate skeletal muscle cells in vivo.

DETAILED DESCRIPTION

Figure 1:
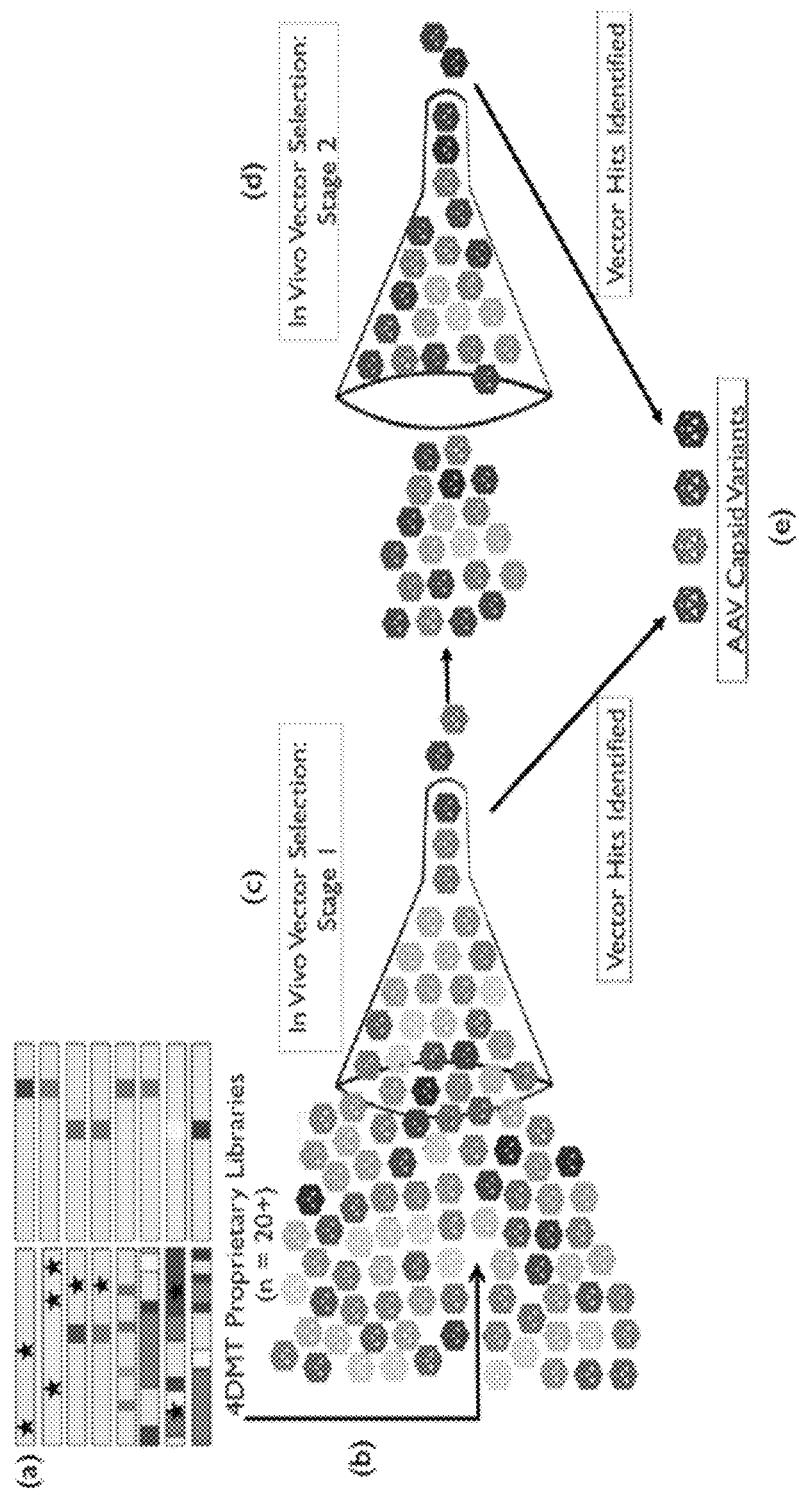
FIG. 1 depicts embodiments of a directed evolution methodology. Step (a) depicts the generation of a viral capsid library comprising combinations of DNA mutation techniques and cap genes. Step (b) depicts the packaging of the viruses such that each viral particle is composed of a mutant capsid surrounding the cap gene encoding that capsid and purified. The capsid library is then placed under selective pressure in vitro or in vivo. In this aspect of the directed evolution technology, tissues or cellular material of interest are harvested for isolation of AAV variants that have successfully infected that target, and the successful viruses are recovered. Step (c) depicts the Stage 1 enrichment of successful clones through repeated selection. Step (d) depicts the Stage 2 enrichment of selected cap genes which undergo re-diversification and further selection steps to iteratively increase viral fitness. Step (e) depicts the variants, identified as hits during Vector Selection Stages 1 and 2, which will be manufactured as recombinant AAV vectors and characterized for the level of transduction of various cell types and tissue targets. By the nature of the AAV directed evolution process, variants that are disclosed herein have already demonstrated the ability to transduce muscle cells and deliver a genome (the genome encoding the variant cap gene) during the selection process.

Before the present methods and compositions are described, it is to be understood that this invention is not limited to a particular method or composition described and as such may vary. It is also to be understood that the terminology used herein is for the purpose of describing particular embodiments only, and is not intended to be limiting, since the scope of the present invention will be limited only by the appended claims.

The invention disclosed herein is illustrated in the figures and description. However, while particular embodiments are illustrated in the figures, there is no intention to limit the invention to the specific embodiment or embodiments illustrated and/or disclosed. Rather, the invention disclosed herein is intended to cover all modifications, alternative constructions, and equivalents falling within the spirit and scope of the invention. As such, the figures are intended to be illustrative and not restrictive.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is noted that as used herein and in the appended claims, the singular forms "a," "an," and "the" include plural referents unless the context clearly dictates otherwise. Thus, for example, reference to "a recombinant AAV virion" includes a plurality of such virions and reference to "the muscle cell" includes reference to one or more muscle cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Adeno-associated virus is a nonpathogenic parvovirus composed of a 4.7 kb single-stranded DNA genome within a non-enveloped, icosahedral capsid. The genome contains three open reading frames (ORF) flanked by inverted terminal repeats (ITR) that function as the viral origin of replication and packaging signal. The rep ORF encodes four nonstructural proteins that play roles in viral replication, transcriptional regulation, site-specific integration, and virion assembly. The cap ORF encodes three structural proteins (VP 1-3) that assemble to form a 60-mer viral capsid. Finally, an ORF present as an alternate reading frame within the cap gene produces the assembly-activating protein (AAP), a viral protein that localizes AAV capsid proteins to the nucleolus and functions in the capsid assembly process.

There are several naturally occurring ("wild-type") serotypes and over 100 known variants of AAV, each of which differs in amino acid sequence, particularly within the hypervariable regions of the capsid proteins, and thus in their gene delivery properties. No AAV has been associated with any human disease, making recombinant AAV attractive for clinical applications.

For the purposes of the disclosure herein, the terminology "AAV" is an abbreviation for adeno-associated virus, including, without limitation, the virus itself and derivatives thereof. Except where otherwise indicated, the terminology refers to all subtypes or serotypes and both replication-competent and recombinant forms. The term "AAV" includes, without limitation, AAV type 1 (AAV-1 or AAV1), AAV type 2 (AAV-2 or AAV2), AAV type 3A (AAV-3A or AAV3A), AAV type 3B (AAV-3B or AAV3B), AAV type 4 (AAV-4 or AAV4), AAV type 5 (AAV-5 or AAV5), AAV type 6 (AAV-6 or AAV6), AAV type 7 (AAV-7 or AAV7), AAV type 8 (AAV-8 or AAV8), AAV type 9 (AAV-9 or AAV9), AAV type 10 (AAV-10 or AAV10 or AAVrh10), avian AAV, bovine AAV, canine AAV, caprine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077.1 (AAV1), AF063497.1 (AAV1), NC_001401.2 (AAV2), AF043303.1 (AAV2), J01901.1 (AAV2), U48704.1 (AAV3A), NC_001729.1 (AAV3A), AF028705.1 (AAV3B), NC_001829.1 (AAV4), U89790.1 (AAV4), NC_006152.1 (AA5), AF085716.1 (AAV-5), AF028704.1 (AAV6), NC_006260.1 (AAV7), AF513851.1 (AAV7), AF513852.1 (AAV8) NC_006261.1 (AAV-8), AY530579.1 (AAV9), AAT46337 (AAV10) and AAO88208 (AAVrh10); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et. al. (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303.

The sequences of naturally existing cap (capsid) proteins associated with AAV serotypes are known in the art and include those disclosed herein as AAV1 (SEQ ID NO:1), AAV2 (SEQ ID NO:2), AAV3A (SEQ ID NO:3), AAV3B (SEQ ID NO:4), AAV4 (SEQ ID NO:5), AAV5 (SEQ ID NO:6), AAV6 (SEQ ID NO:7), AAV7 (SEQ ID NO:8), AAV8 (SEQ ID NO:9), AAV9 (SEQ ID NO:10), AAV10 (SEQ ID NO:11), and AAVrh10 (SEQ ID NO:12). The terms "variant AAV capsid protein" or "AAV variant" refer to an AAV capsid protein comprising an amino acid sequence that includes at least one modification or substitution (including deletion, insertion, point mutation, etc.) relative to a naturally existing or "wild-type" AAV capsid protein sequences, e.g. as set forth in SEQ ID NO:1-12 herein. A variant AAV capsid protein may have about 80% identity or more to the amino acid sequence of a wild type capsid protein, for example, 85% identity or more, 90% identity or more, or 95% identity or more to the amino acid sequence of the wild type capsid protein, for example, 98% or 99% identity to the wild type capsid protein. A variant AAV capsid protein may not be a wild type capsid protein.

For the purposes of the disclosure herein, "AAV virion" or "AAV viral particle" refers to a viral particle composed of at least one AAV capsid protein and an encapsidated AAV polynucleotide.

For the purposes of the disclosure herein, the terminology "rAAV" is an abbreviation that refers to recombinant adeno-associated virus. "Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

The term "rAAV vector" encompasses rAAV virions (i.e., rAAV viral particles) (e.g., an infectious rAAV virion), which by definition include an rAAV polynucleotide; and also encompasses polynucleotides encoding rAAV (e.g., a single stranded polynucleotide encoding rAAV (ss-rAAV); a double stranded polynucleotide encoding rAAV (ds-rAAV), e.g., plasmids encoding rAAV; and the like).

If an AAV virion comprises a heterologous polynucleotide (i.e. a polynucleotide other than a wild-type AAV genome, e.g., a transgene to be delivered to a target cell, an RNAi agent or CRISPR agent to be delivered to a target cell, etc.), it is typically referred to as a "recombinant AAV (rAAV) virion" or an "rAAV viral particle." In general, the heterologous polynucleotide is flanked by at least one, and generally by two, AAV inverted terminal repeat sequences (ITRs).

The term "packaging" refers to a series of intracellular events that result in the assembly and encapsidation of an AAV particle. AAV "rep" and "cap" genes refer to polynucleotide sequences encoding replication and encapsidation proteins of adeno-associated virus. AAV rep and cap are referred to herein as AAV "packaging genes."

The terminology "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

The terminology "helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

The terminology "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles, Methods of determining the ratio of infectious viral particle to total viral particle are known in the art. See, e.g., Grainger et al. (2005) Mol. Ther. 11: S337 (describing a TCID50 infectious titer assay); and Zolotukhin et al. (1999) Gene Ther. 6:973. See also the Examples.

The term "tropism" as used herein refers to the preferential targeting by a virus (e.g., an AAV) of cells of a particular host species or of particular cell types within a host species. For example, a virus that can infect cells of the heart, lung, liver, and muscle has a broader (i.e., increased) tropism relative to a virus that can infect only lung and muscle cells. Tropism can also include the dependence of a virus on particular types of cell surface molecules of the host. For example, some viruses can infect only cells with surface glycosaminoglycans, while other viruses can infect only cells with sialic acid (such dependencies can be tested using various cells lines deficient in particular classes of molecules as potential host cells for viral infection). In some cases, the tropism of a virus describes the virus's relative preferences. For example, a first virus may be able to infect all cell types but is much more successful in infecting those cells with surface glycosaminoglycans. A second virus can be considered to have a similar (or identical) tropism as the first virus if the second virus also prefers the same characteristics (e.g., the second virus is also more successful in infecting those cells with surface glycosaminoglycans), even if the absolute transduction efficiencies are not similar. For example, the second virus might be more efficient than the first virus at infecting every given cell type tested, but if the relative preferences are similar (or identical), the second virus can still be considered to have a similar (or identical) tropism as the first virus. In some embodiments, the tropism of a virion comprising a subject variant AAV capsid protein is not altered relative to a naturally occurring virion. In some embodiments, the tropism of a virion comprising a subject variant AAV capsid protein is expanded (i.e., broadened) relative to a naturally occurring virion. In some embodiments, the tropism of a virion comprising a subject variant AAV capsid protein is reduced relative to a naturally occurring virion.

The terminology "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per 10 rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment herein that comprises a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

J The term "gene" refers to a polynucleotide that performs a function of some kind in the cell. For example, a gene can contain an open reading frame that is capable of encoding a gene product. One example of a gene product is a protein, which is transcribed and translated from the gene. Another example of a gene product is an RNA, e.g. a functional RNA product, e.g., an aptamer, an interfering RNA, a ribosomal RNA (rRNA), a transfer RNA (tRNA), a non-coding RNA (ncRNA), a guide RNA for nucleases, etc., which is transcribed but not translated.

The terminology "gene expression product" or "gene product" is a molecule resulting from expression of a particular gene, as defined above. Gene expression products include, e.g., a polypeptide, an aptamer, an interfering RNA, a messenger RNA (mRNA), an rRNA, a tRNA, a non-coding RNA (ncRNA), and the like.

The term "siRNA agent" ("small interfering" or "short interfering RNA" (or siRNA)) is an RNA duplex of nucleotides that is targeted to a gene of interest (a "target gene"). An "RNA duplex" refers to the structure formed by the complementary pairing between two regions of a RNA molecule, forming a region of double stranded RNA (dsRNA). siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. In some embodiments, siRNA-mediated gene targeting is accomplished through the use of DNA-directed RNA interference (ddRNAi) which is a gene-silencing technique that utilizes DNA constructs to activate an animal cell's endogenous RNA interference (RNAi) pathways. Such DNA constructs are designed to express self-complementary double-stranded RNAs, typically short-hairpin RNAs (shRNA), that once processed bring about silencing of a target gene or genes. Any RNA, including endogenous mRNAs or viral RNAs, can be silenced by designing constructs to express double-stranded RNA complementary to the desired mRNA target. As such, the RNA duplex portion of an siRNA agent can be part of a short hairpin structure referred to as shRNA. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. In general, the level of expression product (e.g., mRNA, polypeptide, etc.) of a target gene is reduced by an siRNA agent (e.g., an siRNA, an shRNA, etc.) that contains specific double stranded nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO 00/44895, WO 99/32619, WO 01/75164, WO 01/92513, WO 01/29058, WO 01/89304, WO 02/16620, and WO 02/29858; and U.S. Patent Publication No. 2004/0023390 for descriptions of siRNA technology. The siRNA and/or shRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The terminology "antisense RNA" encompasses RNA that is complementary to a gene expression product. For example, an antisense RNA targeted to a specific mRNA is an RNA-based agent (or can be a modified RNA) that is complementary to the mRNA, where hybridization of the antisense RNA to the mRNA alters the expression of the mRNA (e.g., via altering the stability of the RNA, altering the translation of the RNA, etc.). Also included in "antisense RNA" are nucleic acids encoding an antisense RNA.

With regards to "CRISPR/Cas9 agents", the term "CRISPR" encompasses Clustered regularly interspaced short palindromic repeats/CRISPR-associated (Cas) systems that evolved to provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on association of the protein with two naturally occurring or synthetic RNA molecules called crRNA and tracrRNA (also called guide RNAs). In some cases, the two molecules are covalently linked to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence.

If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Cas9-like proteins with decreased DNA-cleavage activity (even no DNA-cleaving activity) can still be guided to a target DNA to block RNA polymerase activity. Alternatively, the Cas9 or Cas9-like protein may be modified by fusing a VP64 transcription activation domain to the Cas9 protein and codelivering the fusion protein with a MS2-P65-HSF1 helper protein and a single guide RNA comprising MS2 RNA aptamers at the tetraloop and stem-loop to form a Synergistic Activation Mediator (Cas9-SAM) complex in the cell that activates transcription. Thus enzymatically inactive Cas9-like proteins can be targeted to a specific location in a target DNA by a DNA-targeting RNA in order to block or activate transcription of the target DNA. The term "CRISPR/Cas9 agents" as used herein encompasses all forms of CRISPR/Cas9 as described above or as known in the art.

Detailed information regarding CRISPR agents can be found, for example in (a) Jinek et. al., Science. 2012 Aug. 17; 337(6096):816-21: "A programmable dual-RNA-guided DNA endonuclease in adaptive bacterial immunity"; (b) Qi et al., Cell. 2013 Feb. 28; 152(5): 1173-83: "Repurposing CRISPR as an RNA-guided platform for sequence-specific control of gene expression", and (c) U.S. patent application Ser. No. 13/842,859 and PCT application number PCT/US13/32589; all of which are hereby incorporated by reference in their entirety. Thus, the term "CRISPR agent" as used herein encompasses any agent (or nucleic acid encoding such an agent), comprising naturally occurring and/or synthetic sequences, that can be used in the Cas9-based system (e.g., a Cas9 or Cas9-like protein; any component of a DNA-targeting RNA, e.g., a crRNA-like RNA, a tracrRNA-like RNA, a single guide RNA, etc.; a donor polynucleotide; and the like).

By "Zinc-finger nucleases" (ZFNs) it is meant artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. For more information on the use of ZFNs, see, for example: Asuri et al., Mol. Ther. 2012 February; 20(2): 329-38; Bibikova et al. Science. 2003 May 2; 300(5620): 764; Wood et al. Science. 2011 Jul. 15; 333(6040):307; Ochiai et al. Genes Cells. 2010 August; 15(8):875-85; Takasu et. al., Insect Biochem Mol Biol. 2010 October; 40(10):759-65; Ekker et al, Zebrafish 2008 Summer; 5(2): 121-3; Young et al, Proc Natl Acad Sci USA. 2011 Apr. 26; 108(17):7052-7; Goldberg et al, Cell. 2010 Mar. 5; 140(5): 678-91; Geurts et al, Science. 2009 Jul. 24; 325(5939):433; Flisikowska et al, PLoS One. 2011; 6 (6):e21045. doi: 10.1371/journal.pone.0021045. Epub 2011 Jun. 13; Hauschild et al, Proc Natl Acad Sci USA. 2011 Jul. 19; 108(29): 12013-7; and Yu et al, Cell Res. 2011 November; 21(11): 1638-40; all of which are herein incorporated by reference for their teachings related to ZFNs. The term "ZFN agent" encompasses a zinc finger nuclease and/or a polynucleotide comprising a nucleotide sequence encoding a zinc finger nuclease.

The terminology "Transcription activator-like effector nuclease" or "TALEN" agents refers to Transcription activator-like effector nucleases (TALENs). TALENs are artificial DNA endonucleases generated by fusing a TAL (Transcription activator-like) effector DNA binding domain to a DNA cleavage domain. TALENs can be quickly engineered to bind practically any desired DNA sequence and when introduced into a cell, TALENs can be used to edit target DNA in the cell (e.g., the cell's genome) by inducing double strand breaks. For more information on the use of TALENs, see, for example: Hockemeyer et al. Nat Biotechnol. 2011 Jul. 7; 29(8):731-4; Wood et al. Science. 2011 Jul. 15; 333(6040):307; Tesson et al. Nat Biotechnol. 2011 Aug. 5; 29(8):695-6; and Huang et. al., Nat Biotechnol. 2011 Aug. 5; 29(8):699-700; all of which are herein incorporated by reference for their teachings related to TALENs. The term "TALEN agent" encompasses a TALEN and/or a polynucleotide comprising a nucleotide sequence encoding a TALEN.

The terminology "control element" or "control sequence" refers to a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters may be ubiquitously acting, i.e. active in many cell types, e.g. CAG or CMV promoters; or tissue or cell specific, e.g. the promoter can be tissue-specific for expression in cardiomyocytes.

The terminology "operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The terminology "expression vector" encompasses a vector comprising a polynucleotide region which encodes a polypeptide of interest, and is used for effecting the expression of the protein in an intended target cell. An expression vector may also comprise control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid sequence encoding a heterologous gene product is an rAAV that includes a polynucleotide not normally included in a naturally-occurring, wild-type AAV, and the encoded heterologous gene product is a gene product not normally encoded by a naturally-occurring, wild type AAV.

The terminology "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

With regards to cell modification, the terminology "genetically modified" or "transformed" or "transfected" or "transduced" by exogenous DNA (e.g. via a recombinant virus) refers to when such DNA has been introduced inside the cell. The presence of the exogenous DNA results in permanent or transient genetic change. The transforming DNA may or may not be integrated (covalently linked) into the genome of the cell. A "clone" is a population of cells derived from a single cell or common ancestor by mitosis.

A "cell line" is a clone of a primary cell that is capable of stable growth in vitro for many generations.

As used herein, a cell is said to be "stably" altered, transduced, genetically modified, or transformed with a genetic sequence if the sequence is available to perform its function during extended culture of the cell in vitro and/or for an extended period of time in vivo. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

As used herein, an "isolated" plasmid, nucleic acid, vector, virus, virion, host cell, protein, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease (and/or symptoms caused by the disease) from occurring in a subject which may be predisposed to the disease or at risk of acquiring the disease but has not yet been diagnosed as having it; (b) inhibiting the disease (and/or symptoms caused by the disease), i.e., arresting its development; and (c) relieving the disease (and/or symptoms caused by the disease), i.e., causing regression of the disease (and/or symptoms caused by the disease), i.e., ameliorating the disease and/or one or more symptoms of the disease. For example, the subject compositions and methods may be directed towards the treatment of muscle disease. Nonlimiting methods for assessing muscle diseases and the treatment thereof include measuring therapeutic protein production (e.g. muscle biopsy followed by immunohistochemistry or serum sampling followed by ELISA or enzyme activity assays), measuring symptoms of heart failure (e.g. the New York Heart Association Functional Classification or the Minnesota Living With Heart Failure Questionnaire), functional cardiac status (e.g. the 6-minute walk test or peak maximum oxygen consumption), biomarker analysis (e.g. N-terminal prohormone brain natriuretic peptide), left ventricular function/remodeling (e.g. left ventricular ejection fraction or left ventricular end-systolic volume), muscle strength (e.g. the Medical Research Council Scales Clinical Investigation of Duchenne Dystrophy, hand-held dynamometry, or maximum weight lift), muscle function (e.g. the Vignos Scale, Timed Function Tests, the Hammersmith Motor Ability Score, timed rise from floor, walk tests, Motor Function Measure Scale, North Star Ambulatory Assessment, 9 Hole Peg Test, or Children's Hospital of Philadelphia Infant Test of Neuromuscular Disorders), muscle disease symptoms (e.g. the Neuromuscular Symptoms Score or Clinical Global Impressions), mitochondrial function (e.g. $^{31}P$ magnetic resonance spectroscopy), questionnaire-based assessments of quality of life, patient-reported outcomes, or daily activities.

The terms "individual," "host," "subject," and "patient" are used interchangeably herein, and refer to a mammal, including, but not limited to, humans; non-human primates, including simians; mammalian sport animals (e.g., horses); mammalian farm animals (e.g., sheep, goats, etc.); mammalian pets (dogs, cats, etc.); and rodents (e.g., mice, rats, etc.).

In some embodiments, the individual is a human who has previously been naturally exposed to AAV and as a result harbors anti-AAV antibodies (i.e., AAV neutralizing antibodies). In some embodiments, the individual is a human who has previously been administered an AAV vector (and as a result may harbor anti-AAV antibodies) and needs re-administration of vector for treatment of a different condition or for further treatment of the same condition. Based on positive results in clinical trials involving AAV gene delivery to, for example, liver, muscle, and retina—all tissues affected by neutralizing antibodies against this vehicle—there are many such therapeutic applications/disease targets.

The term "effective amount" as used herein is an amount sufficient to effect beneficial or desired clinical results. An effective amount can be administered in one or more administrations. For purposes of this disclosure, an effective amount of a compound (e.g., an infectious rAAV virion) is an amount that is sufficient to palliate, ameliorate, stabilize, reverse, prevent, slow or delay the progression of (and/or symptoms associated with) a particular disease state (e.g., a muscle disease). Accordingly, an effective amount of an infectious rAAV virion is an amount of the infectious rAAV virion that is able to effectively deliver a heterologous nucleic acid to a target cell (or target cells) of the individual. Effective amounts may be determined preclinically by, e.g., detecting in the cell or tissue the gene product (RNA, protein) that is encoded by the heterologous nucleic acid sequence using techniques that are well understood in the art, e.g. RT-PCR, western blotting, ELISA, fluorescence or other reporter readouts, and the like. Effective amounts may be determined clinically by, e.g. detecting a change in the onset or progression of disease using methods known in the art, e.g. 6-minute walk test, left ventricular ejection fraction, hand-held dynamometry, Vignos Scale and the like as described herein and as known in the art.

The terminology "muscle cell" or "muscle tissue" refers herein to a cell or group of cells derived from muscle of any kind, including, without limitation, skeletal muscle, cardiac muscle, smooth muscle (e.g. from the digestive tract, urinary bladder and blood vessels) and diaphragm muscle. Such muscle cells may be differentiated or undifferentiated such as myoblasts, myocytes, myotubes, cardiomyocytes, and cardiomyoblasts. Since muscle tissue is readily accessible to the circulatory system, a protein produced and secreted by muscle cells and tissue in vivo will logically enter the bloodstream for systemic benefit, thereby providing sustained, therapeutic levels of protein secretion from the muscle.

The terminology "directed evolution" refers to a capsid engineering methodology, in vitro and/or in vivo, which emulates natural evolution through iterative rounds of genetic diversification and selection processes, thereby accumulating beneficial mutations that progressively improve the function of a biomolecule. Directed evolution often involves an in vivo method referred to as "biopanning" for selection of AAV variants from a library which variants possess a more efficient level of infectivity of a cell or tissue type of interest.

DETAILED DESCRIPTION

Adeno-associated viruses (AAVs) are a family of parvoviruses with a 4.7 kb single-stranded DNA genome contained inside a non-enveloped capsid. The viral genome of a naturally occurring AAV has 2 inverted terminal repeats (ITR)—which function as the viral origin of replication and packaging signal flanking 2 primary open reading frames (ORF): rep (encoding proteins that function in viral replication, transcriptional regulation, site-specific integration, and virion assembly) and cap. The cap ORF codes for 3 structural proteins that assemble to form a 60-mer viral capsid. Many naturally occurring AAV variants and serotypes have been isolated, and none have been associated with human disease.

Recombinant versions of AAV can be used as gene delivery vectors, where a marker or therapeutic gene of interest is inserted between the ITRs in place of rep and cap. These vectors have been shown to transduce both dividing and non-dividing cells in vitro and in vivo and can result in stable transgene expression for years in post-mitotic tissue. See e.g., Knipe D M, Howley P M. *Fields' Virology*. Lippincott Williams & Wilkins, Philadelphia, PA, USA, 2007; Gao G-P, Alvira M R, Wang L, Calcedo R, Johnston J, Wilson J M. Novel adeno-associated viruses from rhesus monkeys as vectors for human gene therapy. *Proc Natl Acad Sci USA* 2002; 99: 11854-9; Atchison R W, Casto B C, Hammon W M. Adenovirus-Associated Defective Virus Particles. *Science* 1965; 149: 754-6; Hoggan M D, Blacklow N R, Rowe W P. Studies of small DNA viruses found in various adenovirus preparations: physical, biological, and immunological characteristics. *Proc Natl Acad Sci USA* 1966; 55: 1467-74; Blacklow N R, Hoggan M D, Rowe W P. Isolation of adenovirus-associated viruses from man. *Proc Natl Acad Sci USA* 1967; 58: 1410-5; Bantel-Schaal U, zur Hausen H. Characterization of the DNA of a defective human parvovirus isolated from a genital site. *Virology* 1984; 134: 52-63; Mayor H D, Melnick J L Small deoxyribonucleic acid-containing viruses (picodnavirus group). *Nature* 1966; 210: 331-2; Mori S, Wang L, Takeuchi T, Kanda T. Two novel adeno-associated viruses from cynomolgus monkey: pseudotyping characterization of capsid protein. *Virology* 2004; 330: 375-83; Flotte T R. Gene therapy progress and prospects: recombinant adeno-associated virus (rAAV) vectors. *Gene Ther* 2004; 11: 805-10.

Recombinant AAV (referred to herein simply as "AAV") has yielded promising results in an increasing number of clinical trials. However, there are impediments to gene delivery that may limit AAV's utility, such as anti-capsid immune responses, low transduction of certain tissues, an inability for targeted delivery to specific cell types and a relatively low carrying capacity. In many situations, there is insufficient mechanistic knowledge to effectively empower rational design with the capacity to improve AAV. As an alternative, directed evolution has emerged as a strategy to create novel AAV variants that meet specific biomedical needs. Directed evolution strategies harness genetic diversification and selection processes to enable the accumulation of beneficial mutations that progressively improve the function of a biomolecule. In this process, wild-type AAV cap genes are diversified by several approaches to create large genetic libraries that are packaged to generate libraries of viral particles, and selective pressure is then applied to isolate novel variants that can overcome gene delivery barriers. Importantly, the mechanistic basis underlying a gene delivery problem does not need to be known for directed evolution of function, which can thus accelerate the development of enhanced vectors.

Typically, the variants disclosed herein were generated through use of an AAV library and/or libraries. Such an AAV library or libraries is/are generated by mutating the cap gene, the gene which encodes the structural proteins of the AAV capsid, by a range of directed evolution techniques known by and readily available to the skilled artisan in the field of viral genome engineering. See e.g., Bartel et al. Am. Soc. Gene Cell Ther. 15$^{th}$ Annu. Meet. 20, S140 (2012); Bowles, D. et al. J. Virol. 77, 423-432 (2003); Gray et al. Mol. Ther. 18, 570-578 (2010); Grimm, D. et al. J. Virol. 82, 5887-5911; Koerber, J. T. et al. Mol. Ther. 16, 1703-1709 (2008); Li W. et al. Mol. Ther. 16, 1252-1260 (2008); Koerber, J. T. et al. Methods Mol. Biol. 434, 161-170 (2008); Koerber, J. T. et al. Hum. Gene Ther. 18, 367-378 (2007); and Koerber, J. T. et al. Mol. Ther. 17, 2088-2095 (2009). Such techniques, without limitation, are as follows: i) Error-prone PCR to introduce random point mutations into the AAV cap open reading frame (ORF) at a predetermined, modifiable rate; ii) In vitro or in vivo viral recombination or "DNA shuffling" to generate random chimeras of AAV cap genes to yield a gene library with multiple AAV serotypes; iii) Random peptide insertions at defined sites of the capsid by ligation of degenerate oligonucleotides in the cap ORF; iv) Defined insertions of peptide-encoding sequences into random locations of the AAV cap ORF using transposon mutagenesis; v) Replacing surface loops of AAV capsids with libraries of peptide sequences bioinformationally designed based on the level of conservation of each amino acid position among natural AAV serotypes and variants to generate "loop-swap" libraries; vi) Random amino acid substitution at positions of degeneracy between AAV serotypes to generate libraries of ancestral variants (Santiago-Ortiz et al., 2015); and a combination of such techniques thereof.

DNA shuffling generates chimeras which combine their parental properties in unique and, often beneficial, ways; however, some may be incapable of packaging which, in effect, reduces the diversity of the library. Concentration of diversity the library into specific region(s) of the capsid is achieved through peptide insertion techniques such as, without limitation, iii-iv) above. Diversity of the library is also concentrated into specific region(s) of the capsid in techniques such as v) above, and such concentration is directed onto multiple hypervariable regions, which lie on surface exposed loops, of the AAV capsid. While many of the techniques generate variant capsids with only a small area of the capsid mutated, these techniques can be paired with additional mutagenesis strategies to modify the full capsid.

Once the AAV library or libraries is/are generated, viruses are then packaged, such that each AAV particle is comprised of a mutant capsid surrounding a cap gene encoding that capsid, and purified. Variants of the library are then subjected to in vitro and/or in vivo selective pressure techniques known by and readily available to the skilled artisan in the field of AAV. See e.g., Maheshri, N. et al. Nature Biotech. 24, 198-204 (2006); Dalkara, D. et al. Sci. Transl. Med. 5, 189ra76 (2013); Lisowski, L. et al. Nature. 506, 382-286 (2013); Yang, L. et al. PNAS. 106, 3946-3951 (2009); Gao, G. et al. Mol. Ther. 13, 77-87 (2006); and Bell, P. et al. Hum. Gene. Ther. 22, 985-997 (2011). For example, without limitation, AAV variants can be selected using i) affinity columns in which elution of different fractions yields variants with altered binding properties; ii) primary cells—isolated from tissue samples or immortal cell lines that mimic the behavior of cells in the human body—which yield AAV variants with increased efficiency and/or tissue specificity; iii) animal models—which mimic a clinical gene therapy environment—which yield AAV variants that have successfully infected target tissue; iv) human xenograft models which yield AAV variants that have infected grafted human cells; and/or a combination of selection techniques thereof.

Once viruses are selected, they may be recovered by known techniques such as, without limitation, adenovirus-mediated replication, PCR amplification, Next Generation sequencing and cloning, and the like. Virus clones are then enriched through repeated rounds of the selection techniques and AAV DNA is isolated to recover selected variant cap genes of interest. Such selected variants can be subjected to further modification or mutation and as such serve as a new starting point for further selection steps to iteratively increase AAV viral fitness. However, in certain instances, successful capsids have been generated without additional mutation.

The AAV variants disclosed herein were generated at least in part through the use of in vivo directed evolution methodology, such as the techniques described above, involving the use of primate cardiac and skeletal muscle screens following intravenous administration. As such, the AAV variant capsids disclosed herein comprise one or more modifications in amino acid sequence that confer more efficient transduction of primate muscle cells than a corresponding parental AAV capsid protein. As used herein, a "corresponding parental AAV capsid protein" refers to an AAV capsid protein of the same wild-type or variant AAV serotype as the subject variant AAV capsid protein but that does not comprise the one or more amino acid sequence modifications of the subject variant AAV capsid protein. In particular embodiments, an AAV comprising a variant AAV capsid protein as herein described has systemic tropism toward cardiac muscle and/or multiple skeletal muscle groups throughout the body following systemic or tissue-targeted administration.

In some embodiments, the subject variant AAV capsid protein comprises a heterologous peptide of from about 5 amino acids to about 20 amino acids inserted by covalent linkage into an AAV capsid protein GH loop, or loop IV, relative to a corresponding parental AAV capsid protein. By the "GH loop," or loop IV, of the AAV capsid protein it is meant the solvent-accessible portion referred to in the art as the GH loop, or loop IV, of AAV capsid protein. For the GH loop/loop IV of AAV capsid, see, e.g., van Vliet et al. (2006) Mol. Ther. 14:809; Padron et al. (2005) J. Virol. 79:5047; and Shen et al. (2007) Mol. Ther. 15:1955. Thus, for example, the insertion site can be within about amino acids 411-650 of an AAV VP1 capsid protein. For example, the insertion site can be within amino acids 571-612 of AAV1 VP1, amino acids 570-611 of AAV2 VP1, within amino acids 571-612 of AAV3A VP1, within amino acids 571-612 of AAV3B VP1, within amino acids 569-610 of AAV4 VP1, within amino acids 560-601 of AAV5 VP1, within amino acids 571 to 612 of AAV6 VP1, within amino acids 572 to 613 of AAV7 VP1, within amino acids 573 to 614 of AAV8 VP1, within amino acids 571 to 612 of AAV9 VP1, or within amino acids 573 to 614 of AAV10 VP1, or the corresponding amino acids of any variant thereof. Those skilled in the art would know, based on a comparison of the amino acid sequences of capsid proteins of various AAV serotypes, where an insertion site "corresponding to amino acids of AAV2" would be in a capsid protein of any given AAV serotype. See also FIG. 5 for an alignment of wild-type AAV SEQ ID NOS:1-41 which provides amino acid locations between and across the wild-type (naturally occurring) serotypes AAV1, AAV2, AAV3A, AAV3B, and AAV4-10.

In certain embodiments, the insertion site is a single insertion site between two adjacent amino acids located between amino acids 570-614 of VP1 of any wild-type AAV serotype or AAV variant, e.g., the insertion site is between two adjacent amino acids located in amino acids 570-610, amino acids 580-600, amino acids 570-575, amino acids 575-580, amino acids 580-585, amino acids 585-590, amino acids 590-600, or amino acids 600-614, of VP1 of any AAV serotype or variant. For example, the insertion site can be between amino acids 580 and 581, amino acids 581 and 582, amino acids 583 and 584, amino acids 584 and 585, amino acids 585 and 586, amino acids 586 and 587, amino acids 587 and 588, amino acids 588 and 589, or amino acids 589 and 590. The insertion site can be between amino acids 575 and 576, amino acids 576 and 577, amino acids 577 and 578, amino acids 578 and 579, or amino acids 579 and 580. The insertion site can be between amino acids 590 and 591, amino acids 591 and 592, amino acids 592 and 593, amino acids 593 and 594, amino acids 594 and 595, amino acids 595 and 596, amino acids 596 and 597, amino acids 597 and 598, amino acids 598 and 599, or amino acids 599 and 600. For example, the insertion site can be between amino acids 587 and 588 of AAV2, between amino acids 590 and 591 of AAV1, between amino acids 588 and 589 of AAV3A, between amino acids 588 and 589 of AAV3B, between amino acids 584 and 585 of AAV4, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

In some embodiments, a peptide insertion disclosed herein has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. In another embodiment, a peptide insertion disclosed herein comprises from 1 to 4 spacer amino acids at the amino terminus (N-terminus) and/or at the carboxyl terminus (C-terminus)

of any one of the peptide insertions disclosed herein. Exemplary spacer amino acids include, without limitation, leucine (L), alanine (A), glycine (G), serine (S), threonine (T), and proline (P). In certain embodiments, a peptide insertion comprises 2 spacer amino acids at the N-terminus and 2 spacer amino acids at the C-terminus. In other embodiments, a peptide insertion comprises 2 spacer amino acids at the N-terminus and 1 spacer amino acids at the C-terminus.

The peptide insertions disclosed herein have not been previously described and/or inserted into an AAV capsid. Without wishing to be bound by theory, the presence of any of the disclosed peptide insertions may act to lower the variant capsid's affinity for heparin sulfate which could alter extracellular or intracellular steps within the viral transduction pathway. In addition, the peptide insertion motifs disclosed herein may confer enhanced transduction of muscle cells (e.g. cardiomyocytes) through the addition of a cell surface receptor binding domain.

In some preferred embodiments, the insertion peptide comprises an amino acid sequence of any one of the formulas below.

In some aspects, an insertion peptide can be a peptide of 7 to 10 amino acids in length, of Formula 1a:

$Y_1Y_2X_1X_2X_3X_4X_5X_6X_7Y_3$

Where each of $Y_1$-$Y_3$, if present, is independently selected from Ala, Leu,
Gly, Ser, Thr, Pro
$X_1$ is selected from Ala, Asn, Thr, Gly, Ser, Ala, Gln, and Asp
$X_2$ is selected from Lys, Asn, Thr, Ser, Ala, and Gln
$X_3$ is selected from Ile, Thr, Lys, Leu, Val, Asn, Asp, and Arg
$X_4$ is selected from Gin, Thr, Ile, Lys, Val, Ser, and Tyr
$X_5$ is selected from Arg, Asn, Gly, Lys, Leu, Thr, Ala, Ser, and Gln
$X_6$ is selected from Thr, Lys, Val, Gly, Ser, Ala, Arg, and Pro
$X_7$ is selected from Asp, Thr, Asn, Ile, Ala, and Ser.

In certain embodiments, the insertion peptide of Formula 1a comprises an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26). In other embodiments, the insertion peptide of Formula 1a does not comprise an amino acid sequence selected from NKTTNKD (SEQ ID NO:14), QADTTKN (SEQ ID NO:23), TNRTSPD (SEQ ID NO:24) and NQDYTKT (SEQ ID NO:22).

In other aspects, an insertion peptide can be a peptide of 7 to 10 amino a acids in length, of Formula 1b:

$Y_1Y_2X_1X_2X_3X_4X_5X_6X_7Y_3$

Where each of $Y_1$-$Y_3$, if present, is independently selected from Ala, Leu, Gly, Ser, Thr, Pro
$X_1$ is selected from Thr and Asn
$X_2$ is selected from Asn and Lys
$X_3$ is selected from Lys, Ile and Thr
$X_4$ is selected from Ile, Gin, and Thr
$X_5$ is selected from Gly, Arg and Asn
$X_6$ is selected from Val, Thr and Lys
$X_7$ is selected from Thr and Asp In certain embodiments, the insertion peptide of Formula 1b comprises an amino acid sequence selected from NKIQRTD (SEQ ID NO:13), NKTTNKD (SEQ ID NO:14) and TNKIGVT (SEQ ID NO:15). In other embodiments, the insertion peptide of Formula 1a does not comprise the amino acid sequence NKTTNKD (SEQ ID NO:14).

In other aspects, an insertion peptide can be a peptide of 7 to 10 amino acids in length, of Formula 1c $Y_1Y_2X_1X_2X_3X_4X_5X_6X_7Y_3$ Where each of $Y_1$-$Y_3$, if present, is independently selected from Ala, Leu, Gly, Ser, Thr, Pro
$X_1$ is selected from Thr and Asn
$X_2$ is selected from Asn and Lys
$X_3$ is selected from Lys and Ile
$X_4$ is selected from Ile and Gin
$X_5$ is selected from Gly and Arg
$X_6$ is selected from Val and Thr
$X_7$ is selected from Thr and Asp In certain embodiments, the insertion peptide of Formula 1c comprises an amino acid sequence selected from NKIQRTD (SEQ ID NO:13) and TNKIGVT (SEQ ID NO:15).

In other aspects, an insertion peptide can be a peptide of 7 to 10 amino acids in length, of Formula 1d:

$Y_1Y_2X_1X_2X_3X_4X_5X_6X_7Y_3$

Where each of $Y_1$-$Y_3$, if present, is independently selected from Ala, Leu, Gly, Ser, Thr, Pro
$X_1$ is selected from Asn and Thr
$X_2$ is selected from Asn and Lys
$X_3$ is selected from Lys and Thr
$X_4$ is selected from Ile and Thr
$X_5$ is selected from Gly, Lys and Thr
$X_6$ is selected from Lys, Arg and Val
$X_7$ is selected from Asp, Thr and Asn In certain embodiments, the insertion peptide of Formula 1d comprises the amino acid sequence TNKIGVT (SEQ ID NO:15).

In other embodiments, the insertion peptide comprises an amino acid sequence selected from NKIQRTD (SEQ ID NO:13), NKTTNKD (SEQ ID NO:14) and TNKIGVT (SEQ ID NO:15). In related embodiments, the insertion peptide comprises an amino acid sequence selected from NKIQRTD (SEQ ID NO:13) and TNKIGVT (SEQ ID NO:15).

In some embodiments, the insertion peptide comprises an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26).

In other preferred embodiments, the insertion peptide has from 1 to 3 spacer amino acids ($Y_1$-$Y_3$) at the amino and/or carboxyl terminus of an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26). In certain such embodiments, the insertion peptide is selected from the group consisting of: LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33). LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

In some embodiments, the subject variant AAV capsid protein does not include any other amino acid sequence modifications other than a peptide insertion of from about 5 amino acids to about 20 amino acids in the GH loop, or loop IV. For example, in some embodiments, the subject variant AAV capsid protein comprises a peptide insertion comprising an amino acid sequence selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), and the variant AAV capsid does not include any other amino acid substitutions, insertions, or deletions (i.e., the variant AAV capsid protein comprises said insertion and is otherwise identical to the corresponding AAV capsid protein). Put another way, the variant AAV capsid protein comprising said insertion is otherwise identical to the parental AAV capsid protein into which the peptide has been inserted. As another example, the subject variant AAV capsid protein comprises a peptide insertion comprising an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), wherein the peptide insertion is located between amino acids 587 and 588 of the VP1 of the AAV2 capsid; between amino acids 588 and 589 of VP1 of AAV3A, AAV3B, AAV9, or AAV10; between amino acids 589 and 590 of VP1 of AAV7; between amino acids 590 to 591 of VP1 of AAV1, AAV6, or AAV8, between amino acids 584 and 585 of VP1 of AAV4, or between amino acids 575 and 576 of AAV5, wherein the variant AAV capsid protein sequence is otherwise identical to the corresponding parental AAV capsid protein sequence, e.g. any one of SEQ ID NOs:1-12.

In other embodiments, the subject variant AAV capsid protein, in addition to comprising a peptide insertion, e.g. as disclosed herein or as known in the art, in the GH loop, comprises from about 1 to about 100 amino acid substitutions or deletions, e.g. 1 to about 5, from about 2 to about 4, from about 2 to about 5, from about 5 to about 10, from about 10 to about 15, from about 15 to about 20, from about 20 to about 25, from about 25-50, from about 50-100 amino acid substitutions or deletions compared to the parental AAV capsid protein. Thus, in some embodiments, a subject variant capsid protein comprises an amino acid sequence having a sequence identity of 85% or more, 90% or more, 95% or more, or 98% or more, e.g. or 99% identity to the corresponding parental AAV capsid, e.g. a wild type capsid protein as set forth in SEQ ID NOs:1-12.

In a further embodiment, the one or more amino acid substitutions are at amino acid residue(s) 35, 109, 195, 213, 222, 229, 312, 319, 330, 333, 347, 363, 427, 447, 449, 453, 490, 527, 551, 581, 585, 588, 593, 606, 649, 651, 694, 698, 708, and/or 735 of AAV2 VP1 capsid protein as numbered prior to insertion of the peptide, or the corresponding amino acid residue(s) of another AAV capsid protein. In some such embodiments, the one or more amino acid substitutions are selected from the group consisting of A35P, S109T, P195L, D213N, G222S, V229I, N312K, A319T, T330A, A333S, E347K, P363L, A427D, V447F, N449D, N449K, G453R, A490T, K527Q, N551S, A581T, Y585S, R588M, A593E, W606C, K649E, R651H, W694C, I698V, V708I, and L735Q of AAV2 VP1 capsid protein as numbered prior to the insertion of the peptide, or the corresponding amino acid residue(s) of another AAV capsid protein.

In a preferred embodiment, a variant AAV capsid protein is provided comprising a) a peptide insertion in the GH-loop of the capsid protein, wherein the peptide insertion comprises an amino acid sequence selected from NKIQRTD (SEQ ID NO:13), NKTTNKD (SEQ ID NO:14) and TNKIGVT (SEQ ID NO:15), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: A35P, S109T, P195L, D213N, G222S, V229I, N312K, A319T, T330A, A333S, E347K, P363L, A427D, V447F, N449D, N449K, G453R, A490T, K527Q, N551S, A581T, Y585S, R588M, A593E, W606C, K649E, R651H, W694C, I698V, V708I, L735Q and a combination thereof. In some embodiments, the one or more amino acid substitutions are selected from the group consisting of: V708I, V708I+A593E, V708I+S109T, V708I+T330A, A35P, V708I+R588M, V708I+W606C, V708I+W694C, I698V, N312K+N449D+N551S+I698V+L735Q, N312K+N449D+N551S+I698V+V708I+L735Q, V708I+N449K, and V708I+G222S. Preferably, the peptide insertion site is located between amino acids 587 and 588 of AAV2 capsid, between amino acids 587 and 588 of AAV2 capsid, between amino acids 588 and 589 of AAV3A, AAV3B, AAV9, or AAV10 capsid, between amino acids 589 and 590 of AAV7 capsid, between amino acids 590 to 591 of AAV1, AAV6, or AAV8 capsid, between amino acids 584 and 585 of AAV4 capsid, or between amino acids 575 and 576 of AAV5 capsid.

In a particularly preferred embodiment, the variant AAV capsid comprises a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of VP1 of AAV2 or the corresponding amino acids of another AAV capsid, and further comprises a V708I amino acid substitution at residue 708 relative to the amino acid sequence of AAV2 capsid (SEQ ID NO:2) and optionally further comprises an A593E and/or S109T and/or T330A and/or R588M substitution relative to AAV2 or the corresponding substitutions in another AAV parental serotype, wherein the substituted amino acid(s) do not naturally occur at the corresponding position. In another particularly preferred embodiment, the variant AAV capsid comprises a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of VP1 of AAV2 or the corresponding amino acids of another AAV capsid, and further comprises an A35P amino acid substitution at residue 35 relative to the amino acid sequence of AAV2 capsid (SEQ ID NO:2) or the corresponding substitution in another AAV parental serotype. The variant AAV capsid may have at least about 85%, at least about 90%, at least about 95%, at least about 98%, or at least about 99%, or greater, amino acid sequence identity to the entire length of the amino acid sequence set forth in SEQ ID NO:2 or the corresponding parental AAV capsid. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 43)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANKIQRTDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSINVDFTVDTNGVYSEPRPIGTRYLTRNL

In another particularly preferred embodiment, the variant AAV capsid comprises a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid protein or the corresponding position in the capsid protein of another AAV serotype and comprises an N312K amino acid substitution compared to the amino acid sequence of AAV2 capsid (SEQ ID NO:2) or the corresponding substitution in another AAV parental serotype and optionally further comprises (i) N449D, N551S, I698V and L735Q or (ii) N449D, N551S, I698V, L735Q and V708I amino acid substitutions compared to the amino acid sequence of AAV2 capsid or the corresponding substitutions in another AAV parental serotype. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 44)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLKFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTDT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

SVDIEKVMITDEEEIRTTNPVATEQYGSVSTNLQRGNLANKIQRTDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEVQYTSNYNKSVNVDFTVDTNGVYSEPRPIGTRYLTRNQ

In another embodiment, a variant AAV capsid protein is provided comprising a) a peptide insertion located between amino acids 588 and 589 of VP1 of AAV3A, AAV3B, AAV9, or AAV10, between amino acids 589 and 590 of AAV7, between amino acids 590 to 591 of AAV1, AAV6 or AAV8, between amino acids 584 and 585 of AAV4 or between amino acids 575 and 576 of AAV5, the peptide insertion comprising an amino acid sequence selected from NKIQRTD (SEQ ID NO:13) and LANKIQRTDA (SEQ ID NO:27), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5 and is optionally otherwise identical to any one of SEQ ID NOs: 1 and 3-12. In preferred embodiments, the variant capsid protein comprises a) a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid and b) a valine to isoleucine amino acid substitution at amino acid 708 compared to the amino acid sequence of AAV2, wherein the variant capsid protein comprises from 2 to 5, from 5 to 10, or from 10 to 15 amino acid substitutions.

In yet another embodiment, the variant capsid protein comprises a) a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In yet another embodiment, the variant capsid protein comprises a) a peptide insertion comprising the amino acid sequence NKIQRTD (SEQ ID NO:13) or comprising, consisting essentially of, or consisting of the amino acid sequence LANKIQRTDA (SEQ ID NO:27) between amino acids 587 and 588 of AAV2 capsid and is otherwise identical to the amino acid sequence of SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 45)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANKIQRTDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In another particularly preferred embodiment, the variant AAV capsid comprises a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid or the corresponding position in the capsid protein of another AAV serotype and comprises a V708I amino acid substitution compared to the amino acid sequence of AAV2 or the corresponding substitution in another AAV parental serotype and optionally further comprises an N449K and/or G222S substitution relative to AAV2 or the corresponding substitution in the capsid protein of another AAV parental serotype, wherein the substituted amino acids do not naturally occur at the corresponding position. In another preferred embodiment, the variant AAV capsid comprises a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid or the corresponding position in the capsid protein of another AAV serotype and comprises N312K, N449D, N551S, I698V and L735Q and optionally V708I amino acid substitutions compared to the amino acid sequence of AAV2 or the corresponding substitution(s) in another AAV parental serotype, wherein the substituted amino acid(s) do not naturally occur at the corresponding position. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 46)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLATNKIGVTARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKS<u>I</u>NVDFTVDTNGVYSEPRPIGTRYLTRNL

In another embodiment, a variant AAV capsid protein is provided comprising a) a peptide insertion located between amino acids 588 and 589 of VP1 of AAV3A, AAV3B, AAV9, or AAV10, between amino acids 589 and 590 of AAV7, between amino acids 590 to 591 of AAV1, AAV6 or AAV8, between amino acids 584 and 585 of AAV4 or between amino acids 575 and 576 of AAV5, the peptide insertion comprising an amino acid sequence selected from TNKIGVT (SEQ ID NO:15), LATNKIGVTA (SEQ ID NO:29) and LATNKIGVTS (SEQ ID NO:37), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In preferred embodiments, the variant AAV capsid comprises a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid and comprises a valine to isoleucine amino acid substitution at amino acid 708 (V708I) compared to the amino acid sequence of AAV2, wherein the variant capsid protein comprises from 2 to 5, from 5 to 10, or from 10 to 15 amino acid substitutions and is preferably at least about 85%, at least about 90%, at least about 95%, at least about 98%, or greater amino acid sequence identity to the entire length of the amino acid sequence set forth in SEQ ID NO:2.

In yet another embodiment, the variant capsid protein comprises a) a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In yet another embodiment, the variant capsid protein comprises a) a peptide insertion comprising the amino acid sequence TNKIGVT (SEQ ID NO:15) or comprising, consisting essentially of, or consisting of the amino acid sequence LATNKIGVTA (SEQ ID NO:29) or LATNKIGVTS (SEQ ID NO:37) between amino acids 587 and 588 of AAV2 capsid and is otherwise identical to the amino acid sequence of SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 47)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLATNKIGVTARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In another preferred embodiment, the variant AAV capsid comprises a peptide insertion comprising the amino acid sequence NKTTNKD (SEQ ID NO:14) or LANKTTNKDA (SEQ ID NO:28) between amino acids 587 and 588 of AAV2 capsid and further comprises a V708I amino acid substitution at residue 708 relative to the amino acid sequence of AAV2 capsid (SEQ ID NO:2) or the corresponding substitution in another AAV parental serotype and optionally further comprises an S109T and/or W694C and/or W606C amino acid substitution compared to the amino acid sequence of AAV2 or the corresponding substitution in another AAV parental serotype, wherein the substituted amino acid(s) do not naturally occur at the corresponding position. In another particularly preferred embodiment, the variant AAV capsid comprises a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of VP1 of AAV2 or the corresponding amino acids of another AAV capsid, and further comprises an I698V amino acid substitution at residue 698 relative to the amino acid sequence of AAV2 capsid (SEQ ID NO:2) or the corresponding residue of another AAV capsid. The variant AAV capsid may have at least about 85%, at least about 90%, at least about 95%, at least about 98%, or greater amino acid sequence identity to the entire length of the amino acid sequence set forth in SEQ ID NO:2 or the corresponding parental AAV capsid. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 48)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANKTTNKDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSI̱NVDFTVDTNGVYSEPRPIGTRYLTRNL

In another particularly preferred embodiment, the variant AAV capsid comprises a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid protein or the corresponding position in the capsid protein of another AAV serotype and comprises an N312K amino acid substitution compared to the amino acid sequence of AAV2 capsid (SEQ ID NO:2) or the corresponding substitution in another AAV parental serotype and optionally further comprises N449D, N551S, I698V, and L735Q and optionally V708I amino acid substitutions compared to the amino acid sequence of AAV2 capsid or the corresponding substitutions in another AAV parental serotype. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 49)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLKFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTDT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

SVDIEKVMITDEEEIRTTNPVATEQYGSVSTNLQRGNLANKTTNKDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEVQYTSNYNKSVNVDFTVDTNGVYSEPRPIGTRYLTRNQ

In another embodiment, a variant AAV capsid protein is provided comprising a) a peptide insertion located between amino acids 588 and 589 of VP1 of AAV3A, AAV3B, AAV9, or AAV10, between amino acids 589 and 590 of AAV7, between amino acids 590 to 591 of AAV1, AAV6 or AAV8, between amino acids 584 and 585 of AAV4 or between amino acids 575 and 576 of AAV5, the peptide insertion comprising an amino acid sequence selected from NKTTNKD (SEQ ID NO:14) and LANKTINKDA (SEQ ID NO:28), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5 and is optionally otherwise identical to any one of SEQ ID NOs: 1 and 3-12. In preferred embodiments, the variant capsid protein comprises a) a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid and b) a valine to isoleucine amino acid substitution at amino acid 708 compared to the amino acid sequence of AAV2, wherein the variant capsid protein comprises from 2 to 5, from 5 to 10, or from 10 to 15 amino acid substitutions.

In yet another embodiment, the variant capsid protein comprises a) a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In another embodiment, the variant capsid comprises a peptide insertion comprising the amino acid sequence NKTTNKD (SEQ ID NO:14) or comprising, consisting essentially of, or consisting of the amino acid sequence LANKTTNKDA (SEQ ID NO:28) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 50)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANKTTNKDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In other embodiments, a variant AAV capsid protein is provided comprising a) a peptide insertion in the GH-loop of the capsid protein, wherein the peptide insertion comprises an amino acid sequence selected from GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25) and ASDSTKA (SEQ ID NO:26), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: A35P, S109T, P195L, D213N, G222S, V229I, N312K, A319T, T330A, A333S, E347K, P363L, A427D, V447F, N449D, N449K, G453R, A490T, K527Q, N551S, A581T, Y585S, R588M, A593E, W606C, K649E, R651H, W694C, I698V, V708I, L735Q and a combination thereof. In some embodiments, the one or more amino acid substitutions are selected from the group consisting of: V708I, S109T, R651H, A319T, P195L, P363L, I698V, D213N, G453R and a combination thereof. In some preferred embodiments, the one or more amino acid substitutions include at least a V708I and/or P363L amino acid substitution or the corresponding substitution in another AAV parental serotype. Preferably, the peptide insertion site is located between amino acids 587 and 588 of AAV2 capsid or the corresponding position in the capsid protein of another AAV serotype.

In some embodiments, the variant AAV capsid comprises a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and further comprises one or more of the following amino acid substitutions relative to the amino acid sequence of AAV2 capsid (SEQ ID NO:2) or the corresponding substitution in another AAV parental serotype, wherein the substituted amino acid(s) do not naturally occur at the corresponding positions: V708I, V708I+S109T, R651H, A319T+P195L, P363L, P363L+V708I. In some embodiments, the variant AAV capsid comprises (i) a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and (ii) a V708I substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and (ii) a P363L substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of VP1 of AAV2 or the corresponding amino acids of another AAV capsid and (ii) an R651H substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence GNLTKGN (SEQ ID NO:16) or comprising, consisting essentially of, or consisting of the amino acid sequence LAGNLTKGNA (SEQ ID NO:30) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

```
                                          (SEQ ID NO: 51)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAGNLTKGNARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL
```

In some embodiments, the variant AAV capsid comprises (i) a peptide insertion comprising the amino acid sequence NTVKLST (SEQ ID NO:17) or comprising, consisting essentially of, or consisting of the amino acid sequence LANTVKLSTA (SEQ ID NO:31) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) the corresponding substitution in another AAV parental serotype, wherein the substituted amino acid(s) do not naturally occur at the corresponding positions, and comprises from 2 to 5, from 5 to 10, or from 10 to 15 amino acid substitutions or is otherwise identical to the amino acid sequence of SEQ ID NO:2 or to the corresponding parental AAV capsid protein sequence. In another embodiment, the variant capsid comprises a peptide insertion comprising the amino acid sequence NTVKLST (SEQ ID NO:17) or comprising, consisting essentially of, or consisting of the amino acid sequence LANTVKLSTA (SEQ ID NO:31) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

```
                                          (SEQ ID NO: 52)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP
```

-continued

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANTVKLSTARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence SNTVKAI (SEQ ID NO:18) or comprising, consisting essentially of, or consisting of the amino acid sequence LASNTVKAIA (SEQ ID NO:32) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence SNTVKAI (SEQ ID NO:18) or comprising, consisting essentially of, or consisting of the amino acid sequence LASNTVKAIA (SEQ ID NO:32) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 53)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

-continued
NVDIEKVMITDEEEIRTTNPVATEQYGSVSTNLQRGNLASNTVKAIARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence ASNITKA (SEQ ID NO:19) or comprising, consisting essentially of, or consisting of the amino acid sequence LAASNITKAA (SEQ ID NO:33) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence ASNITKA (SEQ ID NO:19) or comprising, consisting essentially of, or consisting of the amino acid sequence LAASNITKAA (SEQ ID NO:33) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 54)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAASNITKAARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence DNTVTRS (SEQ ID NO:20) or comprising, consisting essentially of, or consisting of the amino acid sequence LADNTVTRSA (SEQ ID NO:34) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence DNTVTRS (SEQ ID NO:20) or comprising, consisting essentially of, or consisting of the amino acid sequence LADNTVTRSA (SEQ ID NO:34) between amino acids 587 and 588 of VP1 of AAV2 or the corresponding amino acids of another AAV capsid and (ii) an I698V amino acid substitution relative to the amino acid sequence of AAV2 capsid (SEQ ID NO:2) or the corresponding substitution in another AAV parental serotype, wherein the substituted amino acid does not naturally occur at the corresponding position, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence DNTVTRS (SEQ ID NO:20) or comprising, consisting essentially of, or consisting of the amino acid sequence LADNTVTRSA (SEQ ID NO:34) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 55)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLADNTVTRSARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence NKISAKD (SEQ ID NO:21) or comprising, consisting essentially of, or consisting of the amino acid sequence LANKISAKDA (SEQ ID NO:35) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence NKISAKD (SEQ ID NO:21) or comprising, consisting essentially of, or consisting of the amino acid sequence LANKISAKDA (SEQ ID NO:35) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 56)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANKISAKDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence NQDYTKT (SEQ ID NO:22) or comprising, consisting essentially of, or consisting of the amino acid sequence LANQDYTKTA (SEQ ID NO:36) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding substitution in another AAV parental serotype and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence NQDYTKT (SEQ ID NO:22) or comprising, consisting essentially of, or consisting of the amino acid sequence LANQDYTKTA (SEQ ID NO:36) between amino acids 587 and 588 of VP1 of AAV2 or the corresponding amino acids of another AAV capsid and (ii) an I698V amino acid substitution relative to the amino acid sequence of AAV2 capsid (SEQ ID NO:2) or the corresponding substitution in another AAV parental serotype (i.e. other than AAV2), wherein the substituted amino acid does not naturally occur at the corresponding position, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In another embodiment, the variant capsid comprises a peptide insertion comprising the amino acid sequence NQDYTKT (SEQ ID NO:22) or comprising, consisting essentially of, or consisting of the amino acid sequence LANQDYTKTA (SEQ ID NO:36) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 57)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANQDYTKTARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and further comprises one or more of the following amino acid substitutions relative to the amino acid sequence of AAV2 capsid (SEQ ID NO:2) or the corresponding substitutions in another AAV parental serotype, wherein the substituted amino acid(s) do not naturally occur at the corresponding positions: V708I, D213N, P363L, G453R. In some embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a V708I substitution relative to the amino acid sequence of AAV2 capsid (SEQ ID NO:2) or the corresponding substitution in another AAV parental serotype and comprises from 2, to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a P363L substitution relative to the amino acid sequence of AAV2 capsid (SEQ ID NO:2) or the corresponding residue of another AAV capsid and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a D213N substitution relative to the amino acid sequence of AAV2 capsid (SEQ ID NO:2) or the corresponding substitution in another AAV parental serotype, and comprises from 2 to 5, from 5 to 10, or from 10 to 15 amino acid substitutions or is otherwise identical to the amino acid sequence of SEQ ID NO:2 or the to the corresponding parental AAV capsid protein sequence. In other embodiments, the variant AAV capsid comprises (i) a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of VP1 of AAV2 or the corresponding amino acids of another AAV capsid and (ii) a G453R substitution relative to the amino acid sequence of AAV2 capsid (SEQ ID NO:2) or the corresponding substitution in another AAV parental serotype and comprises from 2 to 5, from 5 to 10, or from 10 to 15 amino acid substitutions or is otherwise identical to the amino acid sequence of SEQ ID NO:2 or to the corresponding parental AAV capsid protein sequence. In another embodiment, the variant capsid comprises a peptide insertion comprising the amino acid sequence QADTTKN (SEQ ID NO:23) or comprising, consisting essentially of, or consisting of the amino acid sequence LAQADTTKNA (SEQ ID NO:39) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 58)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

-continued

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAQADTTKNARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence TNRTSPD (SEQ ID NO:24) or comprising, consisting essentially of, or consisting of the amino acid sequence LATNRTSPDA (SEQ ID NO:40) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) or the corresponding the corresponding substitution in another AAV parental serotype and comprises from 2 to 5, from 5 to 10, or from 10 to 15 amino acid substitutions or is otherwise identical to the amino acid sequence of SEQ ID NO:2 or the to the corresponding parental AAV capsid protein sequence. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 59)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLATNRTSPDARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSINVDFTVDTNGVYSEPRPIGTRYLTRNL

In some embodiments, the variant AAV capsid comprises a peptide insertion comprising the amino acid sequence SNTTQKT (SEQ ID NO:25) or comprising, consisting essentially of, or consisting of the amino acid sequence LASNTTQKTA (SEQ ID NO:41) between amino acids 587 and 588 of VP1 of AAV2 or the corresponding amino acids of another AAV capsid and is otherwise identical to the amino acid sequence of SEQ ID NO:2 or the to the corresponding parental AAV capsid protein sequence. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 60)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLASNTTQKTARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In some embodiments, the variant AAV capsid comprises (i) a peptide insertion comprising the amino acid sequence ASDSTKA (SEQ ID NO:26) or comprising, consisting essentially of, or consisting of the amino acid sequence LAASDSTKAA (SEQ ID NO:42) between amino acids 587 and 588 of VP1 of AAV2 or the corresponding amino acids of another AAV capsid and (ii) a V708I amino acid substitution relative to the amino acid sequence of AAV2 capsid (SEQ ID NO:2) the corresponding substitution in another AAV parental serotype, wherein the substituted amino acid(s) do not naturally occur at the corresponding positions, and comprises from 2 to 5, from 5 to 10, or from 10 to 15 amino acid substitutions or is otherwise identical to the amino acid sequence of SEQ ID NO:2 or to the corresponding parental AAV capsid protein sequence. In another embodiment, the variant capsid comprises a peptide insertion comprising the amino acid sequence ASDSTKA (SEQ ID NO:26) or comprising, consisting essentially of, or consisting of the amino acid sequence LAASDSTKAA (SEQ ID NO:42) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 61)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

```
TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAASDSTKAARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL.
```

In several aspects, a variant AAV capsid protein is provided comprising one or more amino acid substitutions relative to a corresponding parental AAV capsid protein, wherein the variant capsid protein, when present in an AAV virion, confers increased infectivity of a muscle cell (e.g. a skeletal or cardiac muscle cell) compared to the infectivity of a muscle cell by an AAV virion comprising the corresponding parental AAV capsid protein.

In some embodiments a variant AAV capsid protein comprises an amino acid substitution at amino acid 363 compared to the amino acid sequence of AAV2 capsid (SEQ ID NO:2) or the corresponding position in another AAV parental serotype (i.e. other than AAV2). In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 363 compared to the amino acid sequence of AAV2 capsid (SEQ ID NO:2). In some preferred embodiments, a variant AAV capsid protein comprises a P363L amino acid substitution compared to the amino acid sequence of AAV2 capsid (SEQ ID NO:2), AAV3A capsid (SEQ ID NO:3) or AAV3B capsid (SEQ ID NO:4); or a P364L amino acid substitution compared to the amino acid sequence of AAV1 capsid (SEQ ID NO:1) or AAV6 capsid (SEQ ID NO: 7); or a P354L amino acid substitution compared to the amino acid sequence of AAV4 capsid (SEQ ID NO:5) or AAV5 capsid (SEQ ID NO:6); or a P365L amino acid substitution compared to the amino acid sequence of AAV7 capsid (SEQ ID NO:8) or AAV9 capsid (SEQ ID NO:10); or a P366L amino acid substitution compared to the amino acid sequence of AAV8 capsid (SEQ ID NO:9) or AAV10 capsid (SEQ ID NO: 11). In some preferred embodiments, the variant capsid protein comprises a P363L substitution compared to the amino acid sequence of SEQ ID NO:2, or the corresponding substitution compared to any of SEQ ID NOs: 1 and 3-12, and has at least about 85%, at least about 90%, at least about 95%, at least about 98%, or at least about 99%, or greater, amino acid sequence identity to the entire length of an amino acid sequence set forth in SEQ ID NO:2, or any of SEQ ID NOs: 1 and 3-12. In some preferred embodiments, the variant capsid protein comprises an amino acid sequence comprising a P363L amino acid substitution compared to the amino acid sequence set forth in SEQ ID NO:2 and is otherwise identical to the amino acid sequence set forth in SEQ ID NO:2. In related embodiments, the variant capsid protein comprises a P363L amino acid substitution compared to the amino acid sequence of SEQ ID NO:2, or the corresponding substitution in another AAV parental serotype (i.e. other than AAV2) wherein the variant capsid protein comprises from 1 to 5, from 5 to 10, or from 10 to 15 amino acid substitutions compared to the amino acid sequence of an AAV2 capsid protein set forth in SEQ ID NO:2 or compared to the amino acid sequence of a capsid protein in another AAV parental serotype. In another preferred embodiment, the variant capsid comprises a P363L amino acid substitution and further comprises E347K and/or V708I amino acid substitution(s) compared to the amino acid sequence of SEQ ID NO:2 or the corresponding substitutions in a capsid from another AAV parental serotype (i.e. other than AAV2). In another preferred embodiment, the variant capsid comprises a P363L amino acid substitution compared to the amino acid sequence of SEQ ID NO:2 or the corresponding substitution in a capsid from another AAV parent serotype and further comprises a peptide insertion, preferably located between amino acids 587 and 588 of VP1 of AAV2, amino acids 588 and 589 of AAV3A, AAV3B, AAV9, or AAV10, amino acids 589 and 590 of VP1 of AAV7, amino acids 590 to 591 of VP1 of AAV1, AAV6, or AAV8, amino acids 584 and 585 of VP1 of AAV4, or amino acids 575 and 576 of AAV5, wherein the peptide insertion preferably comprises an amino acid sequence selected from NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42), more preferably selected from GNLTKGN (SEQ ID NO:16), LAGNLTKGNA (SEQ ID NO:30), QADTTKN (SEQ ID NO:23) and LAQADTTKNA (SEQ ID NO:39), and optionally comprises from 2 to 5, from 5 to 10, or from 10 to 15 amino acid substitutions or is otherwise identical to the amino acid sequence of SEQ ID NO:2 or the to the corresponding parental AAV capsid protein sequence.

In other embodiments a variant AAV capsid protein comprises an amino acid substitution at amino acid 593 compared to the amino acid sequence of AAV2 capsid (SEQ ID NO:2) or the corresponding position in another AAV parental serotype (i.e. other than AAV2). In some preferred embodiments, the variant capsid protein comprises an amino acid substitution at amino acid 593 compared to the amino acid sequence of AAV2 capsid (SEQ ID NO:2) and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence set forth in SEQ ID NO: 2. In some embodiments, the variant capsid protein comprises a glycine to glutamate amino acid substitution at amino acid 594 compared to the amino acid sequence of AAV1, AAV3A, AAV6, or AAV9, or at amino acid 583 of AAV5, or at amino acid 596 of AAV8 or AAV10, or an arginine to glutamate amino acid substitution at amino acid 594 of AAV3B, or an aspartate to glutamate amino acid substitution at amino acid 592 of AAV4 or a glutamine to glutamate amino acid substitution at position 595 of AAV7. In other embodiments, the variant capsid protein comprises an A593E amino acid substitution compared to the amino acid sequence of AAV2 and does not comprise one or more of the following amino acid substitutions compared to the amino acid sequence of AAV2: I19V, V369A, K26R, N215D, G355S, V46A and S196P. In related embodiments, the variant capsid protein comprises A593E and V708I amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In related embodiments, the variant capsid protein comprises A593E and S109T amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In related embodiments, the variant capsid protein comprises A593E, V708I and S109T amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to SEQ ID NO:2. In other embodiments, the variant capsid comprises A593E, V708I and N551S amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In other embodiments, the the variant capsid comprises A593E, V708I and K649E amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2. In other embodiments, the the variant capsid comprises A593E, V708I, S109T and K527Q amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2 or is otherwise identical to the amino acid sequence set forth in SEQ ID NO:2.

In other embodiments a variant AAV capsid protein comprises an amino acid substitution at amino acid 708 compared to the amino acid sequence of AAV2 capsid (SEQ ID NO:2) or the corresponding position in another AAV parental serotype (i.e. other than AAV2) wherein the substituted amino acid does not naturally occur at the corresponding position. Preferably, the rAAV virion does not comprise a proline to serine substitution at amino acid 250 compared to AAV2 or a corresponding amino acid in another AAV parental serotype. In some embodiments, the variant capsid protein comprises an amino acid substitution at amino acid 708 compared to the amino acid sequence of AAV2 capsid (SEQ ID NO:2) and has at least about 85%, at least about 90%, at least about 95%, at least about 98%, or at least about 99%, or greater, amino acid sequence identity to the entire length of the amino acid sequence set forth in SEQ ID NO 2 or is otherwise identical to SEQ ID NO:2. In preferred embodiments, the variant capsid protein comprises a valine to isoleucine (V708I) substitution at amino acid 708 compared to the amino acid sequence of AAV2 capsid and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2, wherein the variant capsid protein does not comprise a P250S amino acid substitution. In some embodiments, the variant capsid protein comprises a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In related embodiments, the variant capsid protein comprises a V708I amino acid substitution compared to the amino acid sequence of AAV2, wherein the variant capsid protein comprises from 2 to 5, from 5 to 10, or from 10 to 15 amino acid substitutions and wherein the variant capsid protein does not comprise a P250S amino acid substitution. In other embodiments, the variant capsid protein comprises a V708I amino acid substitution and also comprises an A333S and/or S721L amino acid substitution compared to the amino acid sequence of AAV2. In other related embodiments, the variant capsid comprises a V708I amino acid substitution and also comprises an A333S and/or S721L amino acid substitution compared to the amino acid sequence of AAV2 and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2.

In other embodiments, a variant AAV capsid protein comprises an amino acid sequence at least 85%, at least 90%, at least 95% or at least 98% identical to a wild-type AAV capsid sequence selected from the group consisting of SEQ ID NOS: 1, 2, 3, 4, 5, 6, 7, 8, 10, 11 and 12 and also comprises i) one or more amino acid substitutions selected from the group consisting of A35P, D213N, A319T+P195L, P363L, P363L+V708I, G453R, R6511H, I698V, V708I, V708I+A593, V708I+S109T, V708I+T330A, V708I+R588M, V708I+W694C, V708I+W606C, V708I+N449K, V708I+G222S, N312K+N449D+N551S+I698V+L735Q, N312K+N449D+N551S+I698V+V708I+L735Q, and/or (ii) a peptide insertion selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42). In some embodiments, the variant AAV capsid comprises the specified one or more amino acid substitutions and/or peptide insertions and is otherwise identical to a sequence selected from the group consisting of SEQ ID NOS: 1-12.

In some embodiments, a variant AAV capsid protein is an ancestral capsid protein comprising one or more peptide insertion(s) and/or amino acid substitutions as herein described. By an ancestral capsid protein it is meant an evolutionary ancestor of a capsid protein that is found in nature today, e.g. AAV1, AAV2, AAV3, AAV4, AAV5, AAV6, AAV7, AAV8, AAV9, AAVrh10, AAV1 1, AAV12, AAV13, which is generated in silico by random amino acid substitution at positions of degeneracy between AAV capsid proteins that are found in nature today.

In other embodiments, a variant AAV capsid protein is a chimera comprising amino acids 130-725 of AAV5 capsid (SEQ ID NO:6) or an amino acid sequence at least 90%, at least 95% or at least 98% identical thereto.

In some aspects, a variant AAV capsid protein is a chimera comprising (i) amino acids 1-129 of AAV6 (SEQ ID NO:7) or an amino acid sequence at least 90%, at least 95% or at least 98% identical thereto and (ii) amino acids 130-725 of AAV5 (SEQ ID NO:6) or an amino acid sequence at least 90%, at least 95% or at least 98% identical thereto and further comprising V229I, A490T and A581T and optionally V447F or Y585S amino acid substitutions relative to the sequence of AAV5 (SEQ ID NO:6). In some embodiments, the variant AAV capsid has an amino acid sequence having at least about 85%, at least about 90%, at least about 95%, at least about 98% sequence identity to or is 100% identical to the following amino acid sequence:

```
                                              (SEQ ID NO: 62)
MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF

QERLQEDTSFGGNLGRAVFQAKKRVLEPFGLVEEGAKTAPTGKRIDDHFP

KRKKARTEEDSKPSTSSDAEAGPSGSQQLQIPAQPASSLGADTMSAGGGG

PLGDNNQGADGVGNASGDWHCDSTWMGDRIVTKSTRTWVLPSYNNHQYRE

IKSGSVDGSNANAYFGYSTPWGYFDFNRFHSHWSPRDWQRLINNYWGFRP

RSLRVKIFNIQVKEVTVQDSTTTIANNLTSTVQVFTDDDYQLPYVVGNGT

EGCLPAFPPQVFTLPQYGYATLNRDNTENPTERSSFFCLEYFPSKMLRTG

NNFEFTYNFEEVPFHSSFAPSQNLFKLANPLVDQYLYRFVSTNNTGGVQF

NKNLAGRYANTYKNWFPGPMGRTQGWNLGSGVNRASVSAFTTTNRMELEG

ASYQVPPQPNGMTNNLQGSNTYALENTMIFNSQPANPGTTATYLEGNMLI

TSESETQPVNRVAYNVGGQMATNNQSSTTAPTTGTYNLQEIVPGSVWMER

DVYLQGPIWAKIPETGAHFHPSPAMGGFGLKHPPPMMLIKNTPVPGNITS

FSDVPVSSFITQYSTGQVTVEMEWELKKENSKRWNPEIQYTNNYNDPQFV

DFAPDSTGEYRTTRPIGTRYLTRPL
```

In other aspects, a variant AAV capsid protein is a chimera comprising (i) amino acids 1-61 of AAV2 (SEQ ID NO:2) or an amino acid sequence at least 90%, at least 95% or at least 98% identical thereto, (ii) amino acids 62-129 of AAV6 (SEQ ID NO:7) or an amino acid sequence at least 90%, at least 95% or at least 98% identical thereto, and (iii) amino acids 130-725 of AAV5 (SEQ ID NO:6) and further comprising V229I, A490T and A581T amino acid substitutions relative to the sequence of AAV5 (SEQ ID NO:6). In some embodiments, the variant AAV capsid has an amino acid sequence having at least about 85%, at least about 90%, at least about 95%, at least about 98% sequence identity to or is 100% identical to the following amino acid sequence:

```
                                              (SEQ ID NO: 63)
MAADGYLPDWLEDTLSEGIRQWWKLKPGPPPPKPAERHKDDSRGLVLPGY

KYLGPFNGLDKGEPVNAADAAALEHDKAYDQQLKAGDNPYLRYNHADAEF

QERLQEDTSFGGNLGRAVFQAKKRVLEPFGLVEEGAKTAPTGKRIDDHFP

KRKKARTEEDSKPSTSSDAEAGPSGSQQLQIPAQPASSLGADTMSAGGGG

PLGDNNQGADGVGNASGDWHCDSTWMGDRIVTKSTRTWVLPSYNNHQYRE

IKSGSVDGSNANAYFGYSTPWGYFDFNRFHSHWSPRDWQRLINNYWGFRP

RSLRVKIFNIQVKEVTVQDSTTTIANNLTSTVQVFTDDDYQLPYVVGNGT

EGCLPAFPPQVFTLPQYGYATLNRDNTENPTERSSFFCLEYFPSKMLRTG

NNFEFTYNFEEVPFHSSFAPSQNLFKLANPLVDQYLYRFVSTNNTGGVQF

NKNLAGRYANTYKNWFPGPMGRTQGWNLGSGVNRASVSAFTTTNRMELEG

ASYQVPPQPNGMTNNLQGSNTYALENTMIFNSQPANPGTTATYLEGNMLI

TSESETQPVNRVAYNVGGQMATNNQSSTTAPTTGTYNLQEIVPGSVWMER

DVYLQGPIWAKIPETGAHFHPSPAMGGFGLKHPPPMMLIKNTPVPGNITS

FSDVPVSSFITQYSTGQVTVEMEWELKKENSKRWNPEIQYTNNYNDPQFV

DFAPDSTGEYRTTRPIGTRYLTRPL
```

The AAV variants disclosed herein were generated through the use of in vivo directed evolution involving the use of primate cardiac and skeletal muscle screens following intravenous administration. In some embodiments, the variant capsid proteins disclosed herein, when present in an AAV virion, confer increased transduction of a muscle cell compared to the transduction of the muscle cell by an AAV virion comprising the corresponding parental AAV capsid protein or wild-type AAV. For example, in some embodiments, the variant capsid proteins disclosed herein, when present in an AAV virion, confer more efficient transduction of primate muscle cells than AAV virions comprising the corresponding parental AAV capsid protein or wild-type AAV capsid protein, e.g. the muscle cells take up more AAV virions comprising the subject variant AAV capsid protein than AAV virions comprising the parental AAV capsid protein or wild-type AAV. In some such embodiments, the AAV variant virion or variant rAAV exhibits at least 2-fold, at least 5-fold, at least 10-fold, at least 15-fold, at least 20-fold, at least 25-fold, at least 50-fold, or more than 50-fold, increased transduction of a muscle cell, compared to the transduction of the muscle cell by a wild-type AAV virion or rAAV comprising the corresponding parental AAV capsid protein. In preferred embodiments, the the AAV variant virion or variant rAAV exhibits at least 2-fold, at least 5-fold, at least 10-fold, at least 15-fold, at least 20-fold, at least 25-fold, at least 50-fold, at least 100-fold, at least 1000-fold or more than 1000-fold, increased transduction of a muscle cell, compared to the transduction of the muscle cell by a wild-type AAV8 or AAV9 virion. In certain such embodiments, the variant capsid proteins disclosed herein, when present in an AAV virion, confer broader transduction of the primate muscle cells than AAV virions comprising the corresponding parental AAV capsid protein or wild type AAV capsid protein. In other words, the variant AAV virion transduces cell types not transduced by virions comprising the corresponding parental AAV capsid protein, and hence more types of cells in the muscle than the corresponding parental AAV virion. In some embodiments, the AAV variant virion preferentially transduces a muscle cell, e.g., a subject rAAV virion infects a muscle cell with 2-fold, 5-fold, 10-fold, 15-fold, 20-fold, 25-fold, 50-fold, or more than 50-fold, specificity than another muscle cell or a non-muscle cell. In some embodiments, the transduced muscle cell is a cardiac muscle cell (e.g. cardiomyoyte, cardiac fibroblast, or a cardiac progenitor cell). In some embodiments, the muscle cell is a skeletal muscle cell (e.g. a myoblast, a myotube or a satellite cell). An increase in transduction of a muscle cell, e.g. increased efficiency of transduction, broader transduction, more preferential transduction, etc. may be readily assessed in vitro or in vivo by any number of methods in the art for measuring gene expression. For example, the AAV may be packaged with a genome comprising an expression cassette comprising a reporter gene, e.g. a fluorescent protein, under the control of a ubiquitous or tissue specific promoter, and the extent of transduction assessed by detecting the fluorescent protein by, e.g., fluorescence microscopy. As another example, the AAV may be packaged with a genome comprising a barcoded nucleic acid sequence, and the extent of transduction assessed by detecting the nucleic acid sequence by, e.g., PCR. As another example, the AAV may be packaged with a genome comprising an expression cassette comprising a therapeutic gene for the treatment of a muscle disease, and the extent of transduction assessed by detecting the treatment of the muscle disease in an afflicted patient that was administered the AAV.

Diseases that can be treated using a variant rAAV vector or virion and/or method disclosed herein include, but are not limited to, monogenic diseases, complex diseases, and traumatic injuries. Examples of monogenic diseases include, but are not limited to, muscular dystrophies such as Duchenne, Becker, congenital (including, but not limited to Bethlem myopathy, Ullrich muscular dystrophy, Fukuyama muscular dystrophy, Integrin-Deficient, merosin-deficient muscular dystrophy, and Walker-Warburgh syndrome), distal (including, but not limited to Gowers-Laing, Miyoshi, and Nonaka), Emery-Dreifuss, facioscapulohumeral, limb girdle, myotonic and muscular dystrophies; myotonia congenita and paramyotonia congenita; myotubular myopathy; centronuclear myopathy; myofibrillary myopathy, desmin related; anemia; Andersen-Tawil syndrome; Nemaline myopathy; Brody disease; lysosomal storage disorders such as alpha-mannosidosis, aspartylglucosaminuria, beta-mannosidosis, cystinosis, Farber disease, fucosidosis, Gaucher disease, galactosialidosis, gangliosidoses (including, but not limited to AB variant, activator deficiency, beta-galactosidase deficiency, Fabry disease, Sandhoff disease, and Schindler disease), glycogen storage disorders (including, but not limited to as Andersen disease, Cori disease, Danon disease, Forbes disease, glucose-6-phosphate defect, Hers disease, lactate dehydrogenase A deficiency, Pompe disease, Tarui disease, and von Gierke disease), infantile free sialic acid storage disease, lysosomal acid lipase deficiency, Krabbe disease, Metachromatic Leukodystrophy, mucopolysaccharidoses (including, but not limited to hyaluronidase deficiency, Hunter syndrome, Hurler syndrome, Hurler-Scheie syndrome, Maroteaux-Lamy syndrome, Morquio syndrome, Sanfilippo syndrome, Schele syndrome, and Sly syndrome), mucolipidosis (including, but not limited to Sialidosis, I-cell disease, mucolipidin 1 deficiency, and Psuedy-Hurler Polydystrophy), multiple sulfase deficiency, Niemann-Pick disease, neuronal ceroid lipofuscinoses (including, but not limited to Batten-Spielmeyer-Vogt disease, congenital Cathepsin D deficiency, German/Serbian Late Infantile, Jansky-Bielschowsky disease, Kufs disease, late infantile, late infantile variant, Northern Epilepsy, Santavuori-Haltia disease, and Turkish Late Infantile), pyknodysostosis, Salla disease, Saposin B deficiency, Tay-Sach's disease and Wolman disease; metabolic disorders such as adenosine monophosphate deaminase deficiency, alkaptonuria, carnitine deficiency, carnitine palmityl transferase deficiency, Hartnup disorder, homocystinuria, maple syrup urine disease, myophosphorylase deficiency, phosphofuctokinase deficiency, phosphoglycerate kinase deficiency, phosphoglycerate mutase deficiency, phosphorylase deficiency, and Tangier disease; Friedreich's ataxia; ataxia talengiectasia; ataxia with vitamin E deficiency; periodic paralysis, such as Gamstorp disease and hypokalemic periodic paralysis; mitochondrial diseases such as Barth syndrome, Kearns-Sayre syndrome, mitochondrial myopathy, mitochondrial encephalopathy lactic acidosis and stroke-like episodes, myoclonic epilepsy with ragged-red fibers, and Pearson syndrome; familial hypertrophic cardiomyopathies; dilated cardiomyopathies; familial congenital heart diseases, such as familial aortic valve disease and non-compaction of the left ventricle with congenital heart defects; familial arrhythmias, such as Anderson cardiodysrhythmic periodic paralysis, atrial septal defects with AV conduction defects, Brugada syndrome, cardiac conductance defect, catecholaminergic polymorphic ventricular tachycardia, and congenital heart block; familial vascular disorders, such as arterial tortuosity syndrome, cerebral autosomal dominant arteriopathy with sobcortical infacts and leukoenceophalopathy, cerebral recessive dominant arteriopathy with sobcortical infacts and leukoenceophalopathy, familial type aortic aneurysm, Marfan syndrome, Ehlers-Danlos syndrome, Beals congenital contractual arachnodactyly, Loeys-Dietz syndrome, and pseudoxanthoma elasticum; arrhythmogenic right ventricular cardiomyopathy; familial arrhythmogenic right ventricular dysplasia; Naxos disease; left ventricular non-compaction; familial atrial fibrillation; familial ventricular tachycardia; familial Wolff-Parkinson-White syndrome; long QT syndromes; short QT syndrome; sick sinus syndromes; lipoprotein diseases, such as abetalipoproteinemia and lipoprotein lipase deficiency; alpha-1 antitrypsin deficiency; coagulation factor VIII deficiency (hemophilia A) or coagulation factor IX deficiency (hemophilia B); thalassemia; fibrodysplasia ossificans progressive; laminopathies; Huntington disease; congenital myasthenic syndromes; Hutchinson-Gilford Progeria syndrome; Noonan syndrome; congenital fibre type disproportion myopathy; congenital fibrosis of the extraocular muscles; minicore myopathy; rippling muscle disease; Schwartz-Jampel syndrome; tubular aggregate myopathy; and zebra body myopathy Examples of complex diseases include, but are not limited to, heart/cardiovascular disease (e.g. congestive heart failure, myocardial infarction, angina, coronary artery disease, ischaemic heart disease, cardiomyopathy); cancer; diabetes; and infection. Examples of traumatic injuries include, but are not limited to, viral infection of the muscle, muscle laceration; and muscle contusion. In preferred embodiments, a variant rAAV vector or virion and/or method disclosed herein is used to treat Fabry disease, Friedreich's ataxia, Duchenne muscular dystrophy, Becker muscular dystrophy, Pompe disease, myophosphorylase deficiency, facioscapulohumeral muscular dystrophy, limb girdle muscular dystrophy, or myotonic dystrophy.

In another embodiment, a variant capsid disclosed herein comprises a heterologous nucleic acid comprising a nucleotide sequence encoding a gene product such as, without limitation, an interfering RNA, a long non-coding RNA, a short non-coding RNA, an antisense RNA, an aptamer, a polypeptide, a secreted antibody, a single chain antibody, a VHH domain, a soluble receptor, an affibody, a knottin, a DARPin, a centurin, a chaperone, a site-specific nuclease that provides for site-specific knock-down of gene function or a modified site-specific nuclease that provides for gene-specific activation of transcription.

A rAAV variant virion disclosed herein comprises a heterologous nucleic acid comprising a nucleotide sequence encoding a gene product. In some embodiments, the gene product is an antisense RNA, a microRNA (miRNA), a short hairpin RNA (shRNA) or a small interfering RNA (siRNA) or a precursor or mimic thereof. In some embodiments, the gene product is a long non-coding RNA. In some embodiments, the gene product is a short non-coding RNA. In some embodiments, the gene product is an antisense RNA. In some embodiments, the gene product is an aptamer. In some embodiments, the gene product is a polypeptide. In some embodiments, the gene product is a secreted antibody. In some embodiments, the gene product is a single chain antibody. In some embodiments, the gene product is a VHH domain. In some embodiments, the gene product is a soluble receptor. In some embodiments, the gene product is an affibody. In some embodiments, the gene product is a knottin. In some embodiments, the gene product is a DARPin. In some embodiments, the gene product is a centurin. In some embodiments, the gene product is a chaperone. In some embodiments, the gene product is a site-specific nuclease that provide for site-specific knock-down of gene function.

The uses of the gene product include, but are not limited to, enhancing the level ofa factor in a cell, enhancing the level of a factor in a neighboring or distant cell through secretion of a factor, decreasing the level of a factor in a cell, or decreasing the level of a factor in a neighboring or distant cell through secretion of a factor. The gene product can be designed to supplement the level of a defective of missing gene product, decrease the level of a defective of missing gene product, introduce a new supporting gene product, supplement the level of a supporting gene product, decrease the level of a hindering gene product, or both decrease the level of a hindering gene product and introduce or supplement the level of a supporting gene product.

Gene products delivered by the subject AAV variants can be used to alter the level of gene products or gene product activity directly or indirectly linked to muscle diseases and trauma. Skeletal, cardiac or smooth muscle transduced with subject AAV variants can also be used as a biofactory to produce and secrete therapeutic proteins for the treatment of diseases in trans in distant organs. Genes whose gene products are directly or indirectly linked to genetic diseases include, e.g., genes encoding any of the following gene products: dystrophin including mini- and micro-dystrophins (DMD; e.g. GenBank Accession Number NP_003997.1; SEQ ID NO:64); titin (TTN); titin cap (TCAP) α-sarcoglycan (SGCA), β-sarcoglycan (SGCB), γ-sarcoglycan (SGCG) or 3-sarcoglycan (SGCD); alpha-1-antitrypsin (A1-AT); myosin heavy chain 6 (MYH6); myosin heavy chain 7 (MYH7); myosin heavy chain 11 (MYHLI 1); myosin light chain 2 (ML2); myosin light chain 3 (ML3); myosin light chain kinase 2 (MYLK2); myosin binding protein C (MYBPC3); desmin (DES); dynamin 2 (DNM2); laminin a2 (LAMA2); lamin A/C (LMNA); lamin B (LMNB); lamin B receptor (LBR); dysferlin (DYSF); emerin (EMD); insulin; blood clotting factors, including but not limited to, factor VIII and factor IX; erythropoietin (EPO); lipoprotein lipase (LPL); sarcoplasmic reticulum $Ca^{2++}$-ATPase (SERCA2A), S100 calcium binding protein A1 (S100A1); myotubularin (MTM); DM1 protein kinase (DMPK; e.g. GenBank Accession Number NG_009784.1; SEQ ID NO:65); glycogen phosphorylase L (PYGL); glycogen phosphorylase, muscle associated (PYGM; e.g. GenBank Accession Number NP_005600.1; SEQ ID NO:66); glycogen synthase 1 (GYS1); glycogen synthase 2 (GYS2); α-galactosidase A (GLA; e.g. GenBank Accession Number NP_000160.1; SEQ ID NO:67); α-N-acetylgalactosaminidase (NAGA); acid α-glucosidase (GAA; e.g. GenBank Accession Number NP_000143.2; SEQ ID NO:68), sphingomyelinase phosphodiesterase 1 (SMPD1); lysosomal acid lipase (LIPA); collagen type I α1 chain (COL1A1); collagen type I α2 chain (COL1A2); collagen type III α1 chain. (COL3A1); collagen type V α1 chain (COL5A1); collagen type V α2 chain (COL5A2); collagen type VI α1 chain (COL6A1); collagen type VI α2 chain (COL6A2); collagen type VI α3 chain (COL6A3); procollagen-lysine 2-oxoglutarate 5-dioxygenase (PLOD); lysosomal acid lipase (LIPA); frataxin (FXN; e.g. GenBank Accession Number NP_000135.2; SEQ ID NO:69); myostatin (MSTN); β-N-acetyl hexosaminidase A (HEXA); β-N-acetylhexosaminidase B (HEXB); β-glucocerebrosidase (GBA); adenosine monophosphate deaminase 1 (AMPD1); β-globin (HBB); iduronidase (IDUA); iduronate 2-sulfate (IDS); troponin 1 (TNNI3); troponin T2 (TNNT2); troponin C (TNNC1); tropomyosin 1 (TPM1); tropomyosin 3 (TPM3); N-acetyl-α-glucosaminidase (NAGLU); N-sulfoglucosamine sulfohydrolase (SGSH); heparan-α-glucosaminide N-acetyltransferase (HGSNAT); integrin a 7 (IGTA7); integrin a 9 (IGTA9); glucosamine (N-acetyl)-6-sulfatase (GNS); galactosamine (N-acetyl)-6-sulfatase (GALNS); β-galactosidase (GLB1); β-glucuronidase (GUSB); hyaluronoglucosaminidase 1 (HYALI); acid ceramidase (ASAHI); galactosylcermidase (GALC); cathepsin A (CTSA); cathepsin D (CTSA); cathepsin K (CTSK); GM2 ganglioside activator (GM2A); arylsulfatase A (ARSA); arylsulfatase B (ARSB); formylglycine-generating enzyme (SUMF1); neuraminidase 1 (NEU1); N-acetylglucosamine-1-phosphate transferase α (GNPTA); N-acetylglucosamine-1-phosphate transferase β (GNPTB); N-acetylglucosamine-1-phosphate transferase γ (GNPTG); mucolipin-1 (MCOLN1); NPC intracellular transporter 1 (NPC1); NPC intracellular transporter 2 (NPC2); ceroid lipofuscinosis 5 (CLN5); ceroid lipofuscinosis 6 (CLN6); ceroid lipofuscinosis 8 (CLNS); palmitoyl protein thioesterase 1 (PPT1); tripeptidyl peptidase 1 (TPP1); battenin (CLN3); DNAJ heat shock protein family 40 member C5 (DNAJC5); major facilitator superfamily domain containing 8 (MFSD8); mannosidase α class 2B member 1 (MAN2B1); mannosidase β (MANBA); aspartylglucosaminidase (AGA); α-L-fucosidase (FUCA1); cystinosin, lysosomal cysteine transporter (CTNS); sialin; solute carrier family 2 member 10 (SLC2A10); solute carrier family 17 member 5 (SLC17A5); solute carrier family 6 member 19 (SLC6A19); solute carrier family 22 member 5 (SLC22A5); solute carrier family 37 member 4 (SLC37A4); lysosomal associated membrane protein 2 (LAMP2); sodium voltage-gated channel a subunit 4 (SCN4A); sodium voltage-gated channel p subunit 4 (SCN4B); sodium voltage-gated channel a subunit 5 (SCN5A); sodium voltage-gated channel a subunit 4 (SCN4A); calcium voltage-gated channel subunit alc (CACNAIC); calcium voltage-gated channel subunit αls (CACNAIS); phosphoglycerate kinase 1 (PGK1); phosphoglycerate mutase 2 (PGAM2); amylo-α-1,6-glucosidase, 4-α-glucanotransferase (AGL); potassium voltage-gated channel 1SK-related subfamily member 1 (KCNE1); potassium voltage-gated channel ISK-related subfamily member 2 (KCNE2); potassium voltage-gated channel subfamily J member 2 (KCNJ2); potassium voltage-gated channel subfamily J member 5 (KCNJ5); potassium voltage-gated channel subfamily H member 2 (KCNH2); potassium voltage-gated channel KQT-like subfamily member 1 (KCNQI); hyperpolarization-activated cyclic nucleotide-gated potassium channel 4 (HCN4); chloride voltage-gated channel 1 (CLCN1); carnitine palmitoyltransferase 1A (CPT1A); ryanodine receptor 1 (RYR1); ryanodine receptor 2 (RYR2); bridging integrator 1 (BINI); LARGE xylosyl- and glucuronyltransferase 1 (LARGE1); docking protein 7 (DOK7); fukutin (FKTN); fukutin related protein (FKRP); selenoprotein N (SELENON); protein O-mannosyltransferase 1 (POMT1); protein O-mannosyltransferase 2 (POMT2); protein O-linked mannose N-acetylglucosaminyltransferase 1 (POMGNT1); protein O-linked mannose N-acetylglucosaminyltransferase 2 (POMGNT2); protein-O-mannose kinase (POMK); isoprenoid synthase domain containing (ISPD); plectin (PLEC); cholinergic receptor nicotinic epsilon subunit (CHRNE); choline O-acetyltransferase (CHAT); choline kinase p (CHKB); collagen like tail subunit of asymmetric acetylcholinesterase (COLQ); receptor associated protein of the synapse (RAPSN); four and a half LIM domains 1 (FHL1); β-1,4-glucuronyltransferase 1 (B4GAT1); R-1,3-N-acetylgalactosaminyltransferase 2 (B3GALNT2); dystroglycan 1 (DAG1); transmembrane protein 5 (TMEM5); transmembrane protein 43 (TMEM43); SECIS binding protein 2 (SECISBP2); glucosamine (UDP-N-acetyl)-2-epimerase/N-acetylmannosamine kinase (GNE); anoctamin 5 (ANOS); structural maintenance of chromosomes flexible hinge domain containing 1 (SMCHD1); lactate dehydrogenase A (LDHA); lactate dehydrogenase B (LHDB); calpain 3 (CAPN3); caveolin 3 (CAV3); tripartite motif containing 32 (TRIM32); CCHC-type zinc finger nucleic acid binding protein (CNBP); nebulin (NEB); actin, a1, skeletal muscle (ACTA1); actin, α1, cardiac muscle (ACTC1); actinin α2 (ACTN2); poly(A)-binding protein nuclear 1 (PABPNI); LEM domain-containing protein 3 (LEMD3); zinc metalloproteinase STE24 (ZMPSTE24); microsomal triglyceride transfer protein (MTTP); cholinergic receptor nicotinic α1 subunit (CHRNA1); cholinergic receptor nicotinic α2 subunit (CHRNA2); cholinergic receptor nicotinic β3 subunit (CHRNA3); cholinergic receptor nicotinic α4 subunit (CHRNA4); cholinergic receptor nicotinic α5 subunit (CHRNA5); cholinergic receptor nicotinic α6 subunit (CHRNA6); cholinergic receptor nicotinic α7 subunit (CHRNA7); cholinergic receptor nicotinic α8 subunit (CHRNA8); cholinergic receptor nicotinic α9 subunit (CHRNA9); cholinergic receptor nicotinic α10 subunit (CHRNA10); cholinergic receptor nicotinic β1 subunit (CHRNB1); cholinergic receptor nicotinic β2 subunit (CHRNB2); cholinergic receptor nicotinic β3 subunit (CHRNB3); cholinergic receptor nicotinic β4 subunit (CHRNB4); cholinergic receptor nicotinic γ subunit (CHRNG1); cholinergic receptor nicotinic δ subunit (CHRND); cholinergic receptor nicotinic ε subunit (CHRNE1); ATP binding cassette subfamily A member 1 (ABCA1); ATP binding cassette subfamily C member 6 (ABCC6); ATP binding cassette subfamily C member 9 (ABCC9); ATP binding cassette subfamily D member 1 (ABCD1); ATPase sarcoplasmic/endoplasmic reticulum Ca2+ transporting 1 (ATP2A1); ATM serine/threonine kinase (ATM); a tocopherol transferase protein (TTPA); kinesin family member 21A (KIF21A); paired-like homeobox 2a (PHOX2A); heparan sulfate proteoglycan 2 (HSPG2); stromal interaction molecule 1 (STIM1); notch 1 (NOTCH1); notch 3 (NOTCH3); dystrobrevin a (DTNA); protein kinase AMP-activated, noncatalytic γ2 (PRKAG2); cysteine- and glycine-rich protein 3 (CSRP3); viniculin (VCL); myozenin 2 (MyoZ2); myopalladin (MYPN); junctophilin 2 (JPH2); phospholamban (PLN); calreticulin 3 (CALR3); nexilin F-actin-binding protein (NEXN); LIM domain binding 3 (LDB3); eyes absent 4 (EYA4); huntingtin (HTT); androgen receptor (AR); protein tyrosine phosphate non-receptor type 11 (PTPN11); junction plakoglobin (JUP); desmoplakin (DSP); plakophilin 2 (PKP2); desmoglein 2 (DSG2); desmocollin 2 (DSC2); catenin α3 (CTNNA3); NK2 homeobox 5 (NKX2-5); A-kinase anchor protein 9 (AKAP9); A-kinase anchor protein 10 (AKAP10); guanine nucleotide-binding protein α-inhibiting activity polypeptide 2 (GNAI2); ankyrin 2 (ANK2); syntrophin α-1 (SNTA1); calmodulin 1 (CALM1); calmodulin 2 (CALM2); HTRA serine peptidase 1 (HTRA1); fibrillin 1 (FBN1); fibrillin 2 (FBN2); xylosyltransferase 1 (XYLT1); xylosyltransferase 2 (XYLT2); tafazzin (TAZ); homogentisate 1,2-dioxygenase (HGD); glucose-6-phosphatase catalytic subunit (G6PC); 1,4-alpha-glucan enzyme 1 (GBE1); phosphofructokinase, muscle (PFKM); phosphorylase kinase regulatory subunit alpha 1 (PHKA1); phosphorylase kinase regulatory subunit alpha 2 (PHKA2); phosphorylase kinase regulatory subunit beta (PHKB); phosphorylase kinase catalytic subunit gamma 2 (PHKG2); phosphoglycerate mutase 2 (PGAM2); cystathionine-beta-synthase (CBS); methylenetetrahydrofolate reductase (MTHFR); 5-methyltetrahydrofolate-homocysteine methyltransferase (MTR); 5-methyltetrahydrofolate-homocysteine methyltransferase reductase (MTRR); methylmalonic aciduria and homocystinuria, cbID type (MMADHC); mitochondrial DNA, including, but not limited to mitochondrially encoded NADH:ubiquinone oxidoreductase core subunit 1 (MT-ND1); mitochondrially encoded NADH:ubiquinone oxidoreductase core subunit 5 (MT-ND5); mitochondrially encoded tRNA glutamic acid (MT-TE); mitochondrially encoded tRNA histadine (MT-TH); mitochondrially encoded tRNA leucine 1 (MT-TL1); mitochondrially encoded tRNA lysine (MT-TK); mitochondrially encoded tRNA serine 1 (MT-TS1); mitochondrially encoded tRNA valine (MT-TV); mitogen-activated protein kinase kinase 1 (MAP2K1); B-Raf proto-oncogene, serine/threonine kinase (BRAF); raf-1 proto-oncogene, serine/threonine kinase (RAF); growth factors, including, but not limited to insulin growth factor 1 (IGF-1); transforming growth factor β3 (TGFβ); transforming growth factor β receptor, type 1 (TGFβR1); transforming growth factor β receptor, type II (TGFβR2), fibroblast growth factor 2 (FGF2), fibroblast growth factor 4 (FGF4), vascular endothelial growth factor A (VEGF-A), vascular endothelial growth factor B (VEGF-B); vascular endothelial growth factor C (VEGF-C), vascular endothelial growth factor D (VEGF-D), vascular endothelial growth factor receptor 1 (VEGFR1), and vascular endothelial growth factor receptor 2 (VEGFR2); interleukins; immunoadhesins; cytokines; and antibodies.

In preferred embodiments, gene products delivered by the subject AAV variants are selected from alpha galactosidase A (GLA), Frataxin (FXN), Dystrophin (DMD), Acid alpha glucosidase (GAA), and Glycogen phosphorylase, muscle (PYGM). In some preferred embodiments, a subject AAV variant comprises a nucleic acid segment comprising a nucleotide sequence encoding (i) a GLA polypeptide comprising or consisting of the amino acid sequence set forth as SEQ ID NO:67, (ii) an FXN polypeptide comprising or consisting of the amino acid sequence set forth as SEQ ID NO:69, (iii) a DMD polypeptide comprising or consisting of a functional fragment (e.g. mini or micro dystrophin, preferably comprising an intact actin-binding domain, at least 4 of the 24 spectrin-like repeats and the dystroglycan-binding domain) of the amino acid sequence set forth as SEQ ID NO:64, (iv) a GAA polypeptide comprising or consisting of the amino acid sequence set forth as SEQ ID NO:68, (v) a PYGM polypeptide comprising or consisting of the amino acid sequence set forth as SEQ ID NO:66, (vi) or (v) an amino acid sequence at least 80%, at least 85%, at least 90% or at least 95% identical to any one of SEQ ID NOs:64 and 66-69.

In another preferred embodiment, a subject AAV variant comprises a transgene encoding an interfering RNA, e.g. an antisense RNA, an miRNA, an shRNA, or an siRNA, that decreases the expression of DMPK. In some aspects, the interfering RNA decreases the expression of DMPK encoded by a nucleic acid having a nucleotide sequence as set forth as SEQ ID NO:65 or a sequence at least 80%, at least 85%, at least 90%, or at least 95% identical to SEQ ID NO:65.

Genes whose gene products induce or promote apoptosis are referred to herein as "pro-apoptotic genes" and the products of those genes (mRNA; protein) are referred to as "pro-apoptotic gene products." Pro-apoptotic targets include, e.g., Bax gene products; Bid gene products; Bak gene products; Bad gene products; Bcl-2; Bcl-Xl. Anti-apoptotic gene products include X-linked inhibitor of apoptosis.

Genes whose gene products induce or promote angiogenesis are referred to herein as "pro-angiogenic genes" and the products of those genes (mRNA; protein) are referred to as "pro-angiogenic gene products." Pro-angiogenic targets include, e.g., vascular endothelial growth factor (VEGFa, VEGFb, VEGFc, VEGFd); vascular endothelial growth factor receptor 1 (VEGFR1); vascular endothelial growth factor receptor 2 (VEGFR2); Fms-Related Tyrosine Kinase 1 (Flt1); placenta growth factor (PGF); Platelet-derived growth factor (PDGF); angiopoietins; sonic hedgehog. Genes whose gene products inhibit angiogenesis are referred to herein as "anti-angiogenic genes" and the products of those genes (mRNA; protein) are referred to as "anti-angiogenic gene products." Anti-angiogenic gene products include endostatin; tumstatin; angiostatin; pigment epithelium-derived factor (PEDF), and fusion proteins or antibodies that are specific for pro-angiogenic targets and/or their receptors, e.g. the VEGF-specific antibody Avastin™, etc.

Genes whose gene products function as immune modulators, e.g., complement factors, toll-like receptors, are called "immunomodulatory genes". Exemplary immunomodulatory genes include cytokines, chemokines, and the fusion proteins or antibodies that are specific for them and/or their receptors, e.g. the anti-IL-6 fusion protein Rilonacept®, the Complement Factor H-specific antibody lampamizumab, etc. Genes whose gene products function as muscle protective factors, e.g., insulin growth factor 1 (IGF-1); transforming growth factor β (TGFβ); fibroblast growth factor (FGF).

In some cases, a gene product of interest is a site-specific endonuclease that provide for site-specific knock-down of gene function, e.g., where the endonuclease knocks out an allele associated with a muscle disease. For example, where a dominant allele encodes a defective copy of a gene that, when wild-type, is a muscle structural protein and/or provides for normal muscle function, a site-specific endonuclease can be targeted to the defective allele and knock out the defective allele.

In addition to knocking out a defective allele, a site-specific nuclease can also be used to stimulate homologous recombination with a donor DNA that encodes a functional copy of the protein encoded by the defective allele. Thus, e.g., a subject rAAV virion can be used to deliver both a site-specific endonuclease that knocks out a defective allele, and can be used to deliver a functional copy of the defective allele, resulting in repair of the defective allele, thereby providing for production of a functional muscle protein (e.g., functional lamin A/C, functional fibrillin, functional collagen type VI, etc.). In some embodiments, a rAAV virion disclosed herein comprises a heterologous nucleotide sequence that encodes a site-specific endonuclease; and a heterologous nucleotide sequence that encodes a functional copy of a defective allele, where the functional copy encodes a functional muscle protein. Functional muscle proteins include, e.g., lamin A/C, fibrillin 1, COL6A1, COL6A2, COL6A3, and the like.

Site-specific endonucleases that are suitable for use include, e.g., meganucleases; zinc finger nucleases (ZFNs); transcription activator-like effector nucleases (TALENs); and Clustered regularly interspaced short palindromic repeats/CRISPR-associated (Cas), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

In some embodiments of the variant rAAV vector disclosed herein, a nucleotide sequence encoding a gene product of interest is operably linked to a constitutive promoter. Suitable constitutive promoters include e.g. cytomegalovirus promoter (CMV) (Stinski et al. (1985) *Journal of Virology* 55(2): 431-441), CMV early enhancer/chicken β-actin (CBA) promoter/rabbit β-globin intron (CAG) (Miyazaki et al. (1989) *Gene* 79(2): 269-277, CBSB (Jacobson et al. (2006) *Molecular Therapy* 13(6): 1074-1084), human elongation factor 1α promoter (EF1α) (Kim et al. (1990) *Gene* 91(2): 217-223), human phosphoglycerate kinase promoter (PGK) (Singer-Sam et al. (1984) *Gene* 32(3): 409-417, mitochondrial heavy-strand promoter (Loderio et al. (2012) *PNAS* 109(17): 6513-6518), ubiquitin promoter (Wulff et al. (1990) *FEBS Letters* 261: 101-105). In other embodiments, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a muscle-specific regulatory element (e.g., a cardiac specific promoter or a skeletal muscle specific promoter), e.g., a regulatory element that confers selective expression of the operably linked gene in a muscle cell. Suitable muscle-specific regulatory elements include, e.g., skeletal muscle α-actin promoter (Muscat and Kedes (1987) *Mol. Cell. Biol.* 7:4089-4099); cardiac muscle α-actin promoter (Minty and Kedes (1986) *Mol. Cell. Biol.* 6:2125-2136); smooth muscle α-actin promoter (Nakano et al. (1991) *Gene* 99:285-289); vascular smooth muscle α-actin promoter (Keogh et al. (1999) *Gene Therapy* 6(4):616-628); muscle creatine kinase promoter (Bartlett et al. (1996)

Cell Transplantation 5(3):411-419); myosin light chain 1 and myosin light chain 3 promoters (Seidel and Arnold (1989) J. Biol. Chem. 264(27):16109-16117); myosin light chain 2v (MLC2v) promoter (Su et al. (2004) PNAS 101 (46):16280-16285); myogenic factor 5 (Myf5) promoter (Fujimaki et al. (2004) Journal of Biological Chemistry 289(11):7399-7412); myogenic differentiation 1 (Myod1) promoter (Zingg et al. (1994) Nucleic Acids Research 22(12):2234-2241); myogenin (Myog) promoter (Salminen et al. (1991) Journal of Cell Biology 115(4):905-917); paired box gene 7 (Pax7) promoter (Murmann et al. (2000) Biol Chem. 381(4):331-335); paired like homeodomain 3 (Pitx3) promoter (Coulon et al. (2007) Journal of Biological Chemistry 282:33192-33200); MHCK7 promoter (Salva et al. (2007) Mol. Ther. 15(2):320-329); MCK/SV40 promoter (Takeshita et al. (2007) International Journal of Molecular Medicine 19:309-315); C5-12 promoter (Li et al. (1999) Nature Biotechnology 17:241-245); double and triple tandem MCK enhancer/promoters (Wang et al. (2008) Gene Therapy 15:1489-1499); myosin heavy chain 7 (MYH7) promoter; (Iwaki et al. (2104) PLoS ONE 9(4):e88610); myosin heavy chain 6 (MYH6) promoter (Pacak et al. (2008) Genet. Vaccines Ther. 6:13); cardiac troponin T (TNNT2) promoter (Farza et al. (1998) J. Mol. Cell Cardiol. 30(6):1247-53); α-tropomyosin promoter (Helfinan et al. (1986) Molecular and Cellular Biology 6(11):3582-3595); cardiac troponin C (TNNC1) promoter (Scheier et al. (1990) Journal of Biological Chemistry 34(5):21247-21253); cardiac myosin-binding protein C promoter (Lin et al. (2013) PLoS ONE 8(7): e69671); cardiac troponin 1 (TNNI3) promoter (Bhavsar et al. (1996) Genomics 35(1):11-23); the desmin promoter (Li et al. (1991) Journal of Biological Chemistry 10(5):6562-6570); sodium-calcium exchanger (NCX1) promoter (Scheller et al. (1997) Journal of Biological Chemistry 273(13):7643-7649); atrial natriuretic factor promoter (Durocher et al. (1996) Molecular and Cellular Biology 16(9):4648-4655); and SM22a promoter (Kemp et al. (1995) Biochemical Journal 310(3):1037-1043.

For the purposes of the invention, the disclosure herein provides an isolated nucleic acid comprising a nucleotide sequence that encodes a variant AAV capsid protein as described above. An isolated nucleic acid can be an AAV vector, e.g., a recombinant AAV vector.

The disclosure herein also provides a method of treating a muscle disease, the method comprising administering to an individual in need thereof an effective amount of a rAAV variant virion comprising a transgene of interest as described above and disclosed herein. One of ordinary skill in the art would be readily able to determine an effective amount of the subject rAAV virion and that the disease had been treated by testing for a change in one or more functional or anatomical parameters, e.g. muscle biopsy followed by immunohistochemistry, serum sampling followed by ELISA or enzyme activity assays, walk test, peak maximum oxygen consumption, biomarker analysis left ventricular ejection fraction, left ventricular end-systolic volume, hand-held dynamometry, maximum weight lift, Timed Function Tests, the Hammersmith Motor Ability Score, timed rise from floor, or 9 Hole Peg Test.

Nonlimiting methods for assessing muscle function and changes thereof include assessing walk test, peak maximum oxygen consumption, biomarker analysis, left ventricular ejection fraction, left ventricular end-systolic volume, Vignos Scale, Timed Function Tests, the Hammersmith Motor Ability Score, timed rise from floor, Motor Function Measure Scale, North Star Ambulatory Assessment, 9 Hole Peg Test, or Children's Hospital of Philadelphia Infant Test of Neuromuscular Disorders.

In some embodiments, an effective amount of the subject rAAV virion results in a decrease in the rate of loss of muscle function, anatomical muscle integrity, or muscle mass, e.g. a 2-fold, 3-fold, 4-fold, or 5-fold or more decrease in the rate of loss and hence progression of disease, for example, a 10-fold decrease or more in the rate of loss and hence progression of disease. In some embodiments, the effective amount of the subject rAAV virion results in a gain in muscle function, gain in muscle strength, gain in muscle mass, and/or an improvement in anatomical muscle integrity or biomarkers, e.g. a 2-fold, 3-fold, 4-fold or 5-fold improvement or more in muscle function, muscle strength, muscle mass, and/or improvement in anatomical muscle integrity or biomarkers, e.g. a 10-fold improvement or more in muscle function, muscle strength, muscle mass and/or improvement in anatomical muscle integrity or biomarkers. As will be readily appreciated by the ordinarily skilled artisan, the dose required to achieve the desired treatment effect will typically be in the range of $1\times10^8$ to about $1\times10^{16}$ recombinant virions, typically referred to by the ordinarily skilled artisan as $1\times10^8$ to about $1\times10^{16}$ "vector genomes" and preferably will be in the range of about $1\times10^{11}$ to about $1\times10^{15}$ recombinant virions.

A subject rAAV virion can be delivered to skeletal muscle by intravascular (intravenous or intra-arterial) administration, intraperitoenal administration, limb perfusion and/or direct intramuscular injection or by any other convenient mode or route of administration that will result in the delivery of the rAAV virion to skeletal muscle. The rAAV virion can be delivered to cardiac muscle by intravascular (intravenous or intra-arterial) administration, direct cardiac injection (into the left atrium, right atrium, right ventricle and/or septum), antegrade or retrograde infusion into the coronary artery (via the left anterior descending or left circumflex coronary arteries), recirculation, intrapericardial injection, transendocardial injection, or by any other convenient mode or route of administration that will result in the delivery of the rAAV virion to cardiac muscle. In a preferred embodiment, a subject rAAV virion is delivered to skeletal and/or cardiac muscle by systemic intravenous administration. When administered via intravenous injection, the subject rAAV virion is able to move through the circulatory system and transduce muscle cells more efficiently, compared to the capability of a wild type AAV virion or an AAV virion comprising the corresponding parental AAV capsid protein.

A variant capsid protein disclosed herein is isolated, e.g., purified. In some embodiments, a variant capsid protein disclosed herein is included in an AAV vector or a recombinant AAV (rAAV) virion. In other embodiments, such AAV variant vectors and/or AAV variant virions are used in an in vivo or ex vivo method of treating a muscle disease in primate cardiac or skeletal muscle.

The disclosure herein further provides host cells such as, without limitation, isolated (genetically modified) host cells comprising a subject nucleic acid. A host cell according to the invention disclosed herein, can be an isolated cell, such as a cell from an in vitro cell culture. Such a host cell is useful for producing a subject rAAV variant virion, as described herein. In one embodiment, such a host cell is stably genetically modified with a nucleic acid. In other embodiments, a host cell is transiently genetically modified with a nucleic acid. Such a nucleic acid is introduced stably or transiently into a host cell, using established techniques, including, but not limited to, electroporation, calcium phosphate precipitation, liposome-mediated transfection, and the like. For stable transformation, a nucleic acid will generally further include a selectable marker, e.g., any of several well-known selectable markers such as neomycin resistance, and the like. Such a host cell is generated by introducing a nucleic acid into any of a variety of cells, e.g., mammalian cells, including, e.g., murine cells, and primate cells (e.g., human cells). Exemplary mammalian cells include, but are not limited to, primary cells and cell lines, where exemplary cell lines include, but are not limited to, HEK293 cells, HEK293T cells, COS cells, HeLa cells, Vero cells, 3T3 mouse fibroblasts, C3H10T1/2 fibroblasts, CHO cells, and the like. Exemplary host cells include, without limitation, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK293) cells (ATCC No. CRL1573), HLHepG2 cells, and the like. A host cell can also be made using a baculovirus to infect insect cells such as Sf9 cells, which produce AAV (see, e.g., U.S. Pat. No. 7,271, 002; U.S. patent application Ser. No. 12/297,958). In some embodiments, a genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a host cell further comprises an rAAV variant vector. An rAAV variant virion can be generated using such host cells. Methods of generating an rAAV virion are described in, e.g., U.S. Patent Publication No. 2005/0053922 and U.S. Patent Publication No. 2009/0202490.

The disclosure herein additionally provides a pharmaceutical composition comprising: a) the rAAV variant virion, as described above and disclosed herein; and b) a pharmaceutically acceptable carrier, diluent, excipient, or buffer. In some embodiments, the pharmaceutically acceptable carrier, diluent, excipient, or buffer is suitable for use in a human or non-human patient. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, surfactants, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ed., Lippincott, Williams, & Wilkins; and Handbook of Pharmaceutical Excipients (2000) A. H. Kibbe et al., eds., 3$^{rd}$ ed. Amer. Pharmaceutical Assoc. In some aspects of the present invention, the present invention provides a pharmaceutical composition comprising about $1\times10^8$ to about $1\times10^{16}$ recombinant viruses or $1\times10^8$ to about $1\times10^{16}$ vector genomes, wherein each said recombinant virus comprises a genome encoding one or more gene products.

Some embodiments of the invention are exemplified in the following items 1 to 54:

1. A variant adeno-associated virus (AAV) capsid protein comprising a peptide insertion in the GH-loop of the capsid protein, wherein the insertion is in AAV2 or a corresponding position in a capsid portion of a wild-type AAV serotype other than AAV2 or an AAV variant, and wherein the peptide insertion is selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

2. The variant AAV of item 1, wherein the capsid protein comprises one or more point mutations relative to AAV2 or one or more corresponding point mutations relative to other wild-type AAV serotypes or AAV variants.

3. The variant AAV of item 2, wherein the one or more point mutations is selected from the group consisting of A35P, S109T, P195L, D213N, G222S, V229I, N312K, A319T, T330A, A333S, E347K, P363L, A427D, V447F, N449D, N449K?, G453R, A490T, K527Q, N551S, A581T, Y585S, R588M, A593E, W606C, K649E, R651H, W694C, I698V, V708I, and L735Q, and is preferably selected from the group consisting of V708I, V708I+A593E, V708I+S109T, V708I+T330A, A35P, V708I+R588M, V708I+W606C, V708I+W694C, I698V, N312K+N449D+N551S+I698V+L735Q, N312K+N449D+N551S+I698V+V708I+L735Q, V708I+N449K, and V708I+G222S.

4. The variant AAV of item 1, wherein the peptide insertion is inserted following any of amino acids in positions 570-671 in VP1 of AAV2 or a corresponding position in another wild-type AAV serotype or AAV variant.

5. The variant AAV of item 4, wherein the peptide insertion is inserted following amino acid 587 in VP1 of AAV2 or a corresponding position in another AAV serotype.

6. An infectious recombinant adeno-associated virus (rAAV) virion comprising: (a) a variant AAV capsid protein according to any one of items 1-5, and a heterologous nucleic acid.

7. The rAAV of item 6, wherein the heterologous nucleic acid comprises a nucleotide sequence encoding an RNA interfering agent or a polypeptide.

8. A method of delivering a heterologous nucleic acid to a target cells, comprising contacting a target cell with the rAAV virion of item 7.

9. The method of item 8, wherein the target cell is a cardiac and/or skeletal muscle cell.

10. The method of item 8, wherein the target cell is in vitro.

11. The method of item 8, wherein the target cell is in vivo.

12. An isolated nucleic acid comprising a nucleotide sequence encoding a variant adeno-associated virus (AAV) capsid protein comprising a peptide insertion in the GH-loop of the capsid protein, wherein the insertion is in AAV2 or a corresponding position in a capsid portion of a wild-type AAV serotype other than AAV2 or an AAV variant, and wherein the peptide insertion is selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

13. An isolated host cell comprising the nucleic acid of item 12.

14. A variant adeno-associated virus (AAV) capsid protein comprising a peptide insertion relative to a parental AAV capsid protein corresponding to two adjacent amino acids at a position between amino acids 570 and 611 of VP1 of AAV2, wherein the insertion comprises the amino acid sequence $Y_1Y_2X_1X_2X_3X_4X_5X_6X_7Y_3$, and wherein $X_1$ is selected from T and N; $X_2$ is selected from N and K; $X_3$ is selected from K, I and T; $X_4$ is selected from I, Q and T; $X_5$ is selected from G, R and N; $X_6$ is selected from V, T and K; and $X_7$ is selected from T and D.

15. The variant AAV of item 14, wherein the peptide insertion is selected from the group consisting of NKIQRTD (SEQ ID NO:13), NKTTNKD (SEQ ID NO:14) and TNKIGVT (SEQ ID NO:15).

16. The variant AAV of item 15, wherein the peptide insertion is flanked by N-terminus amino acids LA and C-terminus amino acid A.

17. The variant AAV of item 15, wherein the peptide insertion is between amino acids 587 and 588 of VP1 of AAV2 or a corresponding position in another wild-type AAV serotype or AAV variant.

18. An infectious recombinant adeno-associated virus (rAAV) virion comprising: (a) a variant AAV capsid protein according to any one of items 14-17, and a heterologous nucleic acid.

19. The rAAV of item 18, wherein the heterologous nucleic acid comprises an RNA interfering agent or a nucleotide sequence encoding a polypeptide.

20. A method of delivering a heterologous nucleic acid to a target cell, comprising contacting the target cell with the rAAV virion of item 18.

21. The method of item 20, wherein the target cell is a cardiac and/or skeletal cell.

22. The method of item 21, wherein the target cell is in vitro or in vivo.

23. A variant adeno-associated virus (AAV) capsid protein comprising i) an AAV amino acid sequence at least 90% identical to a wild-type AAV selected from the group consisting of SEQ ID NOS: 1-10 and 11; and ii) one or more amino acid substitutions selected from the group consisting of P363L, P363L+V708I, P363L+E347K, V708I+A593E, V708I+A333S, V708I+S721L, V708I+A593E+N551S, V708I+A593E+K649E, V708I+A593E+S109T, V708I+A593E+S109T+K527Q, A593E+S109T, wherein the one or more substitutions are relative to AAV2 or the one or more corresponding substitutions relative to other AAV serotypes.

24. The variant AAV of item 23, wherein the capsid protein comprises a peptide insertion.

25. The variant AAV of item 24, wherein the peptide insertion is selected from the group consisting of NKIQRTD (SEQ ID NO:13), NKTTNKD (SEQ ID NO:14), TNKIGVT (SEQ ID NO:15), GNLTKGN (SEQ ID NO:16), NTVKLST (SEQ ID NO:17), SNTVKAI (SEQ ID NO:18), ASNITKA (SEQ ID NO:19), DNTVTRS (SEQ ID NO:20), NKISAKD (SEQ ID NO:21), NQDYTKT (SEQ ID NO:22), QADTTKN (SEQ ID NO:23), TNRTSPD (SEQ ID NO:24), SNTTQKT (SEQ ID NO:25), ASDSTKA (SEQ ID NO:26), LANKIQRTDA (SEQ ID NO:27), LANKTTNKDA (SEQ ID NO:28), LATNKIGVTA (SEQ ID NO:29), LAGNLTKGNA (SEQ ID NO:30), LANTVKLSTA (SEQ ID NO:31), LASNTVKAIA (SEQ ID NO:32), LAASNITKAA (SEQ ID NO:33), LADNTVTRSA (SEQ ID NO:34), LANKISAKDA (SEQ ID NO:35), LANQDYTKTA (SEQ ID NO:36), LATNKIGVTS (SEQ ID NO:37), LATNKIGVTA (SEQ ID NO:38), LAQADTTKNA (SEQ ID NO:39), LATNRTSPDA (SEQ ID NO:40), LASNTTQKTA (SEQ ID NO:41), and LAASDSTKAA (SEQ ID NO:42).

26. The variant AAV of item 23, wherein the AAV amino acid sequence is at least 95% identical to the wild-type AAV.

27. The variant AAV of item 23, wherein the AAV amino acid sequence is at least 99% identical to the wild-type AAV.

28. The variant AAV of item 23, wherein the capsid protein is a chimeric capsid protein or is an ancestral capsid protein.

29. An infectious recombinant adeno-associated virus (rAAV) virion comprising: (a) a variant AAV capsid protein according to any one of items 23-28, and a heterologous nucleic acid.

30. The rAAV of item 29, wherein the heterologous nucleic acid comprises a nucleotide sequence encoding an RNA interfering agent or a polypeptide.

31. A method of delivering a heterologous nucleic acid to a target cell, comprising contacting the target cell with the rAAV virion of item 29.

32. The method of item 31, wherein the target cell is a cardiac and/or skeletal muscle cell.

33. The method of item 32, wherein the cardiac cell is selected from the group consisting of cardiomyocytes, cardiomyoblasts, cardiac fibroblasts, and cardiac progenitor cells.

34. The method of item 31, wherein the target cell is in vitro.

35. The method of item 31, wherein the target cell is in vivo.

36. An isolated nucleic acid comprising a nucleotide sequence encoding a variant adeno-associated virus (AAV) capsid protein comprising an amino acid sequence at least 90% identical to a wild-type AAV selected from the group consisting of SEQ ID NO:1-12 or an AAV variant; and ii) one or more amino acid substitutions selected from the group consisting of P363L, P363L+V708I, P363L+E347K, V708I+A593E, V708I+A333S, V708I+S721L, V708I+A593E+N551S, V708I+A593E+K649E, V708I+A593E+S109T, V708I+A593E+S109T+K527Q, A593E+S109T.

37. An isolated host cell comprising the nucleic acid of item 36.

38. A variant adeno-associated virus (AAV) capsid protein comprising a peptide insertion in the GH-loop of the capsid protein and optionally comprising one or more point mutations, wherein the peptide insertion is selected from the group consisting of NKIQRTD (SEQ ID NO:13) and LANKIQRTDA (SEQ ID NO:26).

39. The variant AAV capsid protein according to item 38, comprising a V708I amino acid substitution.

40. The variant AAV capsid protein according to item 39, comprising a V708I+A593E, V708I+S109T, V708I+T330A, V708I+R588M or V708I+N312K+N449D+N551S+I698V+L735Q amino acid substitution.

41. The variant AAV capsid protein according to item 38, comprising an A35P amino acid substitution.

42. The variant AAV capsid protein according to item 38, comprising a N312K+N449D+N551S+I698V+L735Q amino acid substitution.

43. A variant adeno-associated virus (AAV) capsid protein comprising a peptide insertion in the GH-loop of the capsid protein and optionally comprising one or more point mutations, wherein the peptide insertion is selected from the group consisting of NKTTNKD (SEQ ID NO:14) and LANKTTNKDA (SEQ ID NO:27).

44. The variant AAV capsid protein according to item 43, comprising a V708I amino acid substitution.

45. The variant AAV capsid protein according to item 44, comprising a V708I+S109T, V708I+W694C, V708I+W606C, or V708I+N312K+N449D+N551S+I698V+L735Q amino acid substitution.

46. The variant AAV capsid protein according to item 43, comprising an I698V amino acid substitution.

47. The variant AAV capsid protein according to item 46, comprising a N312K+N449D+N551S+I698V+L735Q amino acid substitution.

48. A variant adeno-associated virus (AAV) capsid protein comprising a peptide insertion in the GH-loop of the capsid protein and optionally comprising one or more point mutations, wherein the peptide insertion is selected from the group consisting of TNKIGVT (SEQ ID NO:15), LATNKIGVTA (SEQ ID NO:28) and LATNKIGVTS (SEQ ID NO:36).

49. The variant AAV capsid protein according to item 48, comprising a V708I amino acid substitution.

50. The variant AAV capsid protein according to item 49, comprising a V708I+N449K, V708I+G222S, or V708I+N312K+N449D+N551S+I698V+L735Q amino acid substitution.

51. The variant AAV capsid protein according to item 48, comprising a N312K+N449D+N551S+I698V+L735Q amino acid substitution.

52. A variant adeno-associated virus (AAV) capsid protein comprising the sequence of SEQ ID NO:62 or a sequence at least 90% identical thereto, wherein the variant AAV capsid proteins comprises the following amino acid substitutions relative to AAV5 capsid: V229I+A490T+A581T.

53. The variant AAV capsid protein according to item 52, further comprising a Y585S or V447F amino acid substitution relative to AA5 capsid.

54. A variant adeno-associated virus (AAV) capsid protein comprising the sequence of SEQ ID NO:63 or a sequence at least 90% identical thereto, wherein the variant AAV capsid proteins comprises the following amino acid substitutions relative to AAV5 capsid: V229I+A427D+A490T+A581T.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Intravenous Injection and Tissue Harvesting. A single male cynomolgus macaque (*Macaca fascicularis*) age 3-10 years old and weighing at least 3 kg was dosed via intravenous injection via the saphenous vein for each round of selection. The animal was anesthetized and 1-5 mL of the library (in the first round, the library consists of variants generated using all mutagenesis techniques described in FIG. 1A; in each subsequent round, the variants isolated from the previous round), in some cases pre-incubated with human IVIG for 30 minutes at 37° C., was administered.

Euthanasia was performed by trained veterinary staff using 100 mg/kg pentobarbital sodium intravenous injection on day 14±3 or 21±3, depending on the selection. The cardiac and/or skeletal muscle tissue from the quadriceps was removed, and DNA was isolated from the tissue. In some cases, the cardiac tissue was divided into several regions: the atrium, ventricular septum, left papillary muscle, right papillary muscle, left ventricle, and right ventricle.

Directed Evolution. The directed evolution process is shown in FIG. 1A-1E. Briefly, a viral capsid library comprising 20+ proprietary combinations of DNA mutation technique and cap genes is created (FIG. 1A). Viruses are then packaged (FIG. 11B)—such that each particle is composed of a mutant capsid surrounding the cap gene encoding that capsid—and purified. The capsid library is placed under selective pressure in vivo. The tissue or cellular material of interest is harvested to isolate AAV variants that have successfully infected that target, and the successful viruses are recovered. Successful clones are enriched through repeated selection (Stage 1—FIG. 1D). Selected cap genes then undergo proprietary re-diversification and are enriched through further selection steps to iteratively increase viral fitness (Stage 2—FIG. 1D). Variants identified during Vector Selection Stages 1 and 2 demonstrate the ability to transduce primate muscle cells (FIG. 1E).

Figure 2:
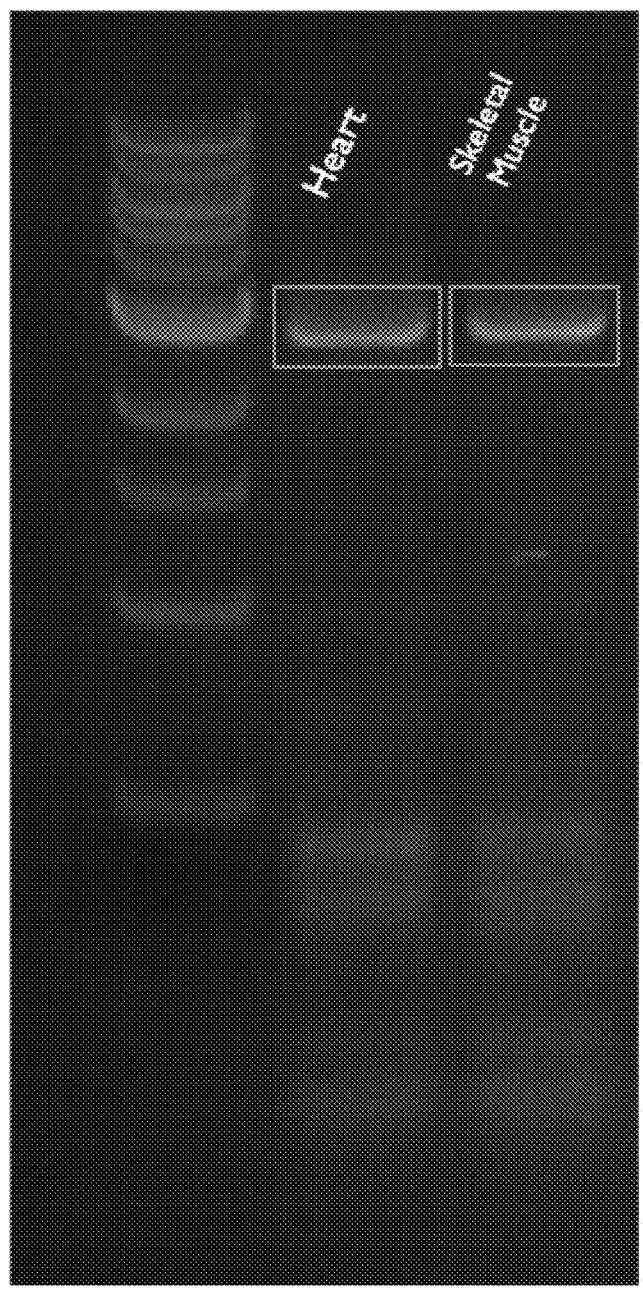
FIG. 2 shows PCR amplification of viral genomes from the heart and skeletal muscle tissues from a representative round of selection. Bands within boxes represent successful amplification of viral genomes.
Figure 4B:
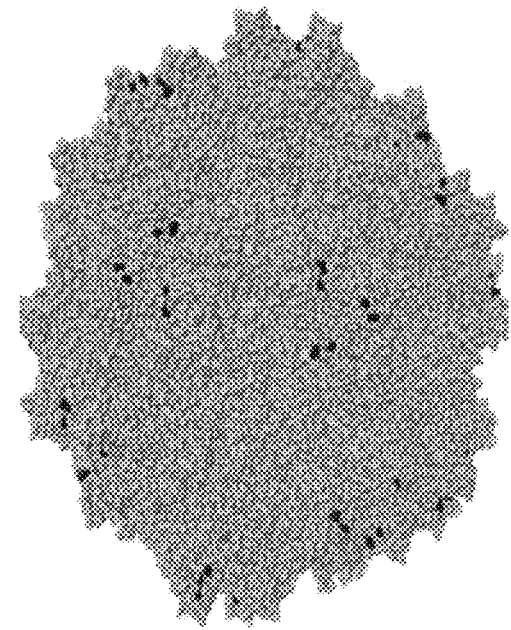
FIGS. 4A-4C FIG. 4A is a representative three-dimensional model of AAV2 containing a random heptamer following amino acid 587 and a V708I substitution.
Figure 4C:
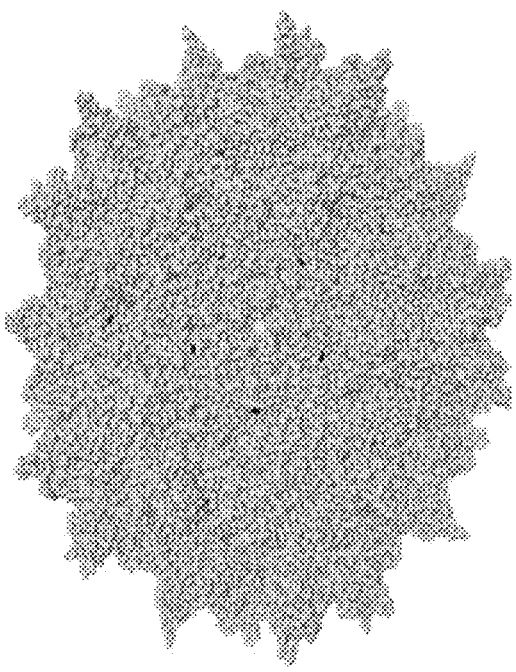
Figure 4A:
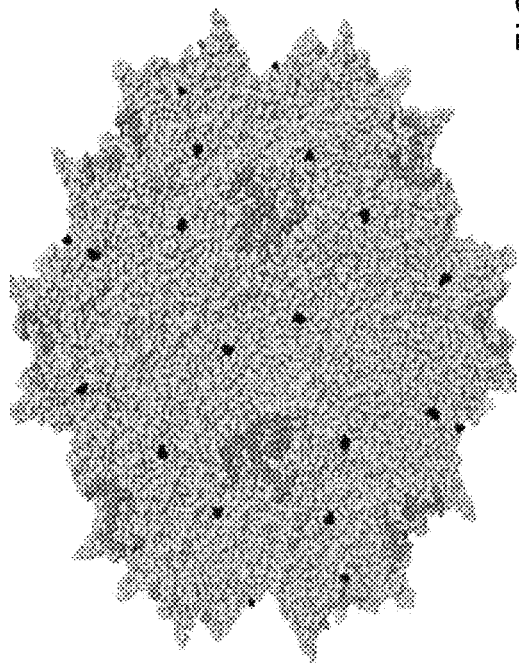
Figure 6A:
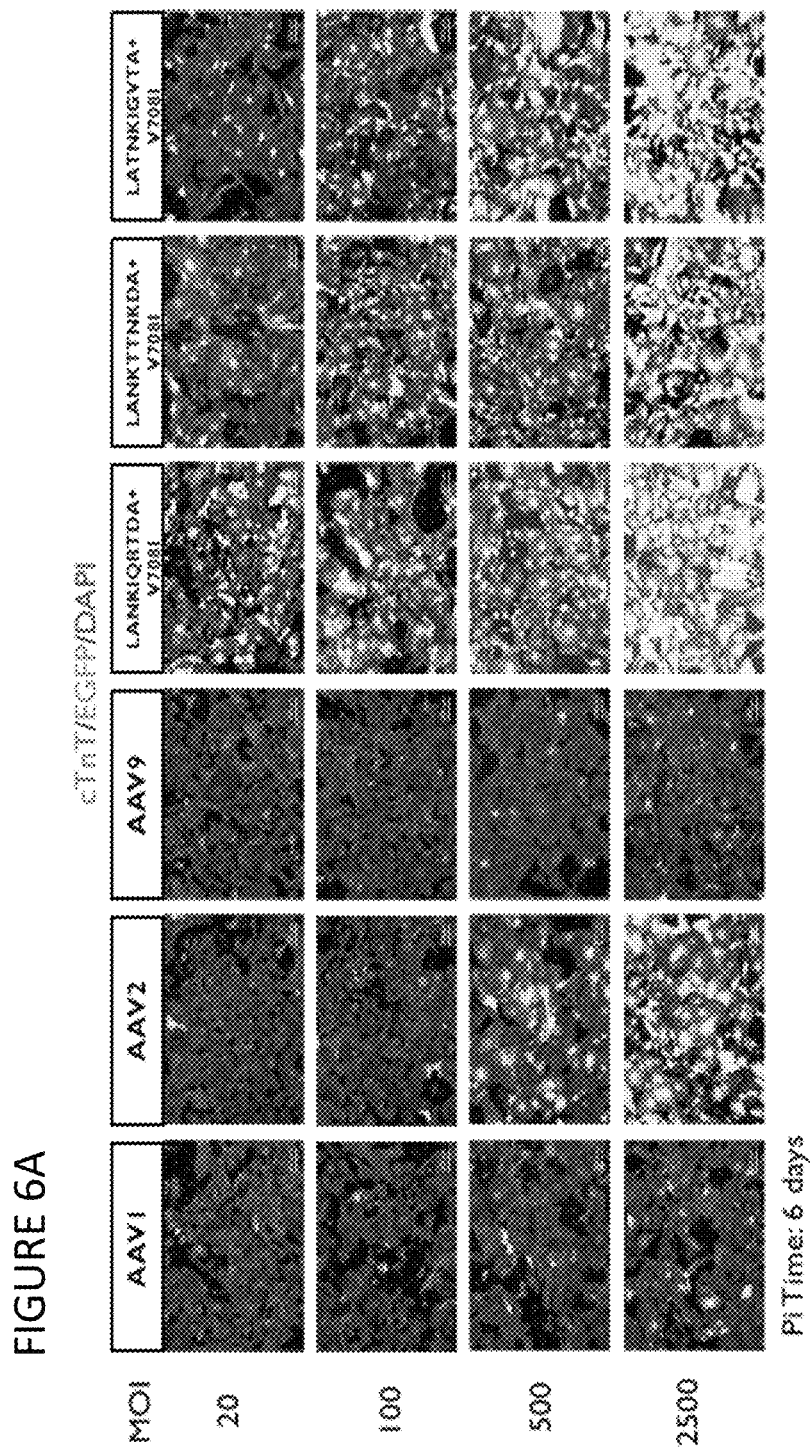
Figure 6B:
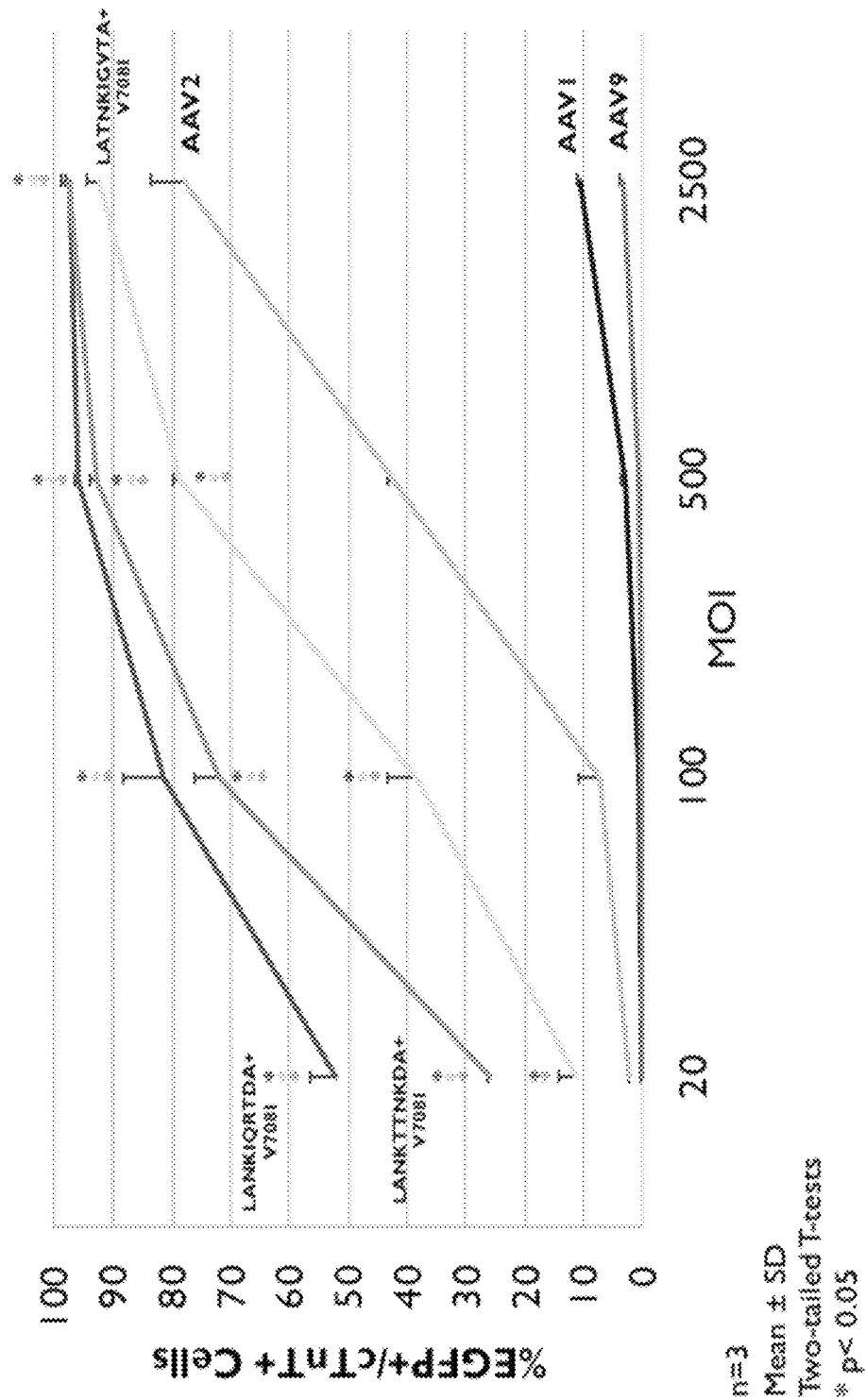
Figure 6C:
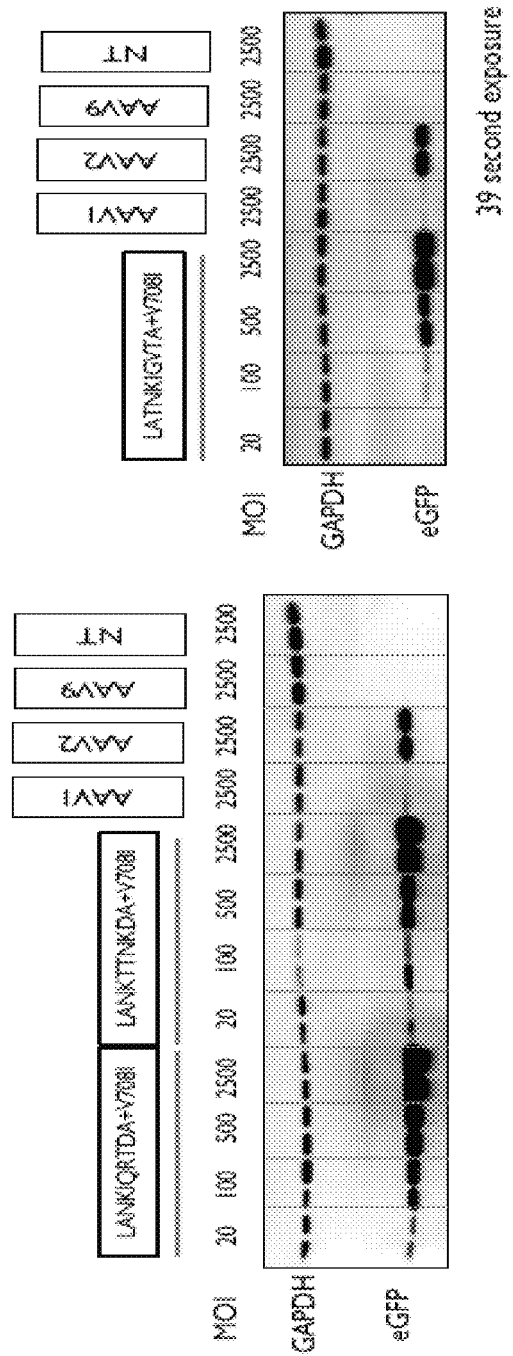
Figure 6D:
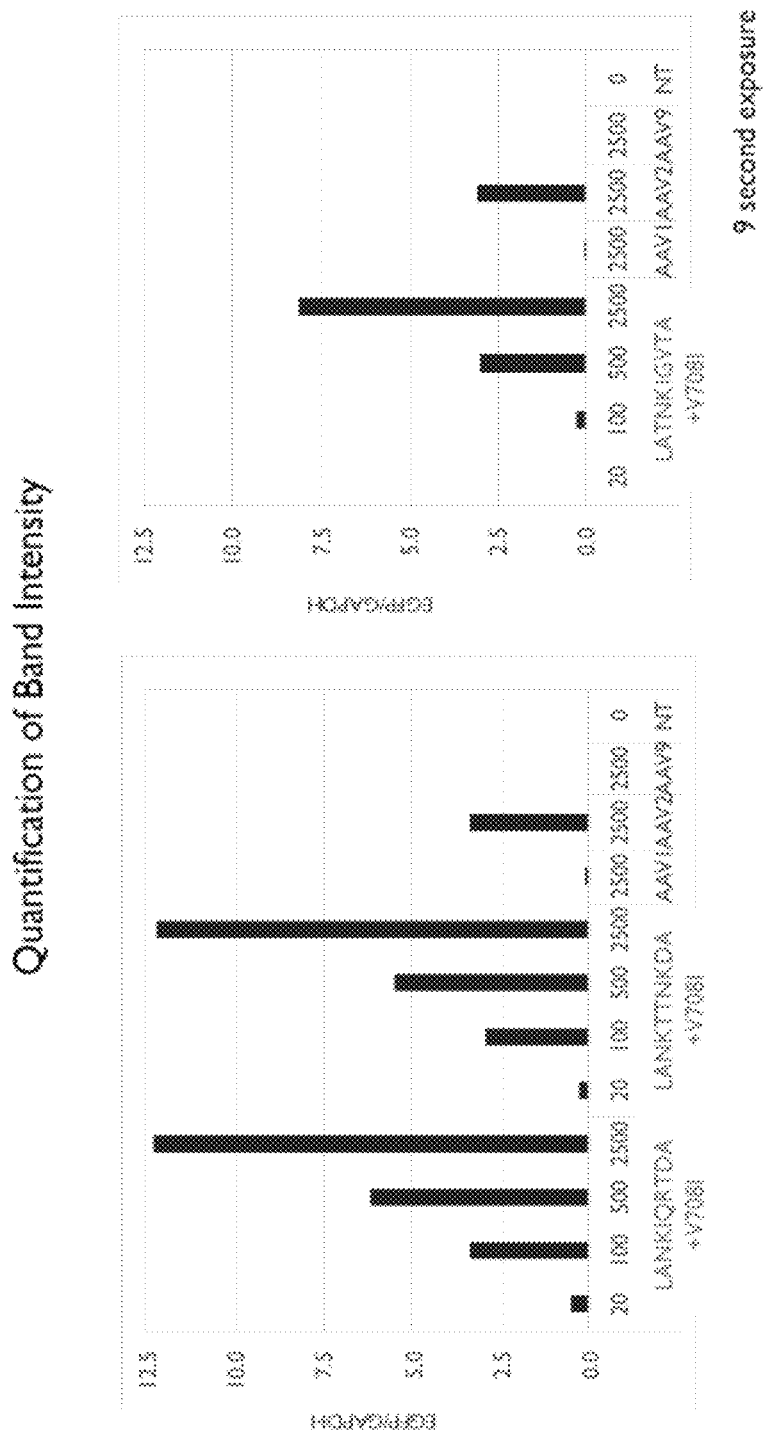

Successful Recovery of AAV Capsid Genomes. The capsids recovered from each round of selection were used to package the library injected to initiate the subsequent round of selection. Recovery of capsid genes from tissue represents successful internalization of library vectors into the tissue of interest. Recovery of viral genomes from cardiac and skeletal muscle tissue from a representative round of selection are shown in FIG. 2. Bands within boxes represent successful recovery of viral genomes.

Sequencing Analysis. During rounds 3-4 of selections including the selective pressure of intravenous delivery to cardiac tissue or skeletal muscle tissue and rounds 1-2 of a selection including the selective pressure of intravenous delivery in the presence of neutralizing antibodies to cardiac tissue, sequencing was performed on individual clones within the library to determine the frequency of variants within the population. Variants were evaluated for the presence of motifs within the sequencing data. Variants were grouped into motifs based on the presence of a unifying variation (for example, a specific point mutation or specific peptide insertion sequence in a consistent location within the capsid) that occurred in multiple sequences. Motifs representing at least 5% of the sequenced population in two or more rounds of the selection or at least 10% of the sequenced population in one or more rounds of the selection are represented in FIG. 3A (Round 4 sequencing analysis for the selective pressure of intravenous delivery to cardiac tissue), FIG. 3B (Round 2 sequencing analysis for the selective pressure of intravenous delivery in the presence of neutralizing antibodies to cardiac tissue), and FIG. 3C (provides Round 3 sequencing analysis for the selective pressure of intravenous delivery to skeletal muscle tissue.

Several representative clones that were identified as conferring increased infectivity of cardiac and/or skeletal muscle cells are listed in Table 1 below (each clone contains the identified substitution(s) and/or peptide insertion and is otherwise identical to SEQ ID NO:2; the selection round, number of sequences and frequency (in parentheses) are listed for each clone):

TABLE 1

Amino acid sequence modifications to the AAV VP1 capsid protein that confer increased infectivity of cardiac and/or skeletal muscle cells. Substitutions listed in column 2 are based on the amino acid sequence for wild type AAV2, i.e. in the absence of inserted peptide. "Cardiac + NAb" in column 5 indicates that the amino acid sequence modifications should confer increased resistance to neutralization by anti-AAV antibodies in addition to increased infectivity of cardiac muscle cells.

| Insertion | Substitution | Cardiac | Cardiac + NAb | Skeletal Muscle |
|---|---|---|---|---|
| 588~LANKIQRTDA~(SEQ ID NO: 27) | None | Round 3: 6 (9.68%) Round 4: 11 (26.83%) | Round 1: 2 (1.41%) Round 2: 1 (0.81%) | Round 3: 1 (1.23%) |
| 588~LANKIQRTDA~(SEQ ID NO: 27) | +A35P | Round 4: 1 (2.44%) | — | — |
| 588~LANKIQRTDA~(SEQ ID NO: 27) | +S109T + V708I | Round 3: 1 (1.61%) Round 4: 2 (4.88%) | — | — |
| 588~LANKIQRTDA~(SEQ ID NO: 27) | +R588M + V708I | — | Round 1: 1 (0.70%) | — |
| 588~LANKIQRTDA~(SEQ ID NO: 27) | +A593E + V708I | Round 3: 1 (1.61%) | — | — |
| 588~LANKIQRTDA~(SEQ ID NO: 27) | +V708I | Round 3: 13 (20.97%) Round 4: 10 (23.26%) | Round 1: 1 (0.70%) | — |
| 588~LANKTTNKDA~(SEQ ID NO: 28) | None | Round 4: 2 (4.88%) | Round 1: 10 (7.04%) Round 2: 8 (6.50%) | — |
| 588~LANKTTNKDA~(SEQ ID NO: 28) | +S109T + V708I | Round 4: 1 (2.44%) | — | — |
| 588~LANKTTNKDA~(SEQ ID NO: 28) | +W694C + V708I | Round 4: 1 (2.44%) | — | — |
| 588~LANKTTNKDA~(SEQ ID NO: 28) | +I698V | — | Round 1: 1 (0.70%) | — |
| 588~LANKTTNKDA~(SEQ ID NO: 28) | +W606C + V708I | — | Round 2: 1 (0.81%) | — |

TABLE 1-continued

Amino acid sequence modifications to the AAV VP1 capsid protein that confer increased infectivity of cardiac and/or skeletal muscle cells. Substitutions listed in column 2 are based on the amino acid sequence for wild type AAV2, i.e. in the absence of inserted peptide. "Cardiac + NAb" in column 5 indicates that the amino acid sequence modifications should confer increased resistance to neutralization by anti-AAV antibodies in addition to increased infectivity of cardiac muscle cells.

| Insertion | Substitution | Cardiac | Cardiac + NAb | Skeletal Muscle |
|---|---|---|---|---|
| 588~LANKTTNKDA~(SEQ ID NO: 28) | +V708I | Round 3: 6 (9.68%) Round 4: 3 (7.32%) | Round 1: 4 (2.82%) Round 2: 10 (8.13%) | — |
| 588~LATNKIGVTA~(SEQ ID NO: 29) | +V708I | Round 4: 1 (2.44%) | — | — |
| 588~LAQADTTKNA~(SEQ ID NO: 39) | None | — | Round 1: 23 (16.02%) Round 2: 21 (17.07%) | — |
| 588~LAQADTTKNA~(SEQ ID NO: 39) | +D213N | — | Round 2: 1 (0.81%) | — |
| 588~LAQADTTKNA~(SEQ ID NO: 39) | +G453R | — | Round 1: 1 (0.70%) | — |
| 588~LAQADTTKNA~(SEQ ID NO: 39) | +V708I | Round 4: 1 (2.44%) | Round 1: 3 (2.11%) Round 2: 3 (2.44%) | — |
| 588~LAQADTTKNA~(SEQ ID NO: 39) | +P363L | — | Round 1: 1 (0.70%) | — |
| 588~LANQDYTKTA~(SEQ ID NO: 36) | None | — | Round 1: 1 (0.70%) | — |
| 588~LANQDYTKTA~(SEQ ID NO: 36) | +I698V | — | Round 2: 2 (1.63%) | — |
| 588~LANQDYTKTA~(SEQ ID NO: 36) | +V708I | — | Round 1: 1 (0.70%) | — |
| 588~LATNRTSPDA~(SEQ ID NO: 40) | +V708I | — | Round 2: 1 (0.81%) | — |
| 588~LAASDSTKAA~(SEQ ID NO: 42) | None | — | — | Round 3: 1 (1.23%) |
| 588~LAASDSTKAA~(SEQ ID NO: 42) | +V708I | Round 3: 2 (3.23%) | — | — |
| 588~LAASNITKAA~(SEQ ID NO: 33) | None | — | Round 1: 2 (1.41%) Round 2: 8 (6.50%) | — |
| 588~LAASNITKAA~(SEQ ID NO: 33) | +V708I | — | Round 1: 6 (4.23%) Round 2: 11 (8.94%) | — |
| 588~LAGNLTKGNA~(SEQ ID NO: 30) | None | Round 3: 4 (6.44%) | Round 1: 6 (4.23%) Round 2: 3 (2.44%) | — |
| 588~LAGNLTKGNA~(SEQ ID NO: 30) | +S109T + V708I | Round 3: 2 (3.23%) | — | — |
| 588~LAGNLTKGNA~(SEQ ID NO: 30) | +A139T + P195L | — | Round 1: 1 (0.70%) | — |
| 588~LAGNLTKGNA~(SEQ ID NO: 30) | +P363L + V708I | — | Round 1: 1 (0.70%) | — |

TABLE 1-continued

Amino acid sequence modifications to the AAV VP1 capsid protein that confer increased infectivity of cardiac and/or skeletal muscle cells. Substitutions listed in column 2 are based on the amino acid sequence for wild type AAV2, i.e. in the absence of inserted peptide. "Cardiac + NAb" in column 5 indicates that the amino acid sequence modifications should confer increased resistance to neutralization by anti-AAV antibodies in addition to increased infectivity of cardiac muscle cells.

| Insertion | Substitution | Cardiac | Cardiac + NAb | Skeletal Muscle |
|---|---|---|---|---|
| 588~LAGNLTKGNA~(SEQ ID NO: 30) | +R651H | — | Round 2: 1 (0.81%) | — |
| 588~LAGNLTKGNA~(SEQ ID NO: 30) | +V708I | Round 3: 2 (3.23%) | Round 1: 1 (0.70%) Round 2: 2 (1.63%) | — |
| 588~LAGNLTKGNA~(SEQ ID NO: 30) | +P363L | — | Round 1: 1 (0.70%) | — |
| 588~LADNTVTRSA~(SEQ ID NO: 34) | None | — | Round 1: 9 (6.34%) Round 2: 6 (4.88%) | — |
| 588~LADNTVTRSA~(SEQ ID NO: 34) | +I698V | — | Round 2: 1 (0.81%) | — |
| 588~LADNTVTRSA~(SEQ ID NO: 34) | +V708I | — | Round 1: 1 (0.70%) Round 2: 2 (1.63%) | — |
| 588~LANTVKLSTA~(SEQ ID NO: 31) | None | — | Round 1: 3 (2.11%) Round 2: 7 (5.69%) | — |
| 588~LANTVKLSTA~(SEQ ID NO: 31) | +V708I | — | Round 2: 8 (6.50%) | — |
| 588~LASNTVKAIA~(SEQ ID NO: 32) | None | Round 3: 2 (3.23%) Round 4: 1 (2.44%) | — | — |
| 588~LASNTVKAIA~(SEQ ID NO: 32) | +V708I | Round 4: 1 (2.44%) | — | — |
| 588~LATNKIGVTS~(SEQ ID NO: 37) | None | Round 4: 1 (2.44%) | — | — |
| 588~LASNTTQKTA~(SEQ ID NO: 41) | None | — | — | Round 3: 2 (2.46%) |
| 588~LANKISAKDA~(SEQ ID NO: 35) | None | — | Round 2: 3 (2.44%) | — |
| 588~LANKISAKDA~(SEQ ID NO: 35) | +V708I | — | Round 2: 2 (1.63%) | — |
| None | P34A | — | — | Round 4: 2 (10%) |
| None | P34S | — | Round 1: 1 (0.70%) | — |
| None | P64S | — | — | Round 4: 1 (5.00%) |
| None | S109T + P235S | — | — | Round 4: 1 (5.00%) |
| None | Q120R | — | — | Round 4: 1 (5.00%) |

TABLE 1-continued

Amino acid sequence modifications to the AAV VP1 capsid protein that confer increased infectivity of cardiac and/or skeletal muscle cells. Substitutions listed in column 2 are based on the amino acid sequence for wild type AAV2, i.e. in the absence of inserted peptide. "Cardiac + NAb" in column 5 indicates that the amino acid sequence modifications should confer increased resistance to neutralization by anti-AAV antibodies in addition to increased infectivity of cardiac muscle cells.

| Insertion | Substitution | Cardiac | Cardiac + NAb | Skeletal Muscle |
|---|---|---|---|---|
| None | A193V | — | — | Round 3: 1 (1.23%) |
| None | T277N | — | — | Round 4: 1 (5.00%) |
| None | P351L | — | — | Round 4: 1 (5.00%) |
| None | P363L | — | Round 1: 13 (9.15%) | Round 3: 34 (41.98%) Round 4: 4 (20.00%) |
| None | P363L + E347K | — | — | Round 3: 1 (1.23%) |
| None | P363L + V708I | — | Round 1: 2 (1.41%) | — |
| None | S427T + I698V | — | Round 1: 1 (0.70%) | — |
| None | Q440K | — | — | Round 3: 1 (1.23%) |
| None | Y444F | — | — | Round 4: 1 (5.00%) |
| None | N449D | — | — | Round 4: 1 (5.00%) |
| None | T568N | — | — | Round 3: 1 (1.23%) |
| None | A593E | Round 4: 3 (7.32%) | Round 1: 1 (0.70%) | Round 3: 31 (38.27%) Round 4: 2 (10%) |
| None | S109T + A593E | — | — | Round 3: 2 (2.47%) |
| None | S109T + K527Q + A593E + V708I | Round 3: 1 (1.61%) | — | — |
| None | S109T + A593E + V708I | Round 3: 1 (1.61%) | — | — |
| None | A593E + N551S + V708I | — | — | Round 3: 1 (1.23%) |
| None | A593E + K649E + V708I | Round 3: 1 (1.61%) | — | — |
| None | A593E + V708I | Round 3: 12 (19.35%) | Round 1: 5 (3.52%) | Round 3: 1 (1.23%) |
| None | I698V | — | — | Round 4: 1 (5.00%) |
| None | V708I | Round 3: 6 (9.68%) Round 4: 2 (4.88%) | Round 1: 10 (7.04%) | Round 3: 1 (1.23%) Round 4: 1 (5.00%) |
| None | V708I + A333S | — | — | Round 3: 1 (1.23%) |

TABLE 1-continued

Amino acid sequence modifications to the AAV VP1 capsid protein that confer increased infectivity of cardiac and/or skeletal muscle cells were generated from a human embryonic stem cell line, ESI-017, by modulation of Wnt signaling using small molecules. After 14 days of cardiac mesoderm induction, cultures were further enriched for cardiomyocytes by glucose deprivation. After approximately 24 days of differentiation, the majority of cells expressed the cardiac myocyte marker, cardiac Troponin T (cTnT), and a ventricular-specific marker, MLC-2V. The generated cardiomyocytes were evaluated for expression of gap junction protein Connexin 43, membrane potential fluctuation, calcium handling, and contractile function to ensure that the generated cardiomyocytes reached a mature state prior to vector characterization.

Figure 7A:
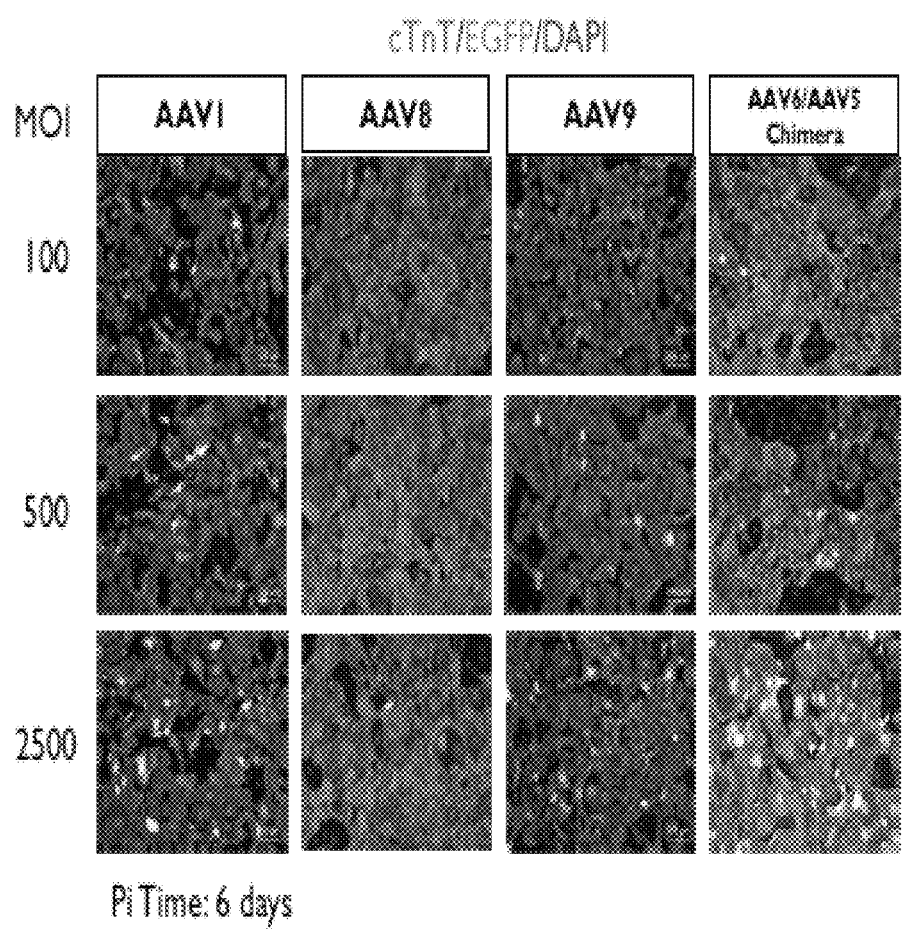
Figure 7C:
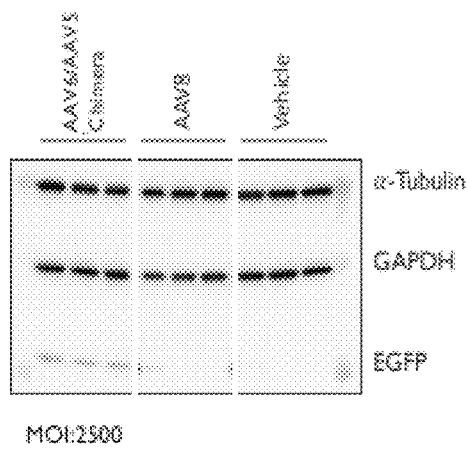
Figure 7D:
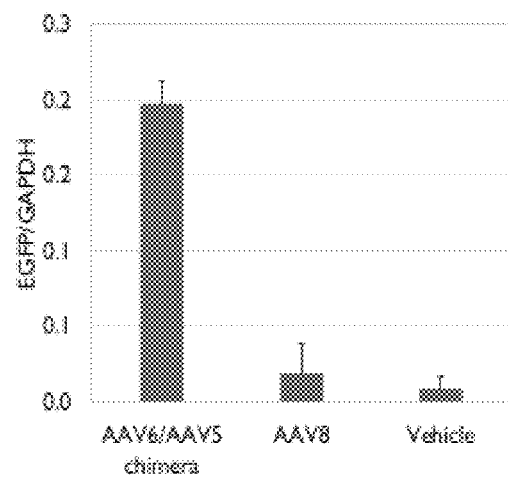
Figure 7E:
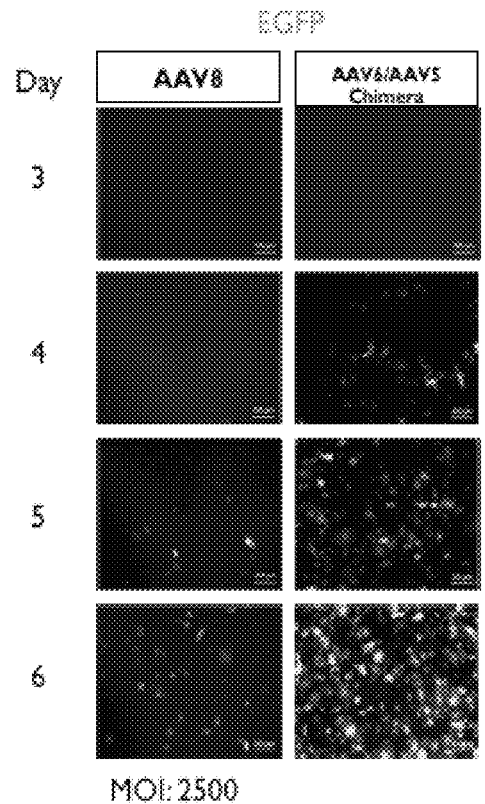

Relative to AAV1, AAV8, and AAV9, the AAV6/AAV5 chimera provided for significantly higher transduction efficiency of and transgene expression in human cardiomyocyte cultures six days post-infection as determined by immunofluorescence (FIG. 7A), flow cytometry (FIG. 7B), and Western blot analysis (FIGS. 7C-D). Furthermore, relative to AAV8, the AAV6/AAV5 chimera provided for faster onset of gene expression in human cardiomyocyte cultures, as determined by immunofluorescence (FIG. 7E). Relative to AAV8 and AAV9, the number of infectious units per administered viral genome were multiple orders of magnitude higher for the AAV6/AAV5 chimera (FIG. 10A). This study illustrates the superior ability of SEQ ID NO:62-comprising AAV capsid variants to deliver genes to cardiac cells.

Example 4

The cell tropism of recombinant AAV virions comprising the novel AAV variants LANKIQRTDA+V708I (SEQ ID NO:43), LANKTTNKDA+V708I (SEQ ID NO:48), and AAV6/AAV5 chimera for skeletal myofibers was assessed in vitro using skeletal myofibers generated from primary human myoblasts.

Recombinant AAV virions comprising either an AAV8 capsid, an AAV9 capsid, the novel variant capsid LANKIQRTDA+V708I (SEQ ID NO:43), the novel variant capsid LANKTTNKDA+V708I (SEQ ID NO:48), or the novel variant capsid AAV6/AAV5 chimera and a genome comprising a green fluorescent protein (EGFP) transgene operably linked to a CAG promoter (AAV8.CAG.EGFP, AAV9.CAG.EGFP, LANKIQRTDA+V708I (SEQ ID NO:43).CAG.EGFP, LANKTTNKDA+V708I (SEQ ID NO:48).CAG.EGFP, and AAV6/AAV5 chimera.CAG.GFP, respectively) were manufactured using standard methods. Skeletal myofibers were generated from primary human skeletal myoblasts obtained from a healthy 51 year old male (Cook Myosites). The myoblasts were differentiated for 30 days to form mature multinucleated skeletal muscle fibers. The generated skeletal myofibers were evaluated for expression of Myosin Heavy Chain (MHC) and Dystrophin to ensure that the majority of the generated skeletal myofibers reached a mature state prior to vector characterization.

Figure 8A:
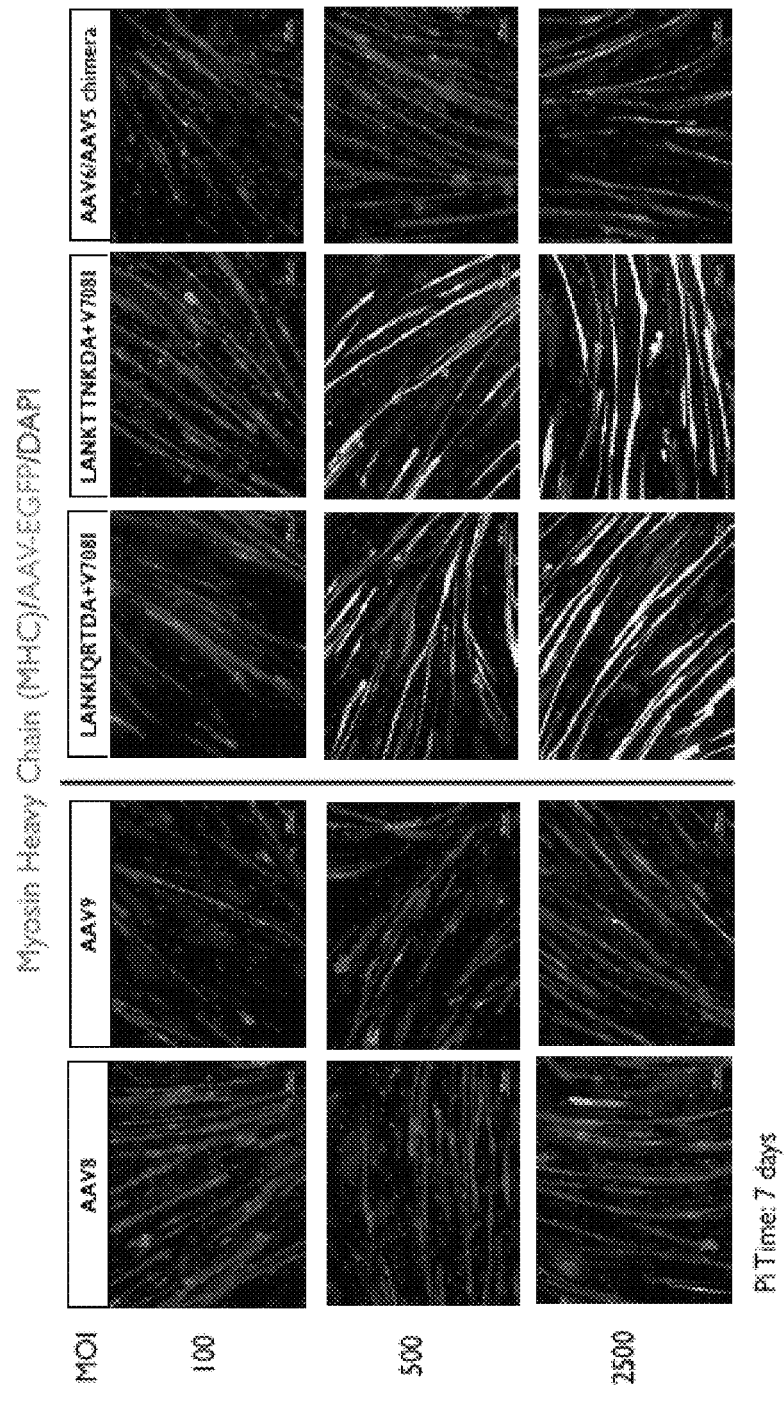
FIGS. 8A-C provide data on the transduction of human skeletal myofibers in vitro by recombinant AAV virus comprising the novel AAV variant LANKIQRTDA+V708I (SEQ ID NO:43) capsid, the novel AAV variant LANKTTNKDA+V708I (SEQ ID NO:48) capsid, and the novel AAV variant AAV6/AAV5 chimera capsid, each expressing a GFP transgene under the control of the CAG promoter.
Figure 8B:
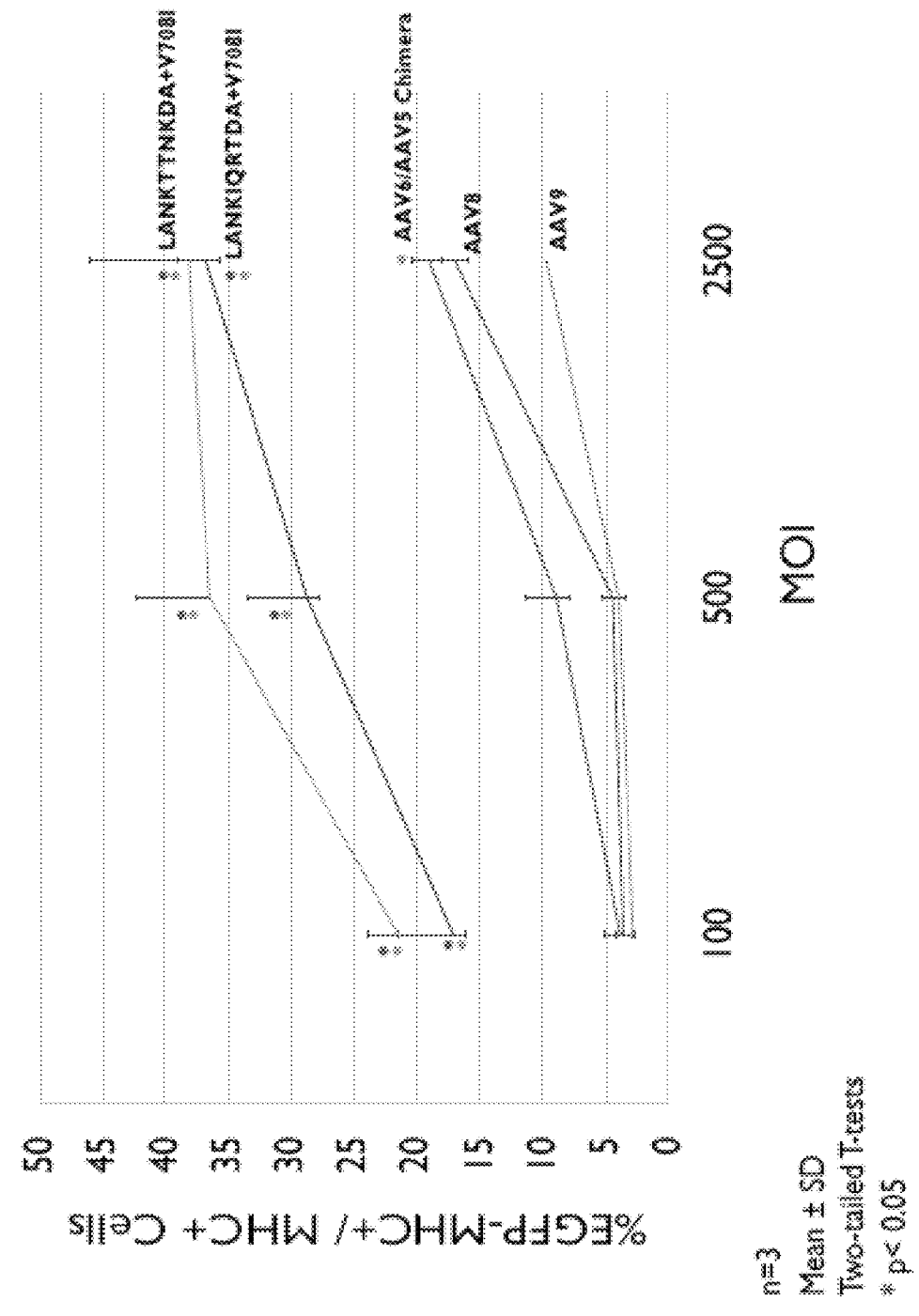
Figure 8C:
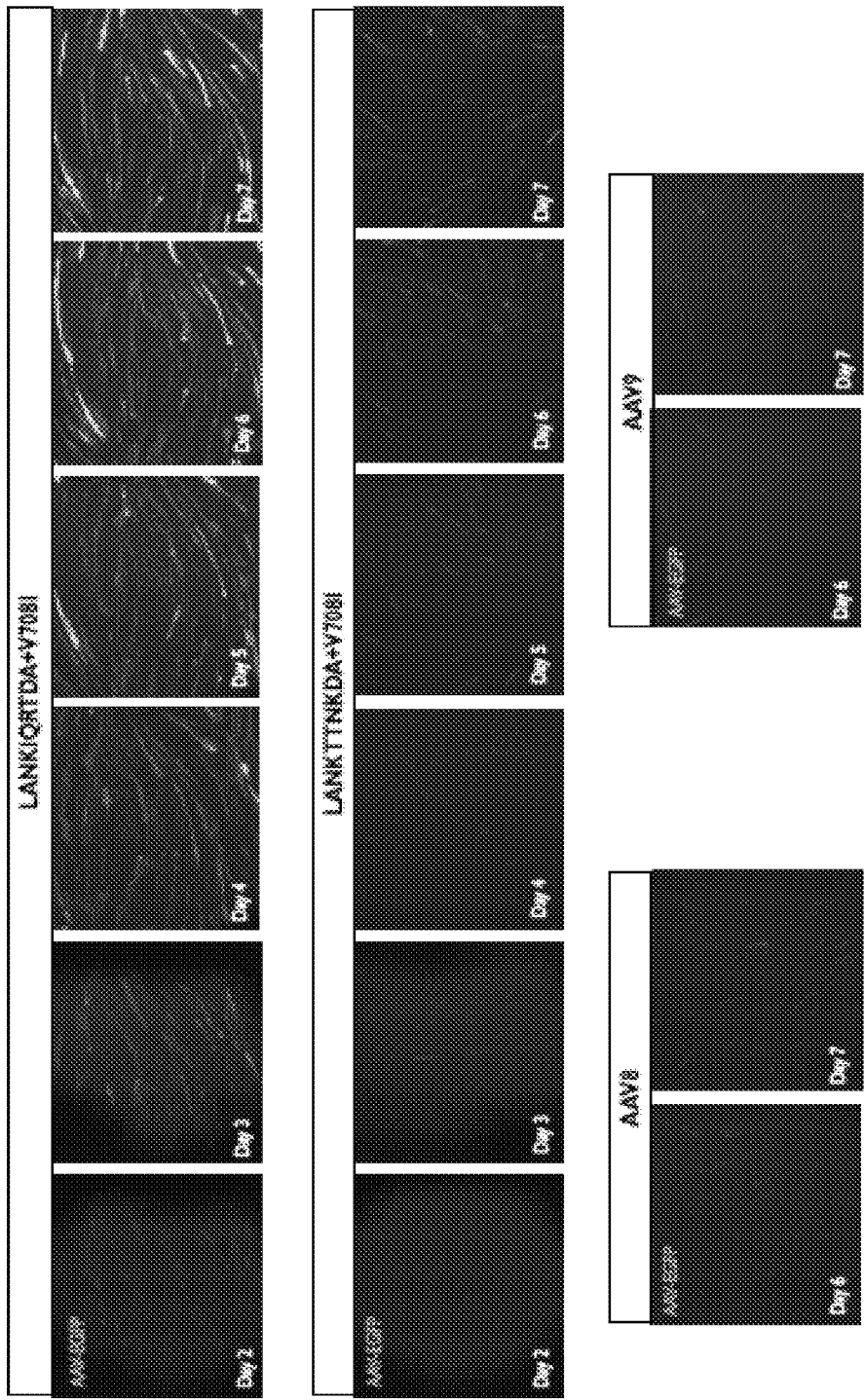
Figure 10B:
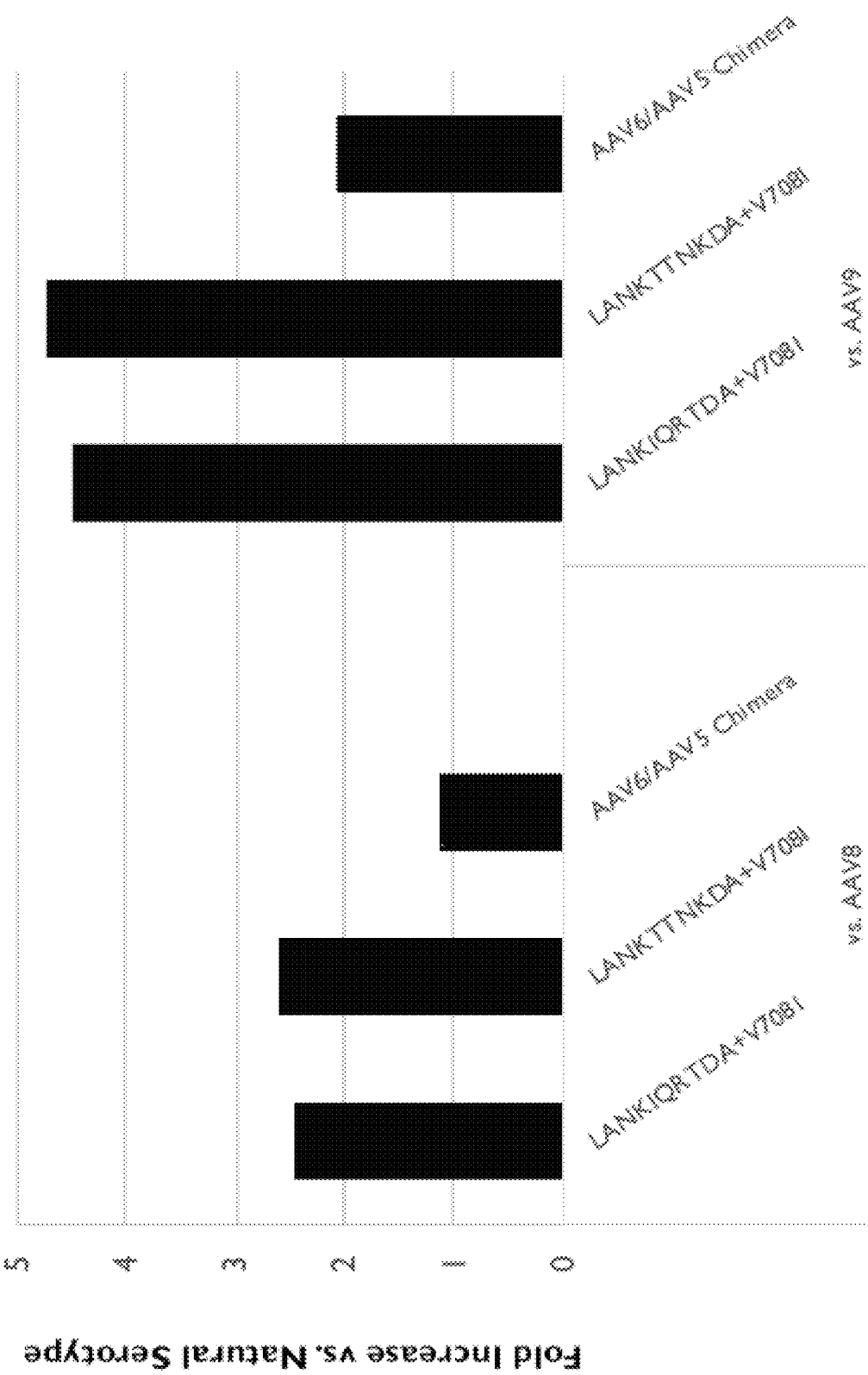

Relative to AAV8 and AAV9, the LANKIQRTDA+V708I (SEQ ID NO:43), LANKTTNKDA+V708I (SEQ ID N0:48), and AAV6/AAV5 chimera provided for significantly higher transduction efficiency of and transgene expression in human skeletal myofiber cultures seven days post-infection as determined by immunofluorescence (FIG. 8A) and flow cytometry (FIG. 8B). Furthermore, relative to AAV8 and AAV9, LANKIQRTDA+V708I (SEQ ID NO:43) and LANKTTNKDA+V708I (SEQ ID NO:48) provided for faster onset of gene expression in human skeletal myofiber cultures, as determined by immunofluorescence (FIG. 8C). Relative to AAV8 and AAV9, the number of infectious units per administered viral genome were multiple fold magnitude higher for LANKIQRTDA+V708I (SEQ ID NO:43), LANKTTNKDA+V708I (SEQ ID NO:48), and the AAV6/5 chimera (FIG. 10B). This study illustrates the superior ability of NKIQRTD (SEQ ID NO:13)-, NKTTNKD (SEQ ID NO:14)-, and SEQ ID NO:62-comprising variants to deliver genes to skeletal myofibers.

Example 5

The cell tropism of recombinant AAV virions comprising the novel AAV variants LANKIQRTDA+V708I (SEQ ID NO:43), LANKTTNKDA+V708I (SEQ ID NO:48), and AAV6/AAV5 chimera for skeletal muscle progenitor cells was assessed in vitro using skeletal muscle progenitor cells generated from fibroblast-derived human induced pluripotent stem cells (FB-iPSC) or human embryonic stem cells (ESC).

Recombinant AAV virions comprising either an AAV9 capsid, the novel variant capsid LANKIQRTDA+V708I (SEQ ID NO:43), the novel variant capsid LANKTTNKDA+V708I (SEQ ID NO:48), or the novel variant capsid AAV6/AAV5 chimera and a genome comprising a green fluorescent protein (EGFP) transgene operably linked to a CAG promoter (AAV8.CAG.EGFP, AAV9.CAG.EGFP, LANKIQRTDA+V708I (SEQ ID NO:43).CAG.EGFP, LANKTTNKDA+V708I (SEQ ID NO:48).CAG.EGFP, and AAV6/AAV5 chimera.CAG.GFP, respectively) were manufactured using standard methods. Skeletal muscle progenitors were generated from a human embryonic stem cell line, ESI-017 (ESI-BIO) following the differentiation strategy described in Shelton et al. Methods, 2016 with minor modifications. After approximately 40 days of differentiation, lineage restriction to skeletal muscle progenitors was confirmed by expression of PAX7, and MyoD in the majority of cells prior to using the cultures for vector characterization.

Figure 9A:
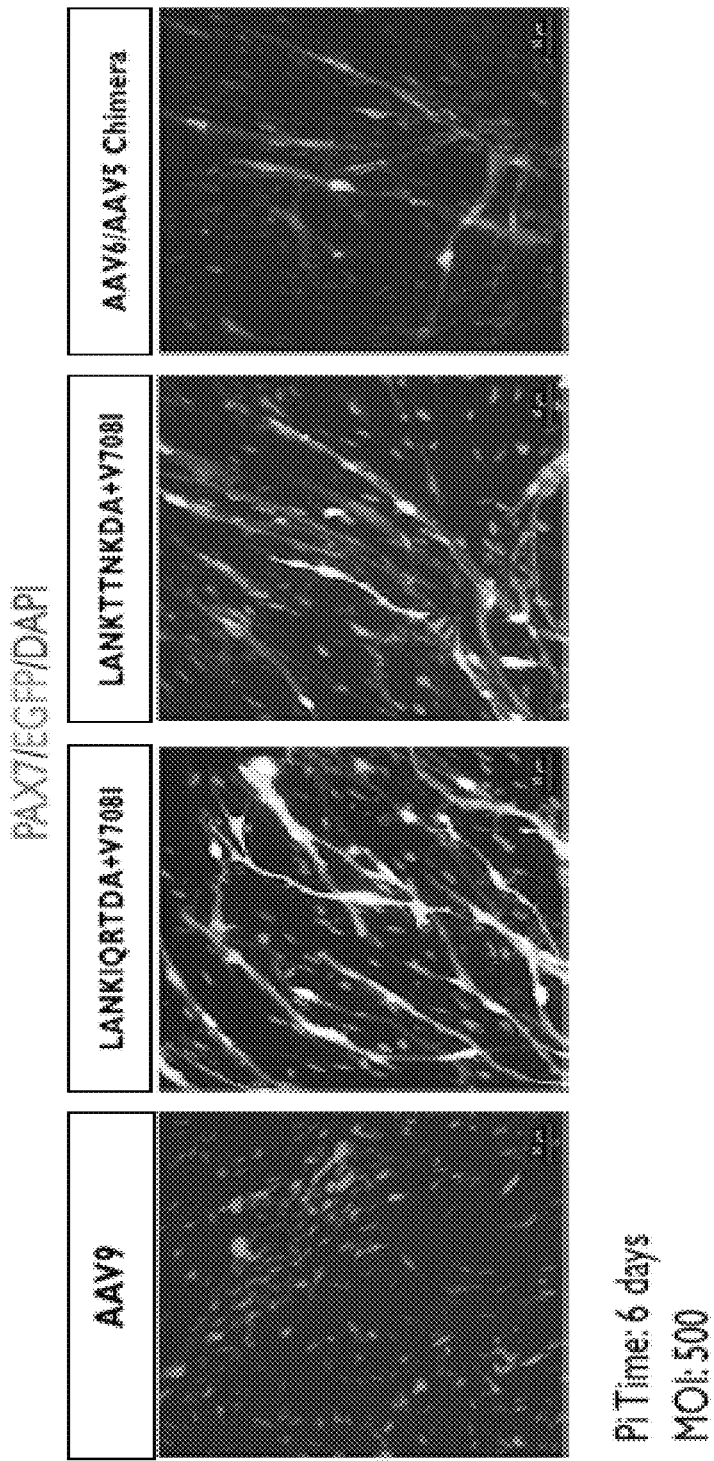
FIGS. 9A-B provide data on the transduction of human muscle progenitor cells in vitro by recombinant AAV virus comprising the novel AAV variant LANKIQRTDA+V708I (SEQ ID NO:43) capsid, the novel AAV variant LANKTTNKDA+V708I (SEQ ID NO:48) capsid, and the novel AAV variant AAV6/AAV5 chimera capsid, each expressing a GFP transgene under the control of the CAG promoter.
Figure 9B:
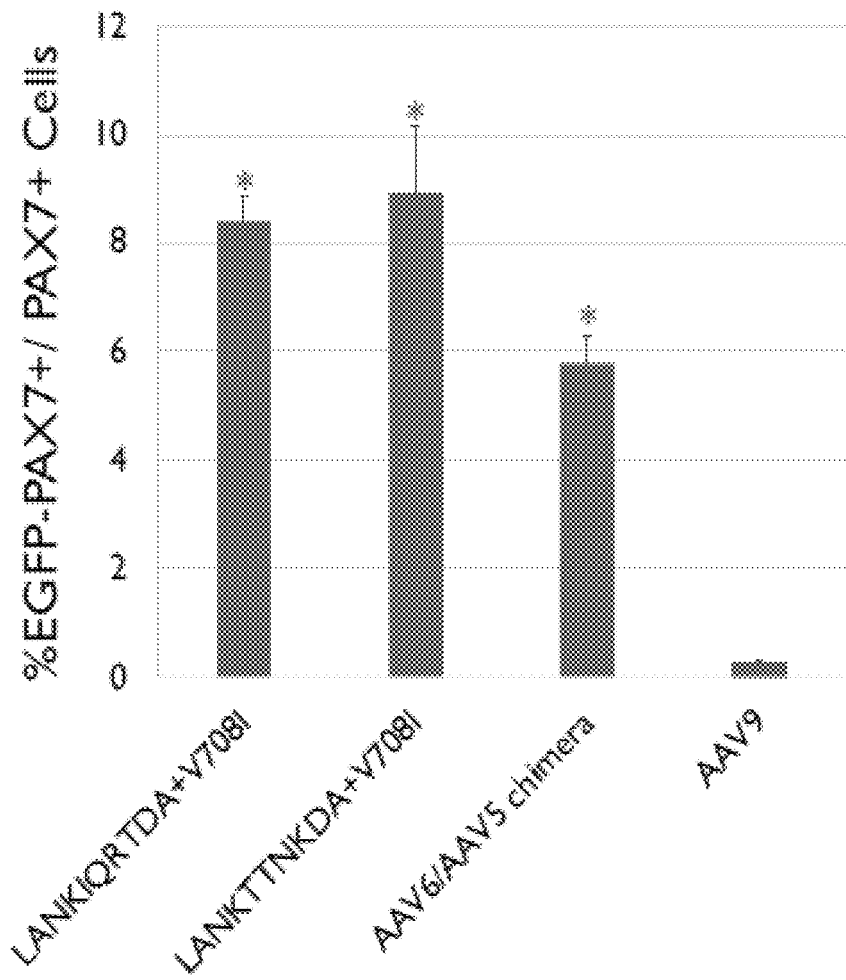

Relative to AAV9, the LANKIQRTDA+V708I (SEQ ID NO:43), LANKTTNKDA+V708I (SEQ ID NO:48), and AAV6/AAV5 chimera provided for significantly higher transduction efficiency of and transgene expression in human skeletal muscle progenitor cultures six days post-infection as determined by immunofluorescence (FIG. 9A) and flow cytometry (FIG. 9B). This study illustrates the superior ability of NKIQRTD (SEQ ID NO:13)-, NKTTNKD (SEQ ID NO:14)-, and SEQ ID NO:62-comprising AAV capsid variants to deliver genes to skeletal muscle progenitors.

Example 6

Directed evolution was employed to discover novel adeno-associated virus (AAV) variants with superior gene delivery to cardiac and skeletal muscle cells following intravenous (IV) administration, a route of administration with significant advantages over other methods of gene delivery to the human heart and skeletal muscle (Example 1). The cell tropism following intramuscular administration of recombinant AAV virions comprising the novel AAV variant comprising a V708I substitution and the peptide LANKIQRTDA (SEQ ID NO:27) inserted between amino acids 587 and 588 (LANKIQRTDA+V708I; SEQ ID NO:43) was assessed in vivo in mice as a representative example of the ability of rAAV virions comprising NKIQRTD (SEQ ID NO:13)-containing AAV capsid variants to transduce muscle cells.

Figure 11A:
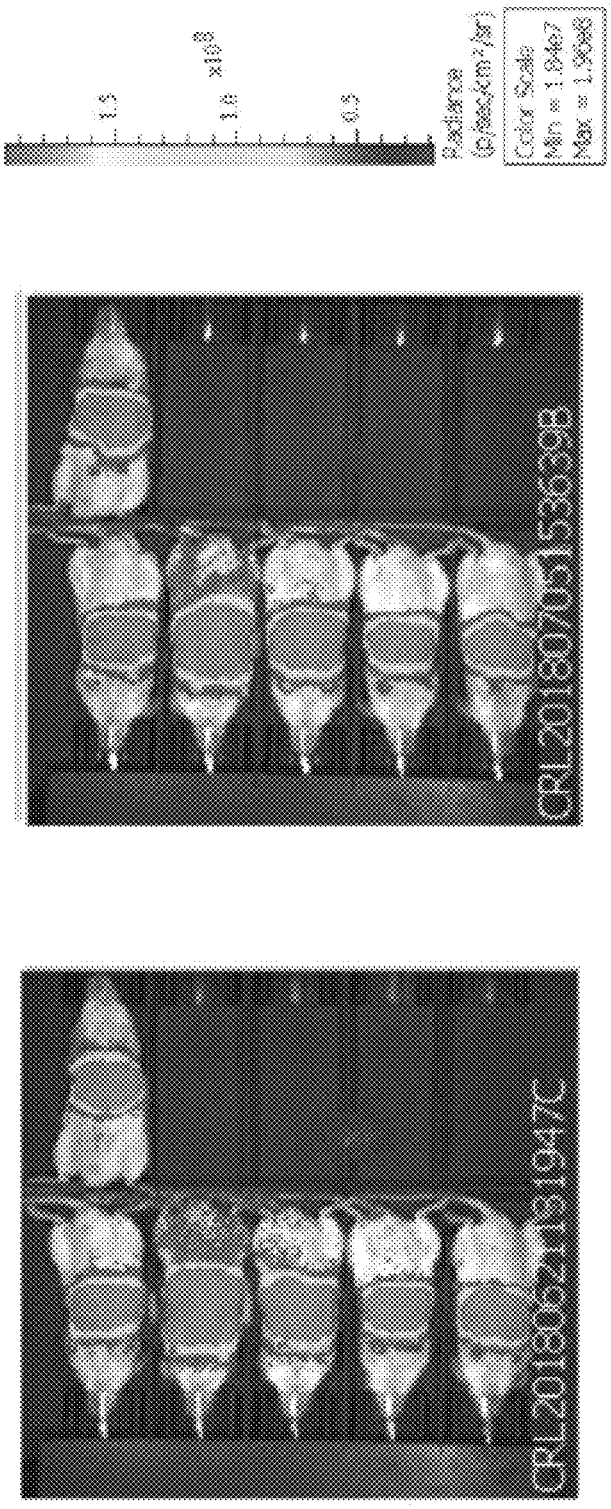
FIGS. 11A-B provide data on the transduction of mouse tissue in vivo by recombinant AAV virus comprising the novel AAV variant LANKIQRTDA+V708I (SEQ ID NO:43) capsid expressing a luciferase transgene under the control of the CAG promoter. The mice were given a single intravenous injection via the tail vein of $2\times10^{11}$ viral genomes per animal.
Figure 11B:
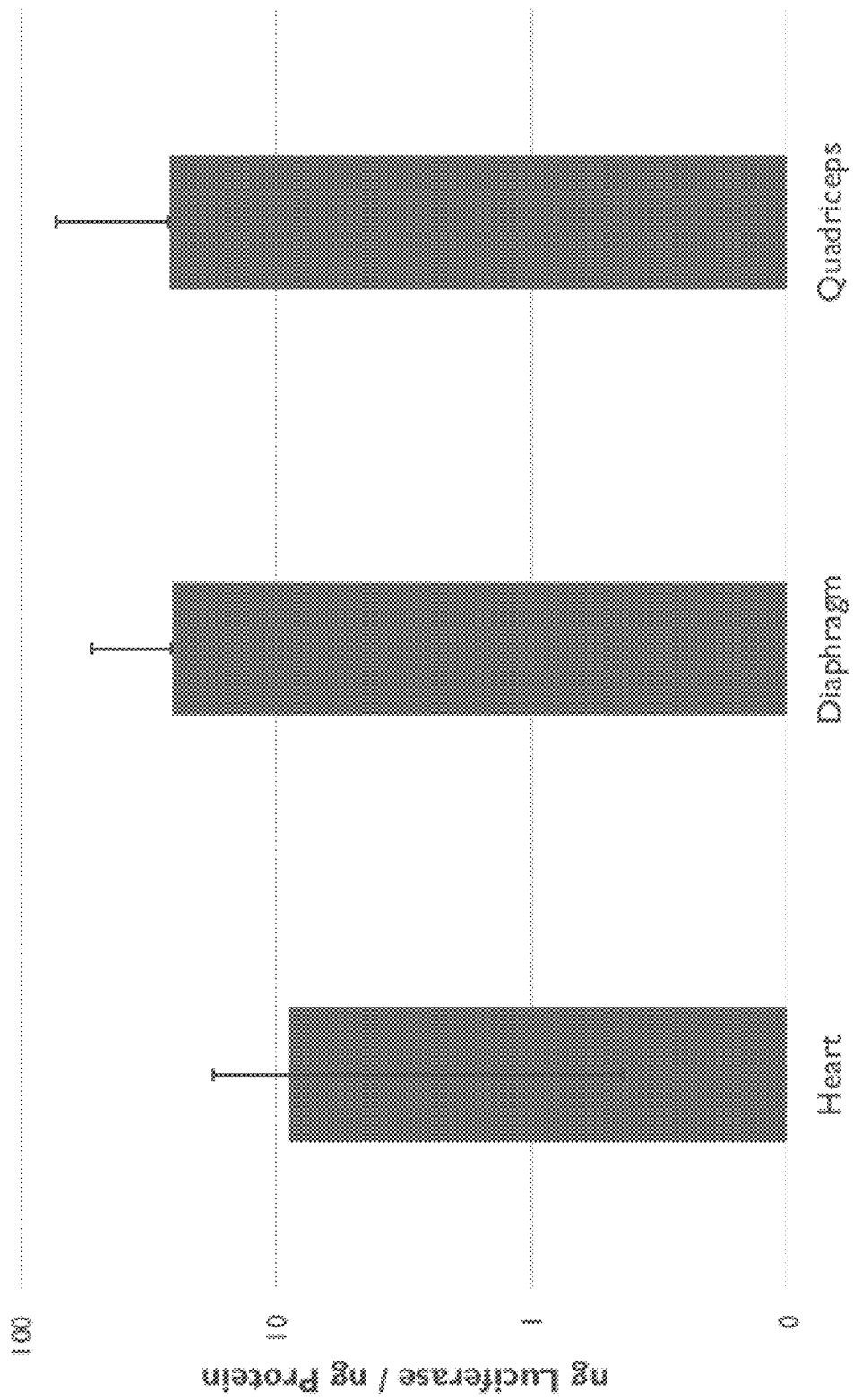

Recombinant AAV virions comprising the novel variant capsid LANKIQRTDA+V708I and a genome comprising a luciferase transgene operably linked to a CAG promoter (LANKIQRTDA+V708I (SEQ ID NO:43).CAG.luciferase) were manufactured using standard methods. B6 Albino (C57BL/6) mice were injected via tail vein intravenous injection with of $2 \times 10^{12}$ vg, and transduction was assessed in-life by luciferase imaging and post-mortem by tissue luciferase activity. In life imaging of luciferase at day 14 (left) and day 28 (right) post-administration demonstrate that the novel AAV variant LANKIQRTDA+V708I (SEQ ID NO:43) capsid can transduce mouse cells in vivo (FIG. 11A). Luciferase activity in heart, diaphragm, and quadriceps 56 days post-administration demonstrate that the novel AAV variant LANKIQRTDA+V708I (SEQ ID NO:43) capsid can transduce mouse cardiac and skeletal muscle in vivo (FIG. 11B).

This study illustrates gene delivery by the NKIQRTD (SEQ ID NO:13)-comprising variant following one of several clinically acceptable routes of administration. Similar efficacy is achievable with other variants comprising this peptide insertion motif. Likewise, similar efficacy is achievable with other variants disclosed herein that were identified using the same directed evolution approach.

Example 7

Directed evolution was employed to discover novel adeno-associated virus (AAV) variants with superior gene delivery to cardiac and skeletal muscle cells following intravenous (IV) administration, a route of administration with significant advantages over other methods of gene delivery to the human heart and skeletal muscle (Example 1). The cell tropism following intramuscular administration of recombinant AAV virions comprising the novel AAV variant comprising a V708I substitution and the peptide LANKIQRTDA (SEQ ID NO:27) inserted between amino acids 587 and 588 (LANKIQRTDA+V708I; SEQ ID NO:43) was assessed in vivo in non-human primates (NHP) as a representative example of the ability of rAAV variants comprising NKIQRTD (SEQ ID NO:13)-containing AAV capsid variants to transduce muscle cells.

Figure 12A:
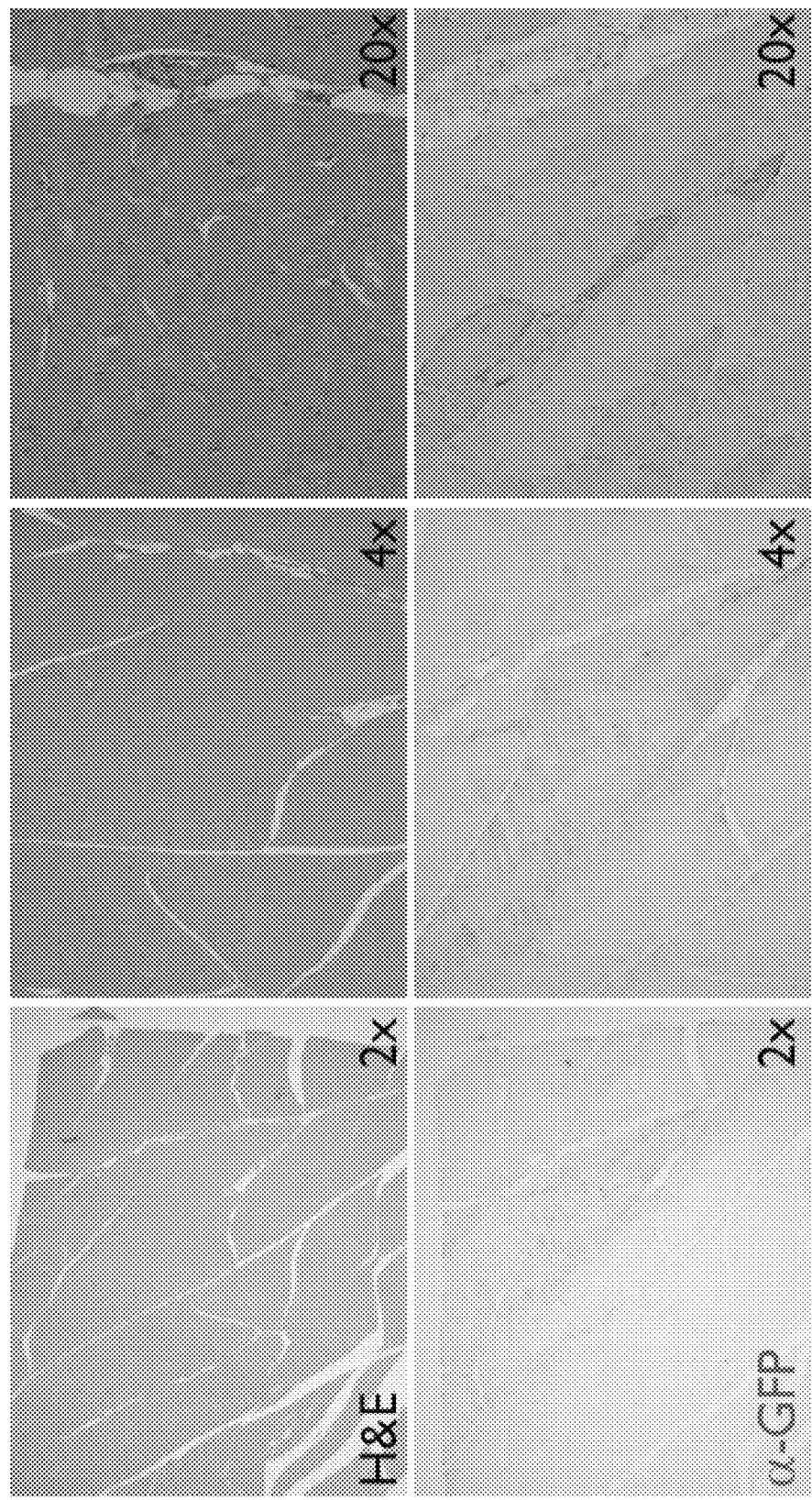
FIGS. 12A-B provide data on the transduction of non-human primate skeletal muscle in vivo by recombinant AAV virus comprising the novel AAV variant LANKIQRTDA+ V708I (SEQ ID NO:43) capsid expressing a GFP transgene under the control of the CAG promoter. The non-human primate was given 3 intramuscular injections of $10^{11}$ viral genomes each into the left vastus lateralis, and the muscle tissue was analyzed 4 weeks post-administration.
Figure 12B:
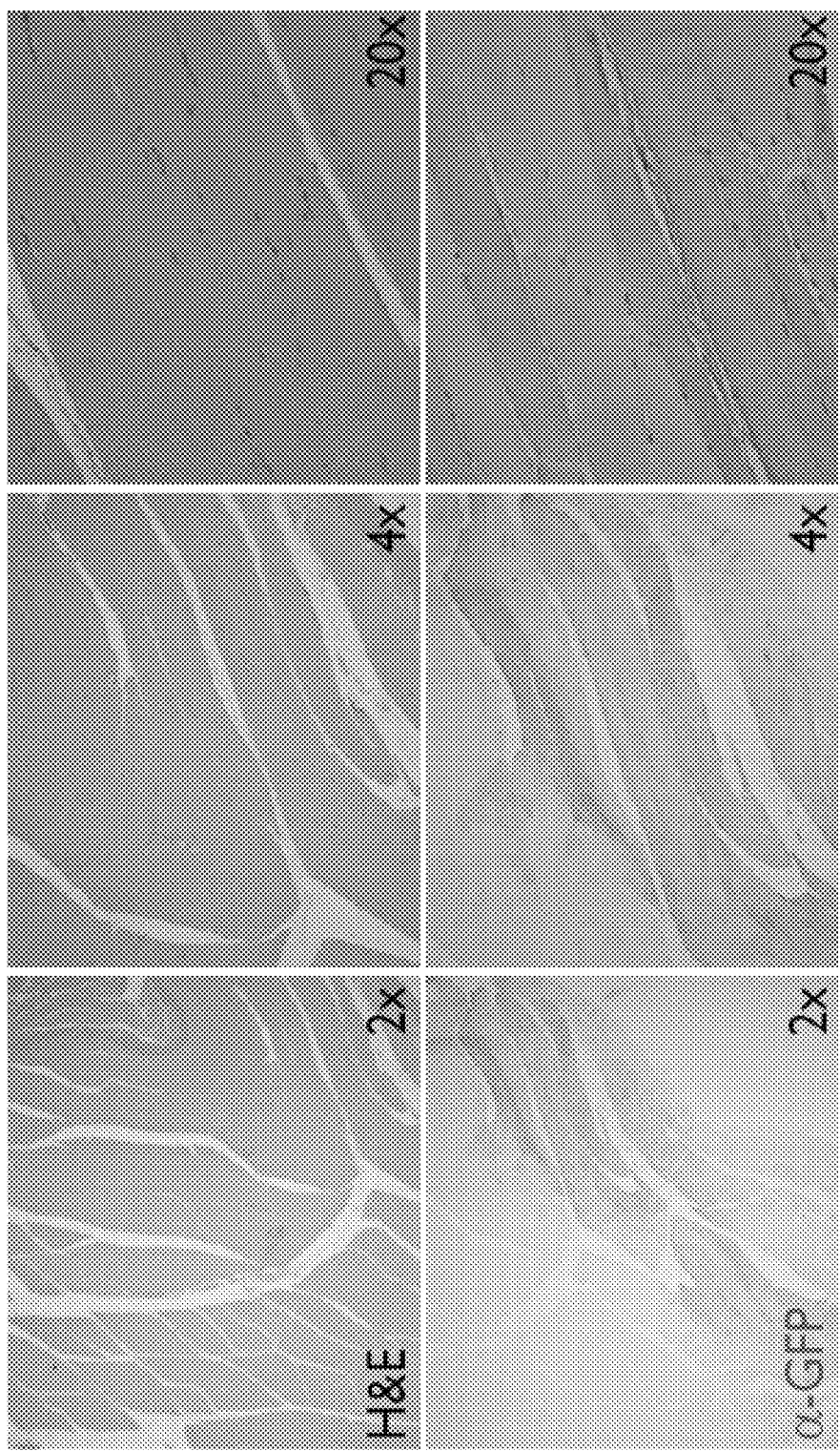

Recombinant AAV virions comprising the novel variant capsid LANKIQRTDA+V708I (SEQ ID NO:43) and a genome comprising a green fluorescent protein (GFP) transgene operably linked to a CAG promoter (LANKIQRTDA+V708I (SEQ ID NO:43).CAG.GFP) were manufactured using standard methods. Cynomolgus macaques were injected via intramuscular injection with three doses of vector into sites in the vastus lateralis of $1 \times 10^{11}$ vg and the transduction of skeletal muscle cells was assessed post-mortem by immunofluorescence imaging. Representative images of haemotoxylin and eosin (H&E) and anti-GFP antibody staining of cross-sections of the proximal biopsy site at 2×, 4×, and 20× magnification demonstrate that the novel AAV variant LANKIQRTDA+V708I (SEQ ID NO:43) capsid can transduce primate skeletal muscle cells in vivo (FIG. 12A). Representative images of haemotoxylin and eosin (H&E) and anti-GFP antibody staining of longitudinal sections of the distal biopsy site at 2×, 4×, and 20× magnification demonstrate that the novel AAV variant LANKIQRTDA+V708I (SEQ ID NO:43) capsid can transduce primate skeletal muscle cells in vivo (FIG. 12B).

This study illustrates gene delivery by the NKIQRTD (SEQ ID NO:13)-comprising variant following one of several clinically acceptable routes of administration. Similar efficacy is achievable with other variants comprising this peptide insertion motif. Likewise, similar efficacy is achievable with other variants disclosed herein that were identified using the same directed evolution approach.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method for delivering a heterologous nucleic acid encoding a gene product to a muscle cell, the method comprising contacting the muscle cell with a recombinant adeno-associated virus (rAAV), the rAAV comprising (i) the heterologous nucleic acid and (ii) a variant AAV capsid protein comprising a peptide insertion with a length of 7 to 13 amino acids covalently inserted in the GH-loop of the capsid protein relative to a corresponding parental AAV capsid protein, wherein the peptide insertion comprises the amino acid sequence NKTTNKD (SEQ ID NO: 14).

2. The method according to claim 1, wherein the insertion peptide has from 1 to 3 spacer amino acids ($Y_1$-$Y_3$) at the amino terminus and/or has from 1 to 3 spacer amino acids ($Y_1$-$Y_3$) at the carboxyl terminus of amino acid sequence NKTTNKD (SEQ ID NO: 14), wherein each of $Y_1$-$Y_3$ is independently selected from Ala, Leu, Gly, Ser, Thr, and Pro.

3. The method according to claim 2, wherein the insertion peptide is LANKTTNKDA (SEQ ID NO:28).

4. The method according to claim 3, wherein the variant capsid protein comprises a V708I amino acid substitution relative to VP1 of AAV2 (SEQ ID NO: 2) or the corresponding position in the capsid protein of another AAV serotype and wherein the variant capsid protein comprises an amino acid sequence at least 90% identical to the entire length of the amino acid sequence set forth as SEQ ID NO:48.

5. The method according to claim 4, wherein the variant capsid protein comprises an amino acid sequence at least 95% identical to the entire length of the amino acid sequence set forth as SEQ ID NO:48.

6. The method according to claim 1, wherein the insertion site is located between two adjacent amino acids at a position between amino acids 570 and 611 of VP1 of AAV2 (SEQ ID NO:2), or the corresponding position in the capsid protein of another AAV serotype.

7. The method according to claim 6, wherein the insertion site is located between amino acids corresponding to amino acids 587 and 588 of VP1 of AAV2 (SEQ NO: 2) or between amino acids corresponding to amino acids 588 and 589 of VP1 of AAV2 (SEQ ID NO:2) or the corresponding position in the capsid protein of another AAV serotype.

8. The method according to claim 1, wherein the muscle cell is a cardiac or skeletal muscle cell.

9. The method according to claim 1, wherein the gene product is a protein, a small interfering RNA, an antisense RNA, a microRNA, and/or a short hairpin RNA.

10. The method according to claim 1, wherein the gene product is a protein selected from alpha galactosidase A (GLA), frataxin (FXN), dystrophin (DMD), acid alpha glucosidase (GAA), and muscle glycogen phosphorylase (PYGM).

11. The method according to claim 1, wherein the rAAV is delivered to the muscle cell by intravenous and/or intramuscular injection.

12. A method for treating a disease selected from Fabry disease, Friedreich's ataxia, Duchenne's muscular dystrophy, Pompe disease, and myophosphorylase deficiency, the method comprising administering to a subject a pharmaceutical composition comprising a pharmaceutically acceptable carrier and a therapeutically effective amount of a recombinant adeno-associated virus (rAAV), the rAAV comprising (i) a heterologous nucleic acid comprising a nucleotide sequence encoding a protein selected from alpha galactosidase A (GLA), frataxin (FXN), dystrophin (DMD)), acid alpha glucosidase (GAA), and muscle glycogen phosphorylase (PYGM) and (ii) a variant AAV capsid protein comprising a peptide insertion with a length of 7 to 13 amino acids covalently inserted in the GH-loop of the capsid protein relative to a corresponding parental AAV capsid protein, wherein the peptide insertion comprises the amino acid sequence NKTTNKD (SEQ ID NO: 14), wherein said nucleotide sequence encoding said protein is operably linked to an expression control sequence.

13. The method according to claim 12, wherein the insertion peptide has from 1 to 3 spacer amino acids ($Y_1$-$Y_3$) at the amino terminus and/or has from 1 to 3 spacer amino acids ($Y_1$-$Y_3$) at the carboxyl terminus of amino acid sequence NKTTNKD (SEQ ID NO: 14), wherein each of $Y_1$-$Y_3$ is independently selected from Ala, Leu, Gly, Ser, Thr, and Pro.

14. The method according to claim 13, wherein the insertion peptide is LANKTINKDA (SEQ ID) NO: 28).

15. The method according to claim 14, wherein the variant capsid protein comprises a V708I amino acid substitution relative to VP1 of AAV2 (SEQ ID NO: 2) or the corresponding position in the capsid protein of another AAV serotype and wherein the variant capsid protein comprises an amino acid sequence at least 90% identical to the entire length of the amino acid sequence set forth as SEQ ID NO:48.

16. The method according to claim 15, wherein the variant capsid protein comprises an amino acid sequence at least 95% identical to the entire length of the amino acid sequence set forth as SEQ ID NO:48.

17. The method according to claim 12, wherein the insertion site is located between two adjacent amino acids at a position between amino acids 570 and 611 of VP1 of AAV2 (SEQ ID NO:2), or the corresponding position in the capsid protein of another AAV serotype.

18. The method according to claim 17, wherein the insertion site is located between amino acids corresponding to amino acids 587 and 588 of VP1 of AAV2 (SEQ NO: 2) or between amino acids corresponding to amino acids 588 and 589 of VP1 of AAV2 (SEQ ID NO:2) or the corresponding position in the capsid protein of another AAV serotype.

19. The method according to claim 12, wherein the disease is Fabry disease and wherein the heterologous nucleic acid comprises a nucleotide sequence encoding GLA.

20. The method according to claim 19, wherein the rAAV or pharmaceutical composition comprising the rAAV is administered to the subject by intravenous and/or intramuscular injection.

* * * * *